(12) United States Patent
Eguchi et al.

(10) Patent No.: US 7,767,987 B2
(45) Date of Patent: Aug. 3, 2010

(54) ELECTRON BEAM IRRADIATION METHOD, ELECTRON BEAM IRRADIATION APPARATUS, AND ELECTRON BEAM IRRADIATION APPARATUS FOR OPEN-MOUTHED CONTAINER

(75) Inventors: Shiro Eguchi, Chiba (JP); Isao Hashimoto, Hitachi (JP); Shigekatsu Sato, Hitachi (JP); Hidenobu Koide, Ichihara (JP); Nobuyuki Hashimoto, Ichihara (JP); Takayuki Suzuki, Kisarazu (JP); Satoru Gozaki, Ichihara (JP); Tomoyuki Hikosaka, Ichihara (JP); Yukio Okamoto, Kisarazu (JP); Hiroyuki Fujita, Hitachi-Ohta (JP)

(73) Assignee: Japan AE Power Systems Corporation, Tokyo (JP)

( * ) Notice: Subject to any disclaimer, the term of this patent is extended or adjusted under 35 U.S.C. 154(b) by 242 days.

(21) Appl. No.: 12/065,681

(22) PCT Filed: Sep. 21, 2006

(86) PCT No.: PCT/JP2006/318777

§ 371 (c)(1),
(2), (4) Date: Mar. 4, 2008

(87) PCT Pub. No.: WO2007/046213

PCT Pub. Date: Apr. 26, 2007

(65) Prior Publication Data

US 2009/0134338 A1 May 28, 2009

(30) Foreign Application Priority Data

| Oct. 18, 2005 | (JP) | ............................. 2005-302874 |
| Oct. 18, 2005 | (JP) | ............................. 2005-302875 |
| Oct. 18, 2005 | (JP) | ............................. 2005-302876 |
| Apr. 28, 2006 | (JP) | ............................. 2006-124738 |

(51) Int. Cl.
G21K 1/08 (2006.01)
H01J 3/14 (2006.01)
H01J 3/26 (2006.01)
H01J 49/42 (2006.01)

(52) U.S. Cl. ............ 250/492.3; 250/492.1; 250/454.11; 426/392; 426/383; 426/35; 426/22; 426/235; 426/398; 426/186.04; 204/157; 204/12; 436/1; 436/166

(58) Field of Classification Search ............. 250/492.3, 250/393 R, 492.1, 454.11; 426/392, 383, 426/35, 22, 235, 398, 186.04; 204/157.15; 436/1, 166
See application file for complete search history.

(56) References Cited

U.S. PATENT DOCUMENTS 7,183,563 B2 * 2/2007 Avnery ..................... 250/492.3
7,435,981 B2 * 10/2008 Naka et al. ............... 250/492.3

FOREIGN PATENT DOCUMENTS

JP          37-18446          11/1962

(Continued)

OTHER PUBLICATIONS

International Search Report dated Nov. 28, 2006.

(Continued)

Primary Examiner—Jack I Berman
Assistant Examiner—Meenakshi S Sahu
(74) Attorney, Agent, or Firm—Young Basile

(57) ABSTRACT

There are provided an electron beam application method and an electron beam application device capable of uniformly applying electron beams to an object even if the electron beams have a low energy. For this, electron beams (EB) are applied to a beverage container (30) (object) within a magnetic barrier (MF) formed by combining a plurality of magnetic fields generated in an electron beam application region.

17 Claims, 20 Drawing Sheets

FOREIGN PATENT DOCUMENTS

| | | |
|---|---|---|
| JP | 62-1200 | 1/1987 |
| JP | 5-166487 | 7/1991 |
| JP | 7-209498 | 8/1995 |
| JP | 9-150813 | 6/1997 |
| JP | 9-292498 | 11/1997 |
| JP | 10-268100 | 10/1998 |
| JP | 11-001212 | 1/1999 |
| JP | 11-081051 | 3/1999 |
| JP | 11-281798 | 10/1999 |
| JP | 2001-242297 A | 9/2001 |
| JP | 2002-104334 | 4/2002 |
| JP | 2002-255124 | 9/2002 |
| JP | 2002-308229 | 10/2002 |
| JP | 2002-341097 | 11/2002 |
| JP | 2003-302499 | 10/2003 |
| JP | 2005-247427 | 9/2005 |
| JP | 2005-258019 | 9/2005 |
| JP | 2008-308229 A | 12/2008 |

OTHER PUBLICATIONS

Japanese Office Action dated Aug. 11, 2009 for corresponding Japanese Application No. 2005-302874 with an English translation thereof.

Japanese Office Action dated Aug. 11, 2009 for corresponding Japanese Application No. 2005-302876 with an English translation thereof.

Translation of International Preliminary Report on Patentability for PCT/JP2006318777.

* cited by examiner

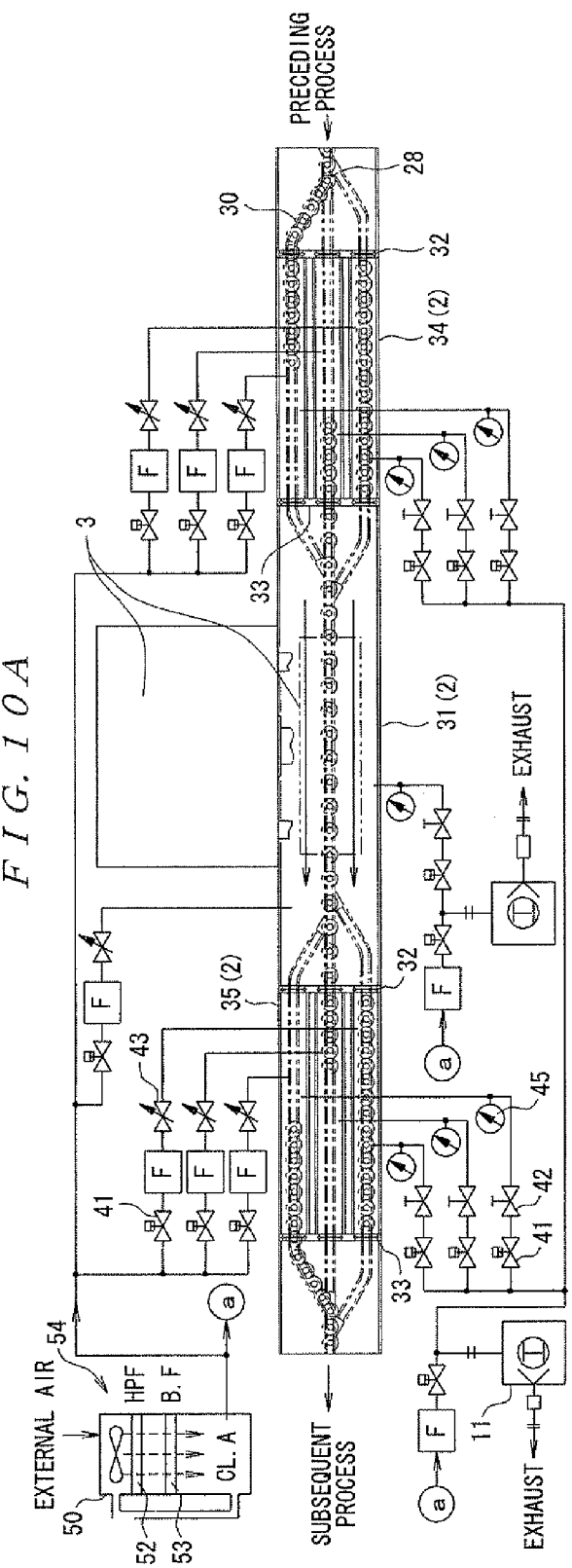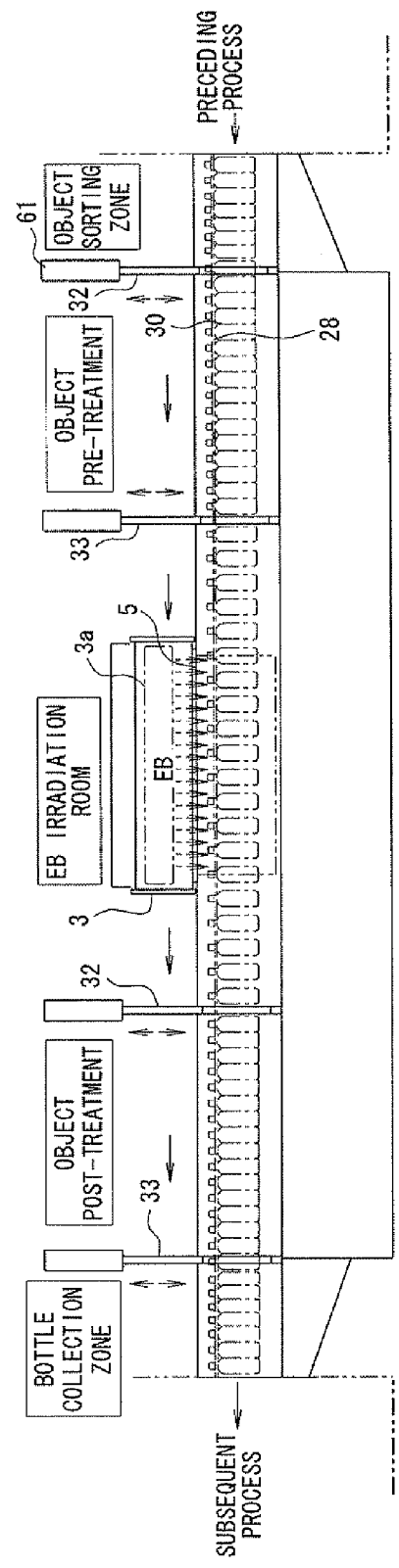

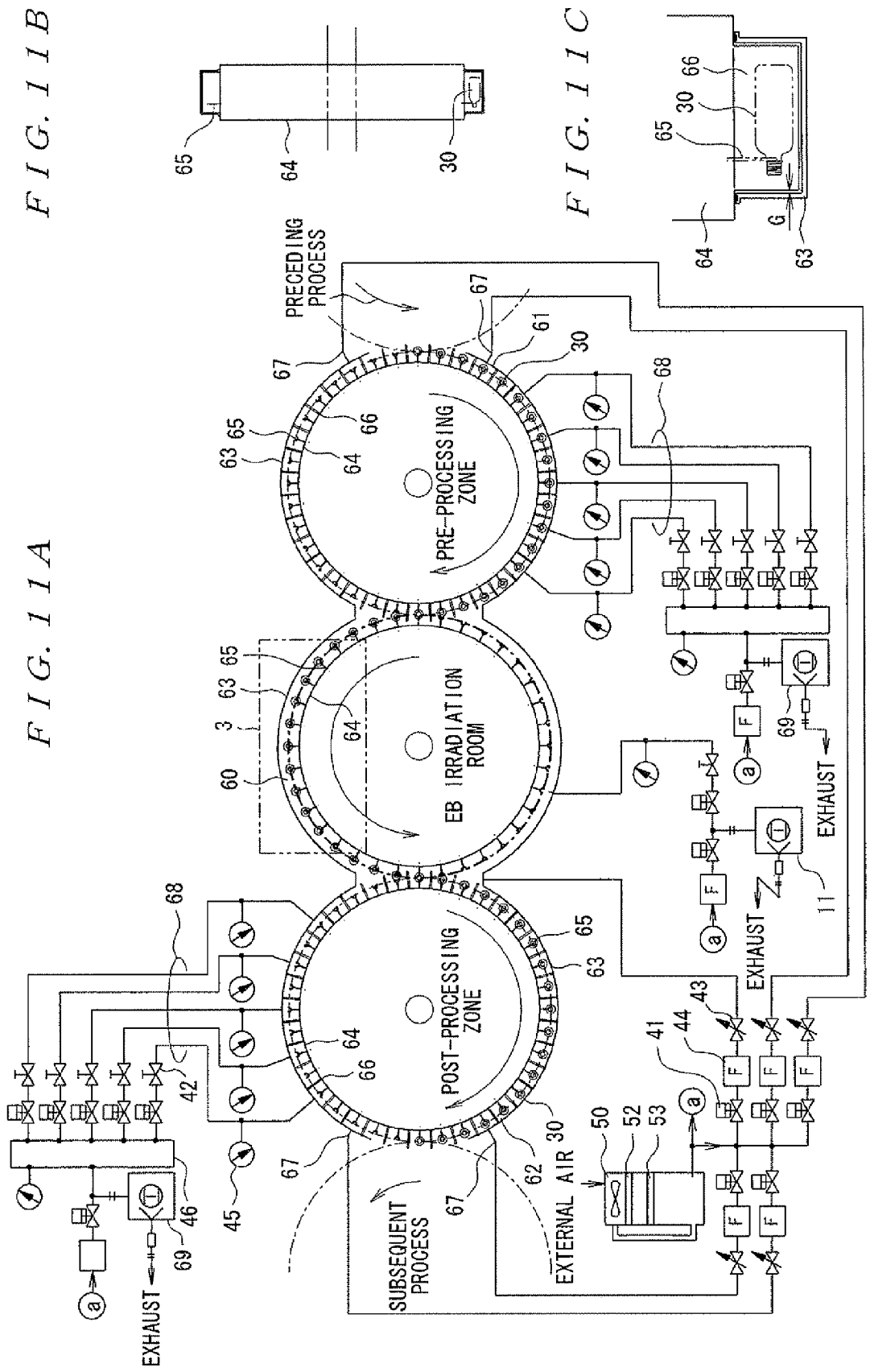
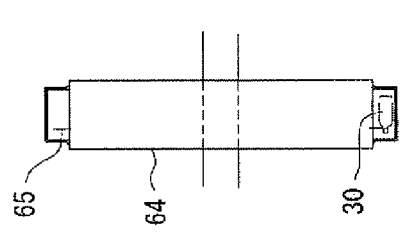
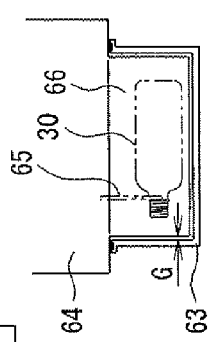
FIG. 11A
FIG. 11B
FIG. 11C

ELECTRON BEAM IRRADIATION METHOD, ELECTRON BEAM IRRADIATION APPARATUS, AND ELECTRON BEAM IRRADIATION APPARATUS FOR OPEN-MOUTHED CONTAINER

FIELD OF THE INVENTION

The present invention relates to an electron beam irradiation method and an electron beam irradiation apparatus for emitting electron beams to an object, more particularly to an electron beam irradiation method and an electron beam irradiation apparatus for emitting electron beams suitable for sterilizing objects, such as food and drink, water, pharmaceutical products, Chinese medicines, cosmetics, feeding stuffs, fertilizer, or to packaging material for those objects, and more particularly to an electron beam irradiation apparatus suitable for sterilizing the interior and exterior surfaces of plastic open-mouthed containers.

BACKGROUND OF THE ART

The conventional electron beam irradiation methods and apparatuses of this kind have been generally configured to irradiate the objects with high-energy electron beams by utilizing the penetration power. The conventional electron beam irradiation methods and apparatuses of high energy type had a problem that the facilities tended to be large and the energy efficiency was low. To simplify the facilities and improve the energy efficiency, there have been proposed methods and apparatuses for emitting electron beams of low energy type, which enable an object to be irradiated with electron beams as uniformly as possible by using low-energy electron beams, by deflecting electrons, by utilizing a magnetic field, or by reflecting electrons with a reflector plate.

As a typical example of the above idea, technologies are disclosed in Patent Documents 1 and 2 as follows.

The technology in Patent Document 1 discloses an electron beam irradiation apparatus which includes an electron beam irradiation means for emitting electron beams towards an electron beam irradiation area and a plurality of magnetic field deflectors, arranged around the electron beam irradiation area, and configured to generate a plurality of magnetic fields, and also includes a transport means for transporting a three-dimensional object to the electron beam irradiation area.

The technology in Patent Document 2 discloses an electron beam irradiation apparatus which includes an electron beam irradiation means for irradiating a three-dimensional object with electron beams and also includes magnetic field deflectors arranged at a lower position of the object, and a transport means for transporting the object.

According to structures disclosed in Patent Document 1 and 2, by transporting an object on the transport means into the electron beam irradiation area, by generating electron beams by the electron beam irradiation means and emitting electrons to the electron beam irradiation area, and by deflecting emitted electron beams by the respective magnetic field deflectors, electron beams can be directed to various portions of the object.

Meanwhile, these days, plastic containers are widely used which have mouths through which beverage, food, medicine or cosmetic product is filled. The insides of those open-mouthed containers are sterilized to a bacteria-free condition, and those containers are filled with contents and tightly sealed. It has been proposed for a sterilization process to sterilize the interior and exterior surfaces of open-mouthed containers transported at high speed, by using electron beams in place of pharmaceutical agents, the use of which requires large-scale facilities.

An electron beam irradiation apparatus has been proposed, in which, for example, an open-mouthed plastic container, such as a PET bottle, is transferred by the transport means with its center axis at right angles with the transport direction, in other words, with the container laid on its side, to the electron beam irradiation area so as to be irradiated by the electron beam generating means, and the container is further transferred by another transport means, whose bottom is inclined, in such a way that, the rotating open-mouthed container while being rotated, is passed through a space for irradiation by the electron beam generating means, so that both interior and exterior surfaces of the open-mouthed container are irradiated with electron beams to be sterilized efficiently (Refer to Patent Document 3).

To cite another example, an electron beam irradiation apparatus has been proposed, in which an electron beam generating means is arranged to extend longitudinally, a sterilization process room is formed by a radiopaque material in a required length range, including an electron beam irradiation window, and its vicinity, of the electron beam generating means, and the open-mouthed container as an object is transported in upright position by the container transport means from the entrance to the exit of the sterilization process room, and the open-mouthed container is rotated on its axis by a rotating means from a position just before the container reaches the electron beam irradiation window of the electron beam generating means until it has passed the irradiation window to thereby obtain effects of the sterilization process and reduce the size of the apparatus (Refer Patent Document 4).

Furthermore, there has been proposed an example of a method and an apparatus of sterilization capable of sterilizing a number of containers by a single electron beam irradiation means and therefore reducing the size of the whole apparatus, wherein to sterilize the inside of a container by irradiation with electron beams, a container is transported in upright position into the sterilization process room by the transport means, low-energy electron beams from the electron beam irradiation apparatus are deflected to scan the container by an AC magnetic field in the transport direction, and by irradiating the inside of containers one container after another with subdivided electron beams from radial nozzles, to thereby sterilize the inside of a plurality of containers by a single electron beam irradiation means (Refer to Patent Document 5).

Patent Document 1: JP2002-308229A

Patent Document 2: JP11-281798A

Patent Document 3: JP10-268100A

Patent Document 4: JP11-1212A

Patent Document 5: JP2002-104334A

DISCLOSURE OF THE INVENTION

To emit electron beams uniformly to the whole area of the object, it is necessary to change the arrangement of the magnetic field deflectors and vary the magnetic field intensity. However, control to maintain the uniformity of irradiation is very hard to implement because of the high speed with which electrons are emitted, and those technologies of the above-mentioned patent document are not sufficient in terms of uniformity of electron beams emitted to the whole area of the object.

When an object is, for example, a three-dimensional object having a complicated shape or a sheet-form material, even if the electrons are deflected, it is difficult to make electron beams hit the side of an object opposite to the side facing the irradiating part of the electron beam irradiation means because of a large Larmor radius and fringing fields. It has been proposed to irradiate the opposite side of the object with secondary electrons reflected from the object and the reflector plate, but since the secondary electrons suffer large energy loss due to space distance, it is still difficult to maintain specified doses of radiation and achieve uniform irradiation.

Moreover, electron beams emitted from the electron beam irradiation apparatus of this kind collide with a surrounding gas as the ambient atmosphere and hit the structural part of the apparatus other than the object, the electron beams lose much of their energy. For this reason, it becomes more difficult to irradiate the object with electron beams uniformly.

When objects are transported continuously on a continuous production line, the above problems make it difficult to irradiate transported objects with low-energy electron beams uniformly and with high energy efficiency.

Therefore, the present invention has been made with the above problems in mind and has as its object to provide a method and an apparatus for uniformly irradiating an object with electron beams even if low-energy electron beams are applied.

The present invention has an object to provide a method and an apparatus for irradiation with electron beams, which can reduce energy loss of the electron beams even when low-energy electron beams are used, and also provide an electron beam irradiation apparatus capable of continuous irradiation with electron beams while reducing energy loss of electron beams.

Meanwhile, in the electron beam irradiation apparatus according to Patent Document 3, an open-mouthed container, which arrives in upright position, is turned on its side and while being transported lying on its side, the container is irradiated with electron beams. Therefore, in order to place the sterilization device on the production line, it is necessary to install a sideways-turning device and a raising device for containers, and in that case, the presence of those devices will cause a notable decrease in speed of container transport, and a problem here is that it is difficult to install those devices on the production line which is required to transport open-mouthed containers at high speed, and increase production efficiency. In the electron beam irradiation apparatus in Patent Document 4, it is possible to install those devices on the production lines of various products, but in the process where open-mouthed containers transported continuously pass by the electron beam irradiation window at a single point of the electron beam generating means, each container is irradiated on its side with electron beams for sterilization, and in order to sufficiently sterilize the interior and exterior surfaces of the open-mouthed containers, the transport speed needs to be slowed or some high-energy electron beam generating means needs to be used, which could be problem.

Furthermore, the electron beam irradiation apparatus according to Patent Document 5 has a problem that for the electron-beam irradiation process of open-mouthed containers transported continuously on the production line, the apparatus would be in a complicated structure because it is necessary to provide a number of radial nozzles for one electron beam irradiation means, and to direct electron beams sufficiently deep inside the open-mouthed containers, the transport speed needs to be slow, which will hinder an efficiency improvement of the production line.

More specifically, another object of the present invention is to provide an electron beam irradiation apparatus for open-mouthed containers, which can be mounted on the production line that transports open-mouthed containers at high speed, and which can effectively sterilize the open-mouthed containers with electron beams by using a low-energy electron beam generating means in an electron-beam irradiation process maintained at a negative pressure.

Another object of the present invention is to provide an electron beam irradiation apparatus for open-mouthed containers, which has a plurality of electron beam generating means appropriately arranged, and which can perform an adequate sterilization process by emitting electron beams from respective electron beam generating means to irradiate the interior and exterior surfaces of the open-mouthed containers being transported at a high speed almost equal to the speed of the production line.

To solve the above-mentioned problem, the present invention provides a method for irradiating an object with electron beams, characterized by forming a rotating magnetic field generated in the electron beam irradiation area, and irradiating the object with electron beams in the rotating magnetic field.

According to the present invention, an electron beam irradiation apparatus for irradiating an object with electron beams, comprises an electron beam radiating means for emitting electron beams into an electron beam irradiation area where an object is placed, and a magnetic field barrier forming means for forming a magnetic field barrier in such a way as to enclose the object by joining together a plurality of magnetic fields generated within the electron beam irradiation area.

In the present specification, "magnetic field barrier" refers to a synthesis of magnetic fields by generating a plurality of magnetic fields in an electron beam irradiation area and joining together those magnetic fields. Note that in Patent Document 1 mentioned above, for example, a plurality of magnetic fields are generated in the electron beam irradiation area, but they are all formed as individual magnetic fields, which do not form a joint magnetic barrier, not like in the present invention, in which respective magnetic fields are joined together.

According to the present invention, a magnetic field barrier is formed by joining together a plurality of magnetic fields generated in the electron beam irradiation area. Therefore, by irradiating an object with electron beams in this magnetic field barrier, the electron beams irradiating the object can be confined within the magnetic field barrier and the electron beams can be reflected at various angles. Consequently, the object can be irradiated with electron beams effectively and uniformly.

The magnetic field barrier is preferably formed by cusp fields or mirror fields. In this structure, it is possible to confine the electrons within the magnetic field barrier without energy loss. The disorderliness in the reflecting direction of electrons can be obtained effectively. For this reason, it is possible to irradiate an object with electron beams with improved efficiency.

The magnetic field barrier forming means is preferably adapted in such a way that at least one of the reflecting distance and the reflecting direction of electrons within the magnetic field barrier can be changed by adjusting the intensity of the magnetic fields generated. In this structure, the disorderliness of the electron reflecting direction can be obtained more effectively. Therefore, an object can be irradiated with uniform electron beams with high efficiency.

The magnetic field barrier forming means is preferably adapted in such a way that the reflecting direction of electron beams within the magnetic field barrier can be changed by at, least one of adjustment of the direction of the magnetic fields generated and whether there is occurrence of a rotating magnetic field. In this structure, the disorderliness of electron reflecting direction can be obtained more effectively. Therefore, an object can be irradiated with uniform electron beams more efficiently.

The above-mentioned magnetic field barrier forming means is suitable for adopting a structure including a plurality of magnetic field generators arranged to respectively generate magnetic fields to thereby enclose an object in the electron beam irradiation area. The structure described above is suitable for forming a magnetic field barrier in such a way as to enclose an object, and suitable also for uniformly irradiating the object with low-energy electron beams.

The magnetic field generator described is preferably formed by including one of a permanent magnet, an electromagnet, and a circular coil. If the field generator is structured as described, desired magnetic fields can be formed efficiently according to conditions that occasion demands.

The electron beam irradiation apparatus comprises an irradiation chamber for accommodating an object and controlling the ambient atmosphere around the object in a vacuum state or in a state filled with an ambient gas in a range from negative pressure to positive pressure, wherein the ambient gas is preferably one or a plurality of gases selected from air, oxygen, nitrogen, hydrogen, carbon dioxide, argon and helium. If it is structured as described, by controlling so that the ambient gas is in a vacuum state or in a state filled with an ambient gas at negative pressure, energy loss of the electrons can be lessened. Even in an ambient gas at normal pressure, if a gas of light specific gravity, such as helium, is used as the ambient gas, the energy loss of electrons can be made smaller than in an ambient gas of high specific gravity, such as air. Even in an ambient gas at positive pressure, depending on the level of pressure, by using a gas of light specific gravity, such as helium as the ambient gas, the energy loss of electrons can be reduced to a sufficiently low level. According to the type of object and its purpose of irradiation, the ambient gas can be selected as occasion demands, and the ambient gas around the object can be controlled to a desired state.

The electron beam irradiation means preferably includes an irradiation angle changing means capable of changing the irradiation angle of electron beams irradiated. If the electron beam irradiation means is structured as described, it is possible to change the entering angle of electron beams to be directed into the electron beam irradiation area. Therefore, electrons strike the magnetic field barrier at various angles, thus enabling disorderly irradiation from various directions. As a result, the object can be subjected to efficient and uniform irradiation of electrons.

The electron beam irradiation apparatus preferably further comprises an object transport means that transports an object in such a way as to enable the object to pass through the electron beam irradiation area. If the electron beam irradiation means is structured as described, the present invention can be applied in the middle of a batch type production line or a continuous production line on which the objects are transported.

The present invention can be preferably applied to uses in which the object is a container or a sheet-form material and the container or sheet-form material is sterilized by irradiation of electrons. In other words, the present invention can be applied to objects ranging from a complicate-shaped three-dimensional object to a flat object in compliance with the kind and shape of the object, and can irradiate the object with electron beams efficiently and uniformly. For example, the present invention can be appropriately applied to uses in which PET bottles for soft drinks and other plastic hollow bottles are sterilized by electron beam irradiation, or to uses in which unfolded paper sheet for milk-drink containers is sterilized by electron beam irradiation.

Furthermore, to solve the above-mentioned problem, the present invention relates to a method for irradiating an object with electron beams, and is characterized by generating a rotating magnetic field in an electron beam irradiation area and irradiating an object with electron beams within the rotating magnetic field.

In addition, the present invention relates to an electron beam irradiation apparatus for irradiating an object with electron beam, which includes an irradiation chamber for accommodating an object and forming an electron beam irradiation area, an electron beam irradiation means for emitting electron beams into the irradiation chamber, and a magnetic field generating means for generating a rotating magnetic field in such a way as to enclose the object.

The "rotating magnetic field" in the present invention drives a generated magnetic field to rotate in such a manner as to enclose the object, and implies all of three cases: a case where the generated magnetic field itself rotates about the object, another case is where the magnetic field itself does not rotate but the object is made to rotate inside the magnetic field enclosing the object, so that the magnetic field appears to rotate relative to the object, and yet another case is where the magnetic field is made to rotate about the object and also the object is made to rotate inside the magnetic field enclosing the object.

According to the present invention, a rotating magnetic field is generated, which encloses an object within the electron beam irradiation area. Since the object is irradiated with electron beams in the rotating magnetic field, the emitted electron beams are deflected in the rotating direction inside the rotating magnetic field. For this reason, energy loss is reduced, which would be caused by collisions of electrons with the component parts other than the object, and since the electron beams emitted to the object are deflected by the rotating magnetic field, the object can be irradiated with electron beams uniformly, particularly irradiated in its circumferential direction.

The magnetic field generating means is preferably structured to generate a plurality of rotating magnetic fields over the range that encloses the object. If it is structured in this manner, the plurality of rotating magnetic fields are mutually joined together to form, as it were, a barrier enclosing the object. Thus, by confining the electrons in a space, loss of energy can be suppressed adequately, and the object can be irradiated with electron beams uniformly.

Preferably, the magnetic field generating means is configured such that the plurality of rotating magnetic fields are generated separately. If the magnetic field generating means is structured in this way, the disorderliness of electron reflecting direction can be obtained effectively. And consequently the object can be irradiated with electron beams efficiently.

For example, if the rotating magnetic fields, generated separately, are moved in stages relative to the object (if the object is a perpendicularly extending object, it may be divided into an upper portion, a middle portion, and a lower portion, for example and those portions are sequentially irradiated with electron beams), the whole of the object can be irradiated evenly and effectively. Preferably, the magnetic field generating means is configured such that by changing the rotating direction of the generated rotating magnetic fields, the reflecting direction of electron beams in the rotating magnetic field can be changed. Under this configuration, the disorderliness of electron reflection directions can be obtained more effectively. Therefore, irradiation of the object with uniform electron beams can be obtained efficiently.

Preferably, the magnetic field generating means includes a plurality of magnetic field generators for respectively generating magnetic fields that are arranged to enclose the object in the irradiation chamber. Under this configuration, the magnetic field generating means can have a structure suitable for forming a rotating magnetic field in such a way as to enclose the object.

The magnetic field generator is formed by a circular magnetic field generating coil, and can adopt a structure in which the rotating magnetic field can be generated by supplying electric power to the magnetic field generating coil. Under this configuration, too, the magnetic field generator can have a structure suitable for forming a rotating magnetic field in such a way as to enclose the object. As for power supply, an AC power supply can be used, and a three-phase or any other polyphase AC power supply may be used. An AC power supply is suitable for uniform irradiation of an object with electron beams. Preferably, the magnetic field generating means is adapted to be able to change, for example, an effective value of an AC voltage to energize the magnetic field generating coil to change the intensity of the rotating magnetic field. Under this configuration, the direction of rotation of electrons, which is made disorderly, can be obtained, by which it is possible to achieve efficient and uniform irradiation of electron beams.

The magnetic field generator includes a plurality of permanent magnets arranged in a circular ring, and a magnetic-field-generator rotating means for rotating the plurality of permanent magnets arranged in a circular ring about the central axis thereof. The magnetic field generator is preferably configured such that the rotating magnetic field is generated by the magnetic-field-generator rotating means which rotates the plurality of permanent magnets arranged in a circular ring to generate a rotating magnetic field. Under this configuration, a desired rotating magnetic field can be formed efficiently according to conditions that occasion demands.

The magnetic field generator includes a plurality of permanent magnets arranged in a circular ring and an object rotating means for rotating the object about the central axis of the plurality of permanent magnets arranged in a circular ring. The magnetic field generator is preferably configured such that the rotating magnetic field is generated as a magnetic field relative to the object that is rotated inside the plurality of permanent magnets arranged in a circular ring by the object rotating means. Under this configuration, a desired rotating magnetic field can be formed efficiently according to conditions that occasion demands.

The magnetic field generating means is preferably formed by including an axial-direction moving means for moving the magnetic field generators in the direction of the axis line of the rotating magnetic field generated by the magnetic field generators. Under this configuration, the disorderliness of the reflecting direction of electrons can be obtained effectively. Therefore, the object can be irradiated by electron beams which are more efficient and uniform in the axial direction, too.

The irradiation chamber further includes an irradiation chamber for accommodating the object, and controlling the ambient atmosphere around the object in a vacuum state or in a state filled with an ambient gas at negative to positive pressure, and the ambient gas is preferably selected from one of a plurality of air, oxygen, nitrogen, hydrogen, carbon dioxide, argon and helium. If it is structured as described, by controlling so that the ambient gas is in a vacuum state or in a state filled with an ambient gas at negative pressure, energy loss of the electrons can be lessened. Even in an ambient gas at normal pressure, if a gas of light specific gravity, such as helium, is used as the ambient gas, the energy loss of electrons can be made smaller than in an ambient gas of high specific gravity, such as air. Even in an ambient gas at positive pressure, depending on its level of pressure, by using a gas of light specific gravity, such as helium as the ambient gas, the energy loss of electrons can be reduced to a sufficiently low level.

The electron beam irradiation means preferably comprises an irradiating angle changing means for changing an irradiation angle of electron beams. Under this configuration, an entering angle of electron beams emitted to the electron beam irradiation area can be changed. Therefore, electrons can strike at various angles to the rotating magnetic field, thus enabling disorderly irradiation from many directions. Thus, more efficient and uniform irradiation of the object can be obtained.

The electron beam irradiation means preferably further includes an object transport means that transports the object in such a manner as to enable it to pass through the electron beam irradiation area (or the irradiation chamber). Under this configuration, the present invention can be applied in the middle of a batch-type or continuous production line on which the object is transported.

The present invention can be suitably applied to uses in which the objects are containers or a sheet-form material and the containers or sheet-form material are sterilized by being irradiated with electron beams. In other words, the present invention can be applied to objects ranging from complicated-shaped three-dimensional objects to a flat object according to the kind and the shape of objects, and can irradiate the object with electron beams efficiently and uniformly. For example, the present invention can be appropriately applied to uses in which PET bottles for soft drinks and other plastic hollow bottles are sterilized by electron beam irradiation, or to uses in which unfolded paper sheet for milk-drink containers is sterilized by electron beam irradiation.

To solve the above problem, the present invention provides a method that uses the electron beam irradiation means capable of uniform irradiation of electron beams to the surfaces of the object accommodated in the irradiation chamber, characterized in that the atmosphere around the electron beam irradiation means is controlled to a first negative pressure and that the irradiation chamber has an atmosphere controlled to a second negative pressure whose absolute pressure is higher than that of the first negative pressure, and in this atmosphere, irradiation with electron beams is performed.

The present invention provides an electron beam irradiation apparatus that comprises an irradiation chamber accommodating an object; and an electron beam irradiation means capable of uniform irradiation to the surface of the object in the irradiation chamber, wherein the electron beam irradiation means is installed in an electron beam generating room capable of maintaining an inside pressure, and wherein the irradiation chamber is configured to be adjacent to the electron beam generating room capable of maintaining the inside pressure separately from the electron beam generating room, and wherein there is provided a pressure control means for controlling so that the electron beam generating room is at a first negative pressure and the irradiation chamber is at a second negative pressure whose absolute pressure is higher than that of the first negative pressure.

According to the present invention, the atmosphere around the electron beam irradiation means is controlled to the first negative pressure and the interior of the irradiation chamber is in an atmosphere controlled to a second negative pressure whose absolute pressure is higher than that of the first negative pressure, and in the predetermined atmosphere irradiation with electron beams is performed. Therefore, the ambient gas as the atmosphere is reduced, and energy loss of electron beams, which would be caused by collision with the ambient gas, can be reduced.

The pressure control means is preferably adapted to change the level of the second negative pressure to change the degree of scattering of electrons. Under this configuration, by changing the level of the second negative pressure in the irradiation chamber (hereafter often referred to simply as "irradiation chamber"), the degree of scattering of electrons can be changed, so that the disorderliness of electron flying direction can be obtained. Therefore, the object can be irradiated with electrons more efficiently.

An electron beam irradiation apparatus of the present invention comprises a plurality of sub rooms formed such that the inside pressure can be maintained separately and installed adjacent to the irradiation chamber; and an object transport means for transporting the object between the plurality of sub rooms and the irradiation chamber, wherein the plurality of sub rooms include at least a front sub room provided in a position from which objects can be transported into the electron beam irradiation by the object transport means and a rear sub room provided in a position to which objects can be transported from inside the irradiation chamber, and wherein the above-mentioned pressure control means is preferably configured to control the inside pressure of the plurality of sub rooms separately from the irradiation chamber. Under this configuration, this invention can be applied in the middle of a batch-type or continuous production line on which the objects are being transported. In a production line on which objects are continuously carried into the electron beam irradiation room from the environment of room air and carried out therefrom, since sub rooms are provided before and after the irradiation chamber, the level of the second negative pressure can be maintained appropriately.

In a configuration having a plurality of sub rooms as mentioned above, it is preferable to make an arrangement that the pressure of the front sub room and the rear sub room can be changed so as to adapt to the level of the second negative pressure. Under this configuration, it is possible to securely maintain the second negative pressure in the electron beam irradiation chamber.

And, the ambient gas in the irradiation chamber is preferably one or a plurality of gases selected from air, oxygen, nitrogen, hydrogen, carbon dioxide, argon and helium. Under this configuration, by controlling the ambient atmosphere to the state of the second negative pressure by using helium, for example, whose specific gravity is light, energy loss of electrons can be reduced. By selecting an ambient gas properly according to the type of an object and the purpose of irradiation, the ambient atmosphere around the object can be controlled to a predetermined state.

If the plurality of sub rooms are arranged serially to or parallel with the irradiation chamber, when considering the configuration of the object transport means, its layout can be simple. If two or more sub rooms are provided in the transport direction and the adjacent sub rooms are configured to be mutually separated by partition walls having at least one of pivoted doors and a labyrinth seal structure, these sub rooms will be suitable for a configuration such that objects are continuously transported while controlling a pressure leak. If an object is a continuous sheet, the labyrinth seal structure can be preferably used.

If the front sub room, the irradiation chamber, and the rear sub room are configured to be supplied, as a leak gas for control of the second negative gas, with clean air that meets at least one of the conditions of no dust and no bacteria, this is preferred when the objects are food and drink, water, pharmaceutical products, Chinese medicines, cosmetics, etc. or packaging material or the like for those objects.

The front sub room, the irradiation chamber, and the rear sub room are preferably configured to be able to perform multi-stage pressure control and to make the gas flow in a desired direction. Under this configuration, for example, if the gas is made to flow from the succeeding process to the preceding process, it is possible to prevent airborne bacteria and dust from entering from unprocessed products (from the preceding process) and also prevent gases containing sterilized bacteria from diffusing disorderly.

The present invention can be preferably applied to uses in which the object is a container or a sheet-form material and the container or sheet-form material is sterilized by irradiation of electrons. In other words, the present invention can be applied to objects ranging from a complicate-shaped three-dimensional object to a flat object in compliance with the kind and shape of the object, and can irradiate the object with electron beams efficiently and uniformly. For example, the present invention can be appropriately applied to uses in which PET bottles for soft drinks and other plastic hollow bottles are sterilized by electron beam irradiation.

To solve the above problem, the present invention provides an electron beam irradiation apparatus for open-mouthed containers, wherein a front pressure adjusting chamber and a rear pressure adjusting chamber are connected integrally to the side faces of the irradiation process chamber for maintaining a negative pressure state with its own pressure reducing means, and a rotating transport device is disposed rotatably in each pressure adjusting chamber, a plurality of holding devices for holding open-mouthed containers are provided at roughly equal intervals on the outer surfaces of the rotating transport devices, and wherein the pressure reducing means is provided in such a way that the open-mouthed containers can be transferred one after another from one rotating transport device to the other rotating transport device from the front pressure adjusting chamber to the rear pressure adjusting chamber, that partition walls are provided at the rotating transport devices in the front and rear pressure adjusting chambers to divide the holding devices to form a plurality of small compartments by using the partition walls and chamber wall surfaces when the rotating transport devices are moving, and that it is arranged that the pressure is reduced in the small compartments in a range from an open-mouthed container entrance side of the front pressure adjusting chamber to the irradiation process chamber side and in the other range from the irradiation process chamber to the open-mouthed container exit side of the rear pressure adjusting chamber, and wherein at least one electron beam irradiation means is arranged in the irradiation process chamber.

According to the electron beam irradiation apparatus for open-mouthed containers in the present invention, since an irradiation process is performed in the irradiation process block where a negative pressure is maintained, a low-energy electron beam irradiation means can be used, and open-mouthed containers can be sterilized effectively by electron beams. Moreover, while open-mouthed containers held in upright position by the holding devices are transferred at high speed, they can be sterilized by electron beam irradiation, and this apparatus can be mounted and used on the production line.

According to the present invention, there is provided an electron beam irradiation apparatus for open-mouthed containers, wherein a front pressure adjusting chamber and a rear pressure adjusting chamber are connected integrally to the side faces of the irradiation process chamber for maintaining a negative pressure state with its own pressure reducing means, and a rotating transport device is disposed rotatably in each pressure adjusting chamber, a plurality of holding devices for holding open-mouthed containers are provided at roughly equal intervals on the outer surfaces of the rotating transport devices, wherein a pressure reducing means is provided in such a way that open-mouthed containers can be transferred one after another from one rotating transport device to the other rotating transport device from the front pressure adjusting chamber to the rear pressure adjusting chamber, that partition walls are provided at the rotating transport devices in the front and rear pressure adjusting chambers to divide the holding devices to form a plurality of small compartments by using the partition walls and chamber walls when the rotating transport devices are rotating, and that it is arranged that the pressure is reduced in the small compartments in a range from an open-mouthed container entrance side of the front pressure adjusting chamber to the irradiation process chamber side and in the other range from the irradiation process chamber to the open-mouthed container exit side of the rear pressure adjusting chamber, and wherein a plurality of electron beam irradiation means are arranged in positions along an open-mouthed-container transporting circular arc of the irradiation process chamber.

In an electron beam irradiation apparatus for open-mouthed containers according to the present invention, a plurality of electron beam irradiation means are arranged in positions along a transport circular arc of the irradiation process chamber, and therefore it is possible to effectively perform a sterilization process by irradiating electron beams to the interior and exterior surfaces of open mouthed containers while they are transported at high speed just as in the production line.

In the electron beam irradiation apparatus for open-mouthed containers according to the present invention, the irradiation process chamber preferably has a diameter larger than that of the front pressure adjusting chamber or the rear pressure adjusting chamber, and a plurality of electron beam irradiation means are arranged above the irradiation process chamber.

In the electron beam irradiation means for open-mouthed containers according to the present invention, in the irradiation process chamber as the room for irradiation with electron beams, the electron beam deflecting means are preferably arranged in positions opposed to the electron beam irradiation means and at different heights of open-mouthed containers irradiated with electron beams.

It is desirable if a plurality of the electron beam deflecting means are arranged such that the deflection directions of electron beams are bent in circumferential direction at different angles with respect to the central axis of open-mouthed containers.

It is desirable if an axial rotation device for rotating an open-mouthed container on its axis by a rotation drive force caused by the movement of the rotating transport device is arranged to each of a plurality of holding devices mounted on the rotating transport devices in the irradiation process chamber.

By the electron beam irradiation apparatus for open-mouthed containers according to the present invention, since an irradiation process is performed in the irradiation process block where a negative pressure is maintained, a low-energy electron beam irradiation means can be used, and open-mouthed containers can be sterilized effectively by electron beams. Moreover, while open-mouthed containers held in upright position by the holding devices are transferred at high speed, they can be sterilized by electron beam irradiation, this apparatus can be mounted and used on the production line.

Furthermore, if the electron beam irradiation apparatus is configured according to the present invention, open-mouthed containers are rotatingly transported in upright position just as in the preceding and succeeding process lines, the transport device for open-mouthed containers is structured to rotate, so that the transport device is prevented from being subjected to unreasonable excessive force, is worn very little and can be used for a very long time, reducing chances of dust adhering to the open-mouthed containers, so that this apparatus is suitably applied to the production line for beverage, for example.

BRIEF DESCRIPTION OF THE DRAWINGS

FIGS. 10A and 10B are schematic configuration diagrams showing the electron beam irradiation apparatus according to a ninth embodiment of the present invention.

FIGS. 11A to 11C are schematic configuration diagrams showing the electron beam irradiation apparatus according to a tenth embodiment of the present invention.

Figure 1:
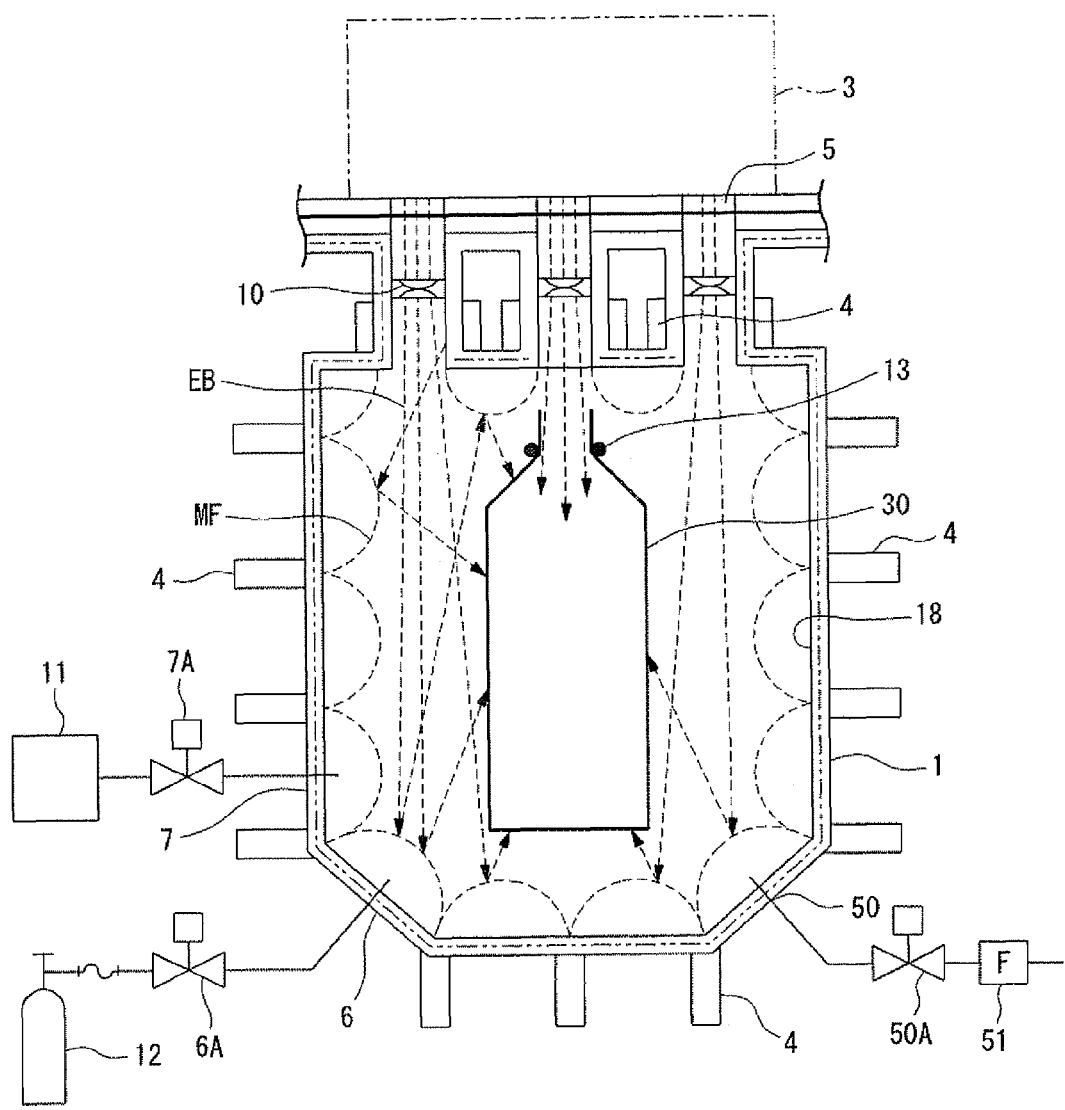
FIG. 1 is a schematic configuration diagram showing an electron beam irradiation apparatus according to a first embodiment of the present invention.

EXPLANATION OF NUMERALS 1, 21, 31, 60, 70 . . . Chamber (Irradiating chamber)
2 . . . Shielding material
3 . . . Electron beam generating room
3a . . . Electron beam unit (Electron beam irradiation means)
4, 19, 23 . . . Permanent magnet (Magnetic field generator)
5, 20 . . . Electron beam irradiation window
6 . . . Gas filling port
7, 24 . . . Gas suction port
8, 9 . . . Small compartment
10 . . . Electron deflector (Irradiation angle change means)
11, 69 . . . Vacuum pumping system
11E, 21E, 31E . . . Rotating transport device
12 . . . (Helium gas) cylinder
13 . . . Fixture
14 . . . Turntable
15 . . . Support axis
17 . . . Support base
18 . . . Chamber inner wall
21a . . . Object carry-in entrance
21b . . . Object carry-out exit
22 . . . Magnet support member
25 . . . Leak port
26 . . . Object rotating device
27 . . . Shield door
28 . . . Object transport device (Object transport means)
30 . . . Beverage container (Object)
31 . . . Sheet material (Object)
32 . . . Front gate valve
33 . . . Rear gate valve
34, 61, 75 . . . Front pressure adjusting chamber (Front sub room)
35, 62, 76 . . . Rear pressure adjusting chamber (Front sub room)
41 . . . Cylinder valve
42 . . . Manual valve
43 . . . Variable flow valve
44 . . . Filter
45 . . . Pressure gauge
50 . . . Air intake port
51, 52 . . . Filter
51a . . . Fan
53 . . . Bio filter
54 . . . Clean air generator (Clean air generator device)
63 . . . Outer frame
64 . . . Inner frame
65 . . . Holding device (Hand device)
66 . . . Partition wall
67, 68 . . . Pipe
69 . . . Vacuum pumping system
70 . . . Rotary table
71 . . . Magnetic field generating coil
72 . . . AC power supply
73 . . . Permanent magnet
74 . . . Yoke
75 . . . Timing belt
76 . . . Pulley
77 . . . Motor
78 . . . Cylinder
81 . . . 3-phase inverter
83 . . . Electromagnet
84 . . . Object receiving plate
86 . . . Cam device
87 . . . Gap roller
88 . . . Roller
90 . . . Slide moving device
91 . . . Receiving plate
92 . . . Connecting rod
93 . . . Bearing
94 . . . Connecting member
95 . . . Support arm
96 . . . Cam face (for magnetic field generator coil)
97 . . . Cam face (for Object receiving plate)
98 . . . Cam follower (for magnetic field generator coil)
99 . . . Cam follower (for object receiving plate)
100 . . . Transport device
118 . . . Drive device
145 . . . Electron beam deflector
146 . . . Protective plate
147 . . . Electron beam focusing device
148 . . . Cooling water pipe
149 . . . Clamp lever
150 . . . Rotating device
151 . . . Drive disc
152 . . . Drive roller
153 . . . Gap
EB . . . Electron beam
MF, MF2 . . . Magnetic field barrier

BEST MODE FOR CARRYING OUT THE INVENTION

Embodiments of the present invention will be described with reference to the drawings as occasion demands. In the following embodiments, examples of usage are shown in which an electron beam irradiation apparatus according to the present invention is applied to sterilize hollow beverage containers 30 of complicated shapes as objects, such as PET bottles for cold beverage, by using electron beam irradiation.

FIG. 1 is a schematic configuration diagram showing an electron beam irradiation apparatus according to a first embodiment of the present invention. Note that in FIG. 1, a nearly cylindrical irradiation chamber, which forms the main body of the electron beam irradiation apparatus, is shown in a cross section including the axis line.

As shown in FIG. 1, the electron beam irradiation apparatus includes a chamber 1 for irradiation with electron beams EB. This chamber 1 is a tight-sealed vessel of a pressure-resistant structure in a sufficient size to accommodate a beverage container, and formed in a nearly cylindrical shape with the axis line extending in the longitudinal direction. The chamber 1 is made of steel or stainless steel, and is covered, on its surfaces, with an X-ray shielding material, though this is not shown.

The chamber 1 is provided on its top with an electron beam irradiation means 3 for emitting electron beams towards electron beam irradiation area in the chamber. The electron beam irradiation means 3 has tightly attached to the top of the chamber 1 a plurality of (three in this example) of electron beam irradiation windows 5, and electron beams can be emitted into the chamber 1 through the electron beam irradiation windows 5. The electron beam irradiation means 3 can emit low-energy electron beams, and output of the electron beams is set to not more than 200 kV inside its main body. Circular electron deflectors 10 for emitting electrons at various angles into the chamber 1 are provided between the electron beam irradiation windows 5 and the chamber 1. In other words, the electron deflectors 10 serve as irradiation angle changing means capable of changing the irradiation angle of electron beams emitted from the electron beam irradiation means 3a.

At predetermined positions (on the outer wall of the chamber in this example) on the chamber 1, a plurality of permanent magnets 4 are arranged in such a way as to enclose the circumference of the electron beam irradiation area. Those permanent magnets 4, which can respectively generate magnetic fields in the electron beam irradiation area, are arranged at positions (corresponding to the predetermined positions mentioned above), at which the magnetic fields can be mutually joined together. The magnetic fields of the permanent magnets 4 form a cusp magnetic field. In other words, those permanent magnets 4 generate magnetic fields along the chamber inner wall to enclose a beverage container 30, which enables a cusp magnetic field to form a magnetic field barrier MF. Note that the above-mentioned magnetic field generating block corresponds to the permanent magnets 4. Further, the whole of the permanent magnets 4 correspond to the magnetic field barrier forming means.

The chamber 1 has a gas filling port 6, a gas suction port 7, and an air intake port 50 provided in the wall. The gas suction port 7 is connected to a vacuum pumping system 11 through a pipe and a gas release valve 7A. On the other hand, the gas filling port 6 is connected to a cylinder 12 for storage of helium gas through a gas intake valve 6A. The air intake port 50, which serves as a leak port, is connected to a pipe open to the room air, and an air intake valve 50A and a filter 51 are provided in the middle of this pipe. Therefore, the electron beam irradiation apparatus is adapted to be able to control the ambient atmosphere around a beverage container 30 in a predetermined state in the chamber 1. More specifically, the electron beam irradiation apparatus is able to control so that the internal atmosphere of the chamber is set to a predetermined state when the gas release valve 7A is opened, and the atmosphere is changed to a negative pressure when the air or gas in the chamber 1 is evacuated by the vacuum pumping system through the gas suction port 7. It is possible to supply helium whose specific gravity is light into the chamber 1 through the gas filling port 6 by opening the gas intake valve to replace the air. Moreover, it is possible to open the air intake valve 50A to introduce air on the room air side into the chamber 1 to make the inside of the chamber 1 open to the room air. If the gas intake valve GA, the gas release valve 7A and the air intake valve 50A are driven by electric signal or by pneumatic pressure and remotely-controlled valves are used for them, this is desirable because automatic control of the interior atmosphere of the chamber can be implemented.

Moreover, the electron beam irradiation apparatus includes an object carry-in entrance, not shown, which is provided in an openable/closable manner through the wall of the chamber 1. The electron beam irradiation apparatus further includes an object transport device (not shown) as an object transport means for transporting a beverage container 30 into and out of the chamber 1 through the object carry-in entrance. The object transport device includes a fixture 13 made of wire, for example. This fixture 13 enables a beverage container 30 to be transported while it is hold at the neck by the fixture. Thus, the beverage container 30 can be transported through the object carry-in entrance into the chamber 1 while it is held by this fixture 13 of the object transport device, and as shown in FIG. 1, the beverage container 30, held at the neck by the fixture 13 dangling in the chamber 1, so to speak, suspended in the air can be placed in a predetermined position in the chamber 1.

The operation and the effect of the electron beam irradiation apparatus will be described.

In the electron beam irradiation apparatus, a beverage container 30 held by the fixture 13 is carried by the object transport device through the object carry-in entrance into the chamber 1, and after the container is put in a predetermined position, the object carry-in entrance is closed. At this time, a magnetic field barrier MF by cusp magnetic field is generated along the inner wall 18 of the chamber in such a way as to enclose the beverage container 30 by a plurality of permanent magnets 4 installed in the chamber 1 (outer wall in this example). And, the beverage container 30 is held dangling by the fixture 13, as it were, suspended in the air.

The air in the chamber 1 is drawn out by the vacuum pumping system 11 through the gas suction port 7, and the inside of the chamber 1 is in a negative pressure state (in a low vacuum state of 0.5 MPa~0.1 Pa in this example). Depending on the kind of an object, a problem sometimes arises, such as odor or corrosion caused by ozone generated by irradiation of remaining oxygen molecules with electron beams EB, and even in such a case, helium whose specific gravity is light is filled through the gas filling port 6, as occasion demands, to replace the air. In this case, it may be arranged for helium at normal pressure to flow into the chamber at normal pressure.

Figure 2:
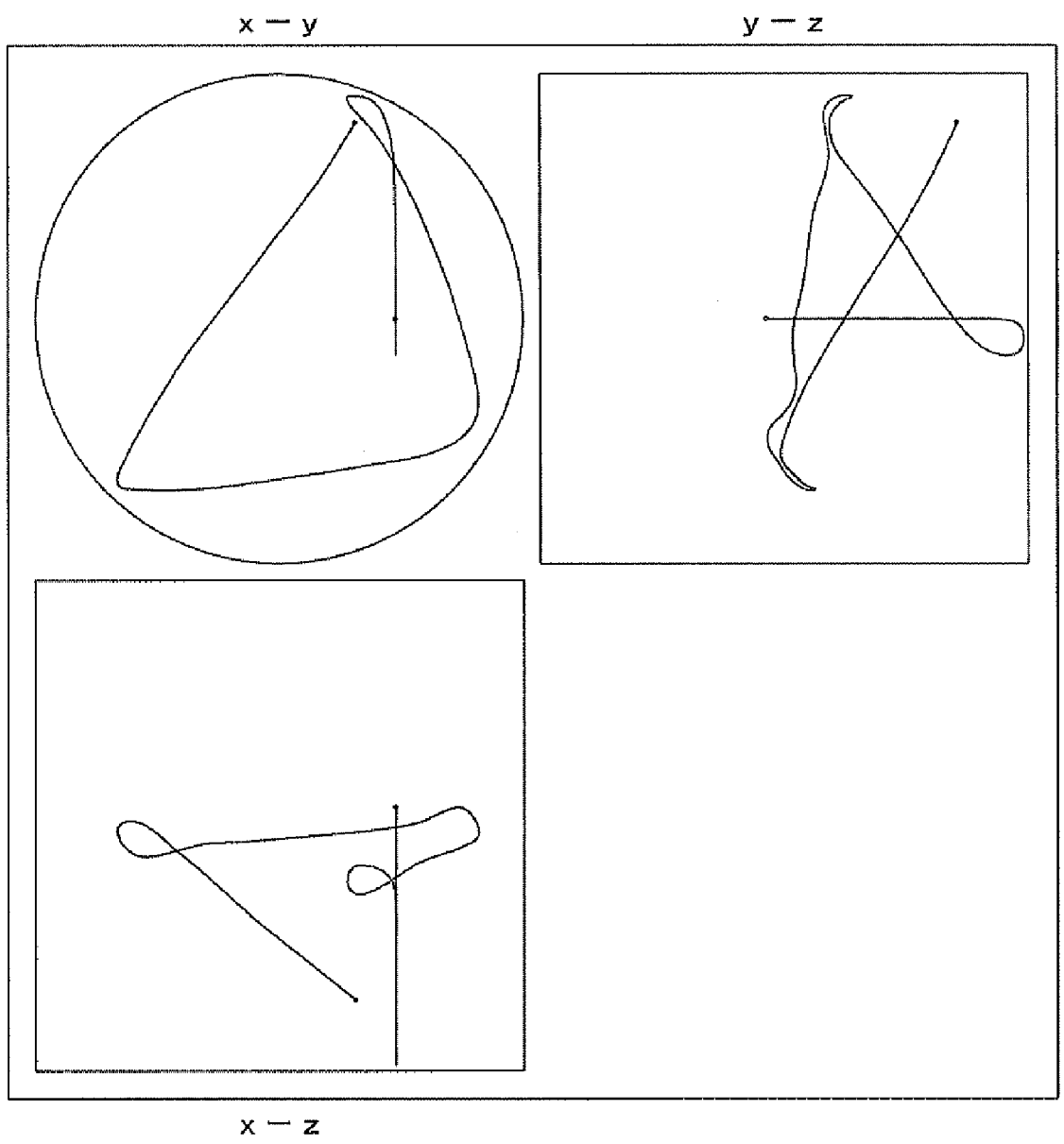
FIG. 2 is a diagram showing a simulation result of electron orbits in the magnetic field barrier.

While electrons are generated by the electron beam irradiation means and accelerated, and then the electron deflectors cause low-energy electron beams EB to plunge into the chamber 1 through electron beam irradiation windows 5. FIG. 2 shows simulation results of electron orbits in the magnetic field barrier FM. The set conditions for simulation in FIG. 2 are that the dimensions of the inside of the chamber 1 are $\phi$200 mm in diameter and 200 mm in height and for the magnets, neodymium magnets 8 mm in width and 40 mm in height (about 20 mm if the yoke is attached) are used. Its residual magnetic flux density is 13000 Gauss. As for predetermined position, the mounting pitch of the magnets (the pitch of cusp magnetic fields) is set at about 30 mm. The conditions for the atmosphere in the chamber 1 are that the pressure is at a low vacuum of 0.01 MPa and that the ambient gas is air. FIG. 2 shows calculated orbits when electrons with energy of 100 kV were emitted into the magnetic field barrier MF formed under the above settings and the electrons struck the weakest portions of the magnetic fields.

It is understood from FIG. 2 that in the magnetic field barrier MF, the electrons reflect randomly from the field barrier MR, that is, the electrons perform complicated motions, colliding disorderly and repeatedly with the magnetic field barrier of cusp magnetic fields formed in the space. Therefore, in the electron beam irradiation apparatus, the beverage container 30 can be uniformly irradiated with electron beams as the electron beams EB reflect randomly in the magnetic field barrier MF by the cusp magnetic field formed in the space of the chamber 1. Furthermore, the magnetic field barrier MF is formed in such a way of enclosing the beverage container 30 along the internal wall 18 of the chamber 1. Therefore, the electron beams EB do not collide with the structural block of the chamber 1. As a result, energy loss of the electron beams EB, which occurs at the internal wall 18 or the like in the chamber, can be reduced.

Also, in the electron beam irradiation apparatus, by the use of the electron deflectors 10, the electron means FB are made to fly into the chamber 1 at various angles from the electron beam irradiation windows 5. As a result, the electron beams EB emerging from the electron beam windows 5 rush disorderly into the chamber 1. Therefore, random reflection at the magnetic field barrier MF in the chamber 1 takes place more effectively, so that the beverage container 30 can be irradiated uniformly, without any irregularity.

In addition, in the electron beam irradiation apparatus, the air in the chamber 1 can be drawn out by the vacuum pumping system 11 from the gas suction port 7, and therefore the inside of the chamber 1 is put in a negative pressure (at a low vacuum of 0.05 MPa~0.1 Pa in this example). For this reason, the electron beams are placed in a condition that they can move more easily (lower energy loss) in the chamber 1. Therefore, a greater reduction of energy loss of the electron beams EB in the gas in the chamber accelerates the disorderly motion of the electron beams EB, and the beverage container can be irradiated with the electron beams more efficiently.

In the electron beam irradiation apparatus, either by filling helium whose specific gravity is light into the chamber 1, or by arranging for helium gas at normal pressure to flow into the chamber, it is possible to enable the electron beams BB to move more easily in the chamber 1 (with less energy loss). For objects with which a problem is likely to occur, such as odor or corrosion caused by ozone that is produced by collision of remaining oxygen molecules with electron beams EB, an arrangement that helium is used as the ambient gas.

An electron beam irradiation apparatus according to a second embodiment of the present invention will be described as follows.

Figure 3:
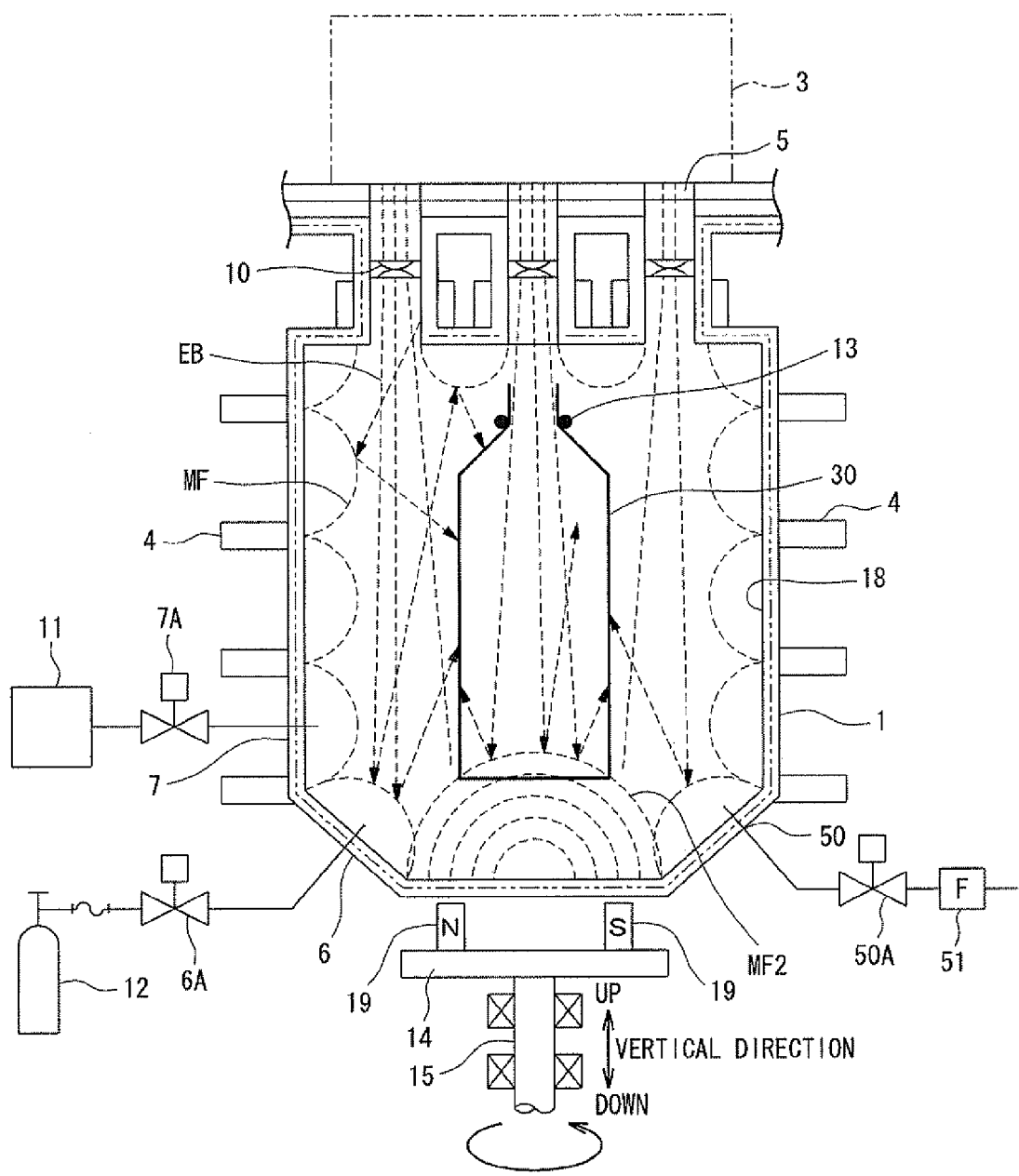
FIG. 3 is a schematic configuration diagram showing the electron beam irradiation apparatus according to a second embodiment of the present invention.

FIG. 3 is a schematic configuration diagram showing the electron beam irradiation apparatus according to a second embodiment of the present invention. Note that those configurations in the second embodiment which are identical with those of the first embodiment are designated by the same reference numerals and their descriptions are omitted where necessary.

In the second embodiment, a difference from the first embodiment is that the electron beams EB that have plunged into the chamber 1 are allowed to move disorderly, which is made possible by the distances and the directions of the arrangement of the permanent magnets as the magnetic field generators.

More specifically, in this electron beam irradiation apparatus, as shown in FIG. 3, a turntable 14 as the magnetic field barrier forming means is further added to the bottom of the chamber 1, which is a notable difference from the first embodiment. This turntable 14 is fixed to the upper end of the support axis 15, and the bottom end side of the support axis 15 is connected to the output spindle of a motor, not shown, through a coupling, not shown. An actuator, not shown, which enables the support axis 15 to move vertically, is further provided at the bottom end side of the support axis 15. Just like the above-described magnetic field barrier forming means, permanent magnets 19 to generate a cusp magnetic field are mounted at predetermined positions on the top of the turntable 14. The turntable 14, while it rotates, the intensity of the cusp magnetic field MF2 in the chamber 1 can be changed as the turntable's vertical height is adjusted by the actuator while the turntable rotates.

In the electron beam irradiation apparatus configured as described, under the condition that a beverage container 30 is placed in the chamber 1, the intensity of the cusp magnetic field MF2 can be changed by adjusting the vertical height of the turntable 14 while it rotates. Therefore, the electron beams EB emitted into the chamber 1 through the electron beam irradiation windows 5 in the middle of FIG. 3 are reflected by more random distances and directions in electron reflection than in the first embodiment. As a result, a beverage container 30 can be irradiated with electron beams EB uniformly (particularly at the bottom in this example).

An electron beam irradiation apparatus according to a third embodiment of the present invention will be described in the following.

Figure 4A:
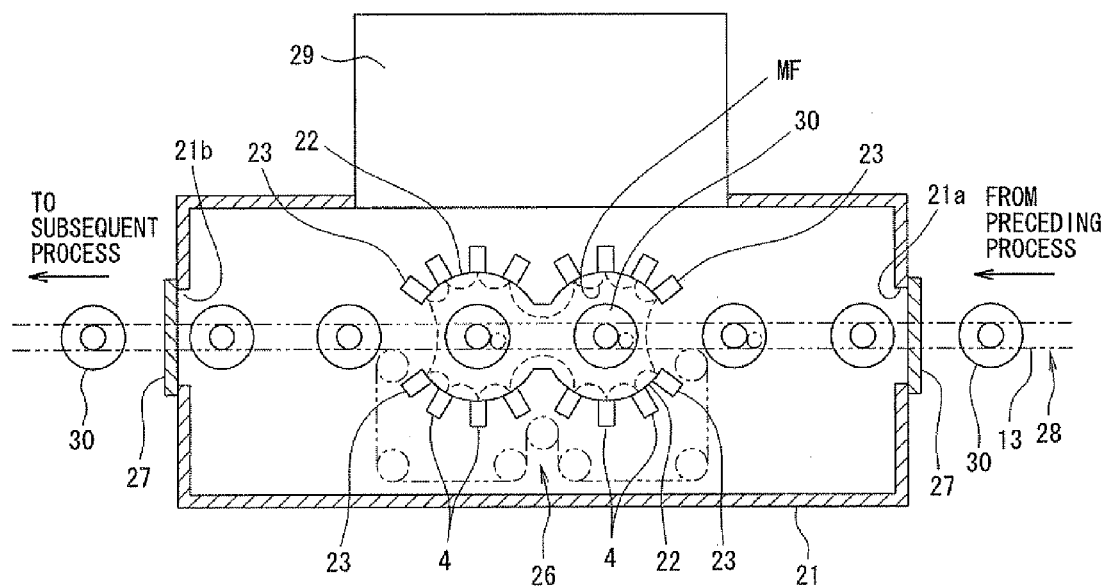
FIGS. 4A and 4B are schematic configuration diagrams showing the electron beam irradiation apparatus according to a third embodiment of the present invention.
Figure 4B:
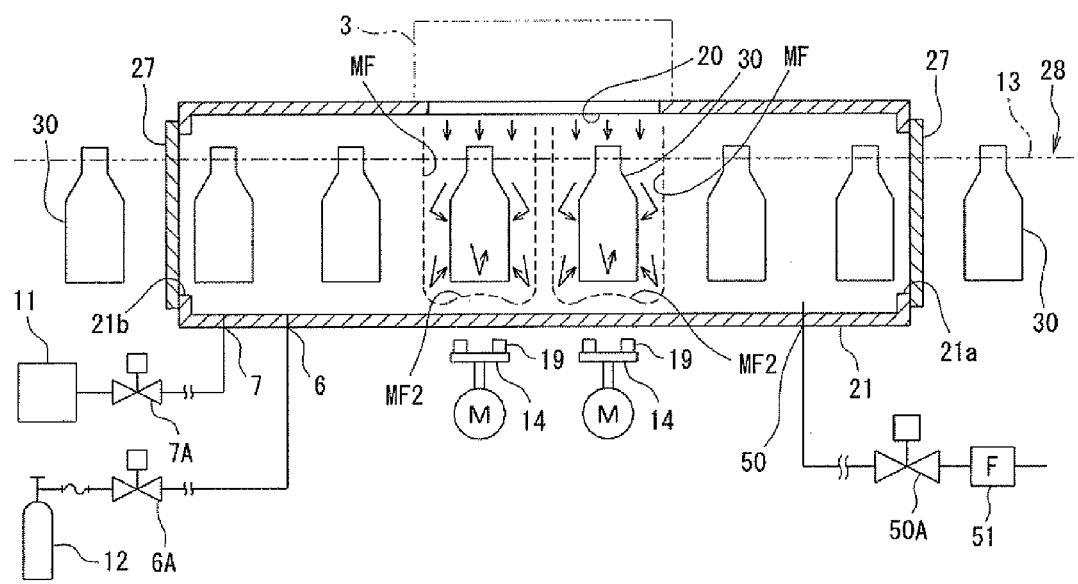

FIGS. 4A and 4B are schematic configuration diagrams showing an electron beam irradiation apparatus according to a third embodiment of the present invention. FIG. 4A is a front view and FIG. 4B is a plan view, each showing the irradiation chamber in cross section. Those configurations which are identical with those in the above-described embodiments are designated by the same numerals and their descriptions are omitted where necessary.

The third embodiment has the magnetic field barrier forming means of the first embodiment located within the chamber in a way to enclose the electron beam irradiation area, and this embodiment is particularly an example of an apparatus structure suitable for irradiation of a beverage container 30 with electron beams on a batch type production line.

This electron beam irradiation apparatus includes a box-shaped chamber 21 extending in the flow direction of the line as shown in FIGS. 4A and 4B. This chamber 21 is a tightly-sealed vessel of pressure-resistant structure like in the above embodiments, and a gas filling port 6, a gas suction port 7, and an air intake port 50 are provided through the wall of the chamber 21. The gas suction port 7 is connected to the vacuum pumping system 11 through a pipe and a gas release valve. The gas filling port 6 is connected to a helium gas storage cylinder 12 through a pipe and a gas intake valve GA. The air intake port 50, which works as a leak port, is connected to a pipe open to the room air side, and an air intake valve 50A and a filter 51 are provided in the middle of the pipe. Therefore, this electron beam irradiation apparatus can control the ambient atmosphere around the beverage container 30 in the chamber 21 in a predetermined state. In other words, in the third embodiment, the chamber 21 corresponds to the irradiation chamber described earlier.

An electron beam irradiation means 3 capable of emitting electron beams EB to a wide area in the chamber 21 is provided almost at the center of the top of the chamber 21. Two set of magnetic field barrier forming means, each including a turntable 14 and permanent magnets 19 placed on the turntable 14, like those used in the second embodiment, are arranged in the flow direction in positions corresponding to the electron beam irradiation area under the electron beam irradiation window 20 of the electron beam irradiation means, that is, substantially in the middle of the bottom of the chamber 21. The magnetic field barrier forming means like the one in the first embodiment is arranged in the chamber 21.

For more detail, the magnetic field barrier forming means in the chamber 21 is provided as the magnet support member 22, as shown in FIG. 4A, in a structure formed as if two chambers were arranged in a line in the production-flow direction after each chamber 1 of the first embodiment was cut in half along the longitudinal direction and arranged with their mating faces facing each other. The front and the rear open ends of the magnet support member 22 are facing the flow direction of beverage containers 30 and are arranged as the entrance and the exit in sizes for beverage containers to be able to come into and go out of the electron beam irradiation area. Permanent magnets 23 that can generate a cusp magnetic field are arranged around the entrance and the exit, and magnetic field barriers MF formed by mutual joining of cusp magnetic fields can be produced at the entrance an the exit. Therefore, in this electron beam irradiation apparatus, beverage containers 30 can pass through the electron beam irradiation area, and the electron beams within the electron beam irradiation area cannot get out of the magnetic field barrier FM in the electron beam irradiation area. The chamber 21 is configured to enclose an area as close to the magnet support member 22 and a beverage container 30 as possible. Numeral 29 in FIG. 4A denotes a power supply section of the electron beam irradiation means 3, and so on. In FIG. 4B, the magnetic field barrier forming means in the chamber 21 is not illustrated, except that an image of a magnetic field barrier MF (and MF2) that is formed is shown.

In the chamber 21, as shown in FIGS. 4A and 4B, an object carry-in entrance 21a and an object carry-out exit 21b are provided at the entrance side and the exit side in the flow direction of the production line for beverage containers 30. Shield doors 27 that can be opened at desired timing are provided at the object carry-in entrance 21a and the object carry-out exit 21b, respectively.

The electron beam irradiation apparatus includes an object transport device 28 for carrying a beverage container 30 from the object carry-in entrance 21a into the chamber 21 and discharging the beverage container 30 from the object carry-out exit 21b. This object transport device 28 includes a drive device, not shown, and the fixture 13 described above. Therefore, the object transport device 28 can operate the drive device, not shown, to cause the fixture 13 to hold a beverage container 30 by the neck and transport the object from the object carry-in entrance 21a to the carry-out exit 21b. At this time, as shown in FIG. 4B, in the same way as in the fourth embodiment, since a beverage container 30 is held dangling from the fixture 13 in the chamber 21, it can be moved and set at a predetermined position in the chamber 21 while it is suspended in the air. Incidentally, at the object carry-in entrance 21a and the object carry-out exit 21b, a retreat device, not shown, is provided which serves as a non-interference area to prevent interference with the shield door 27, and the fixture 13 and an beverage container 30 when the door 27 is opened or closed. The retreat device which can move the container to a non-interference area is installed both at the object carry-in entrance 21a and the object carry-out exit 21b.

The object transport device 28 includes an object rotating device 26 that rotates a beverage container 30 in the chamber 21 by means of a part of wire of the fixture 13, which is a component of the object transport device 28.

According to the electron beam irradiation apparatus configured as described, under the condition that both shield doors 27 are open at the object carry-in entrance 21a and the object carry-out exit 21b of the chamber 21, beverage containers 30 held by the fixtures 13 are moved by the object transport device 28 to a predetermined amount in the flow direction. Then, the shield doors 27 of the object carry-in entrance 21a and the object carry-out exit 21b are closed. In the same manner as in the described embodiments, the inside of the chamber 21 is placed in a negative pressure. When electron beams are emitted to an object, in which odor or corrosion occurs caused by ozone that is produced when electron beams hit the residual oxygen molecules, the air is replaced by helium whose specific gravity is light when necessary. Then, electron beams EB are emitted through the whole area of the wide irradiation window 20 into the electron beam irradiation area in the chamber 21. As a result, beverage containers 30 in the electron beam irradiation area are irradiated with electron beams EB. At this time, the electron beams emitted through the electron beam irradiation window 20 to the electron beam irradiation area randomly reflect off the magnetic field barriers MF and MF2, just like in the above-described embodiments, by means of the magnetic field barrier MF by the cusp magnetic field formed in the inside of the magnet support members 22 in the chamber 21 and the magnetic field barrier MF2 at the bottom of the chamber, so that the insides of the magnetic field barriers MF and MF2 can be turned into an electron shower state. Therefore, beverage containers 30 in the electron beam irradiation area can be irradiated with electron beams EB uniformly. After irradiation is performed with electron beams EB for a predetermined time, the inside of the chamber 21 is returned to an atmospheric pressure, the shield doors 27 of the object carry-in entrance 21a and the object carry-out exit 21b of the chamber 21 are opened.

By repeating the above-described process, the beverage containers 30 on the production line, which are supplied from the object carry-in entrance 21a of the chamber 21, pass through the electron beam irradiation area turned into an electron shower state by the magnetic field barriers MF and MF2 and the beverage containers that have been uniformly irradiated with electron beams EB are discharged one after another from the object carry-out exit 21b of the chamber 21.

According to this electron beam irradiation apparatus, the beverage containers 30 are rotated by the object rotating device 26 of the object transport device 28, so that beverage containers 30 can be irradiated with electron beams more efficiently.

According to this electron beam irradiation apparatus, the chamber 21 is configured to enclose only the small region of the beverage containers. Therefore, it is possible to minimize the region where X-ray shielding is provided and the ambient atmosphere around beverage containers is controlled to a specified state.

According to this electron beam irradiation apparatus, the shield doors 27 are provided, one to the object carry-in entrance 21a and the other to the object carry-out exit 21b. By this arrangement, it becomes easy to maintain the ambient atmosphere around the object in a predetermined state, such as to keep the chamber 21 in low vacuum or to replace to an atmosphere of a specific gas.

As has been described, according to the electron beam irradiation method and the electron beam irradiation apparatus of the embodiments shown above, beverage containers 30 as objects can be irradiated with electron beams uniformly, even with low-energy electron beams EB.

The electron beam irradiation method and the electron beam irradiation apparatus according to the present invention are not limited to those embodiments described, but may be embodied in various modifications as long as they do not depart from the spirit and scope of the invention.

For example, in the above-described embodiments, as an example of object, beverage containers 30 have been described, but this invention is not limited to this kind of object, and can be applied to, for example, food and beverage, water, pharmaceutical products, Chinese medicines, cosmetics, feeding stuffs, fertilizer, and packaging material for those objects. In other words, the present invention can be applied to objects ranging from complicated-shape three-dimensional objects to a flat film according to the kind and the shape of the object. For example, the present invention can be applied to uses in which unfolded paper sheet for milk-beverage containers is sterilized by electron irradiation. And, according to the present invention, when paper sheet mentioned above is irradiated with electron beams, the electron beams can be confined within the magnetic field barrier formed in such a way as to enclose the sheet material and the electron beams can be reflected at various angles, with the result that not only one side but also the other side of the sheet material can be irradiated in equal radiation doses on both sides with electron beams emitted from the electron beam irradiation means arranged in a position facing one side of the sheet.

In the foregoing embodiments, uses aimed to sterilize an object have been described as examples, but this invention is not limited to those embodiments, and may be applied to uses other than sterilization.

In the foregoing embodiments, regarding the irradiation chamber, description has been made of the tight-sealed chambers in a pressure-resistant structure capable of controlling the ambient atmosphere around the object, but the present invention is not limited to this type, and the chamber may be configured as an open-type irradiation chamber. Under this configuration, if a magnetic field barrier is formed by magnetic fields generated in such a way as to enclose an object and if the electron beams are made to reflect within the magnetic field barrier, it is possible to achieve the operation and the effect of the electron beam irradiation method and the electron beam irradiation apparatus according to the present invention. However, to reduce energy loss of the electron beams, the irradiation chamber is preferably configured to control the ambient atmosphere around the object to a predetermined state as in the embodiments discussed above.

In the embodiments discussed above, the magnetic field barrier has been described referring a case where the magnetic field barrier was formed by a cusp magnetic field, but the magnetic barrier of the present invention is not limited to this case, and may be formed by joining other magnetic fields together. The magnetic field barrier may be formed of mirror magnetic fields, for example.

In the embodiments discussed above, the magnetic field generators have been described in a case where they are formed permanent magnets, but the magnetic field generators are not limited to this type and may be formed by using electromagnets, circular coils, or permanent magnets, for example, or by a combination of them.

In the embodiments described above, description has been made of a case where the direction of the generated magnetic field can be changed by turning the turntable 14, but the present invention is not limited to this configuration and if the chamber is so configured as to change the direction in which the electron beams reflect within the magnetic field barrier, it becomes possible to effectively obtain the disorderliness of the direction in which the electrons reflect. For example, if a rotating magnetic field is formed in a suitable manner, the direction in which the electron beams reflect within the magnetic field barrier can be changed.

In the embodiments described above, description has been made of a case where the external shape of the chamber is previously decided according to the type of an object, but the chamber shape is not limited to this shape, and the chamber may be in a structure with a variable interior shape, which is changeable according to the shape of an object. To cite an example of such a chamber structure with variable interior shape, the chamber may be in a structure having sliding partition walls, which constitute the external shape of the chamber. Under this configuration, the chamber interior shape can be changed properly to suit the shape of an object. For this reason, an object can be irradiated with electron beams more efficiently and uniformly.

Further, in the embodiments described above, to show an example of control of the atmosphere of the chamber, the air is drawn out of the chamber 1 through the gas suction port 7 to keep the chamber internal atmosphere in a negative state (low vacuum state of 0.05 MPa to 0.1 P), and to address the problem of odor and corrosion caused by ozone that occurs when electron beams strike the remaining oxygen molecules, a helium gas 12 of light specific gravity is charged to replace air as necessity requires. However, the configuration for controlling the atmosphere in the chamber according to the present invention is not limited to what was mentioned above. In other words, to set the inside of the chamber 1 in a negative pressure, it is not limited to maintaining to, for example, a low vacuum state of about 0.05 MPa to 0.1 Pa, and it is possible to set the inside pressure at a high level of vacuum, and the higher the degree of vacuum, the lower is it possible to reduce the energy loss of electrons. And, the ambient gas in the irradiation chamber is preferably one or a plurality of gasses selected from air, oxygen, nitrogen, hydrogen, carbon dioxide, argon and helium. By selecting an ambient gas properly for the chamber according to the type of an object and the purpose of irradiation, the ambient atmosphere around the object can be controlled to a predetermined state. Even in an ambient gas at normal pressure, if a gas of light specific gravity, such as helium, is used as the ambient gas, the energy loss of electrons can be made smaller than in an ambient gas of high specific gravity, such as air. Even in an ambient gas at positive pressure, though this depends on the level of pressure, if a gas of light specific gravity such as helium is used as the ambient gas, the energy loss of electrons can be reduced to a sufficiently low level. When electron beams are emitted to an object in which a problem arises such as odor or corrosion caused by ozone that occurs when electron beams strike the remaining oxygen molecules, as a suitable inactive ambient gas, it is possible to use nitrogen gas or argon gas, for example, other than helium mentioned above, in view of its ability to lessen the energy loss of the electrons, it is particularly desirable to use helium gas of light specific gravity In the embodiments described above, description has been made of cases where the apparatus was used which was suited to irradiate beverage containers 30 with electron beams on the batch-type production line, but this invention is not limited to such cases, and may be applied to continuous production lines on which irradiation of objects with electron beams is performed.

Needless to say, the embodiments described above may be applied by selecting or combining their configuration as one thinks right.

A fourth embodiment of the present invention will be described with reference to the drawings where necessary.

In the following embodiments, examples of usage are shown in which an electron beam irradiation apparatus according to the present invention is applied to sterilize hollow beverage containers 30 of complicated shapes as objects, such as PET bottles for cold beverage, by using electron irradiation.

Figure 5:
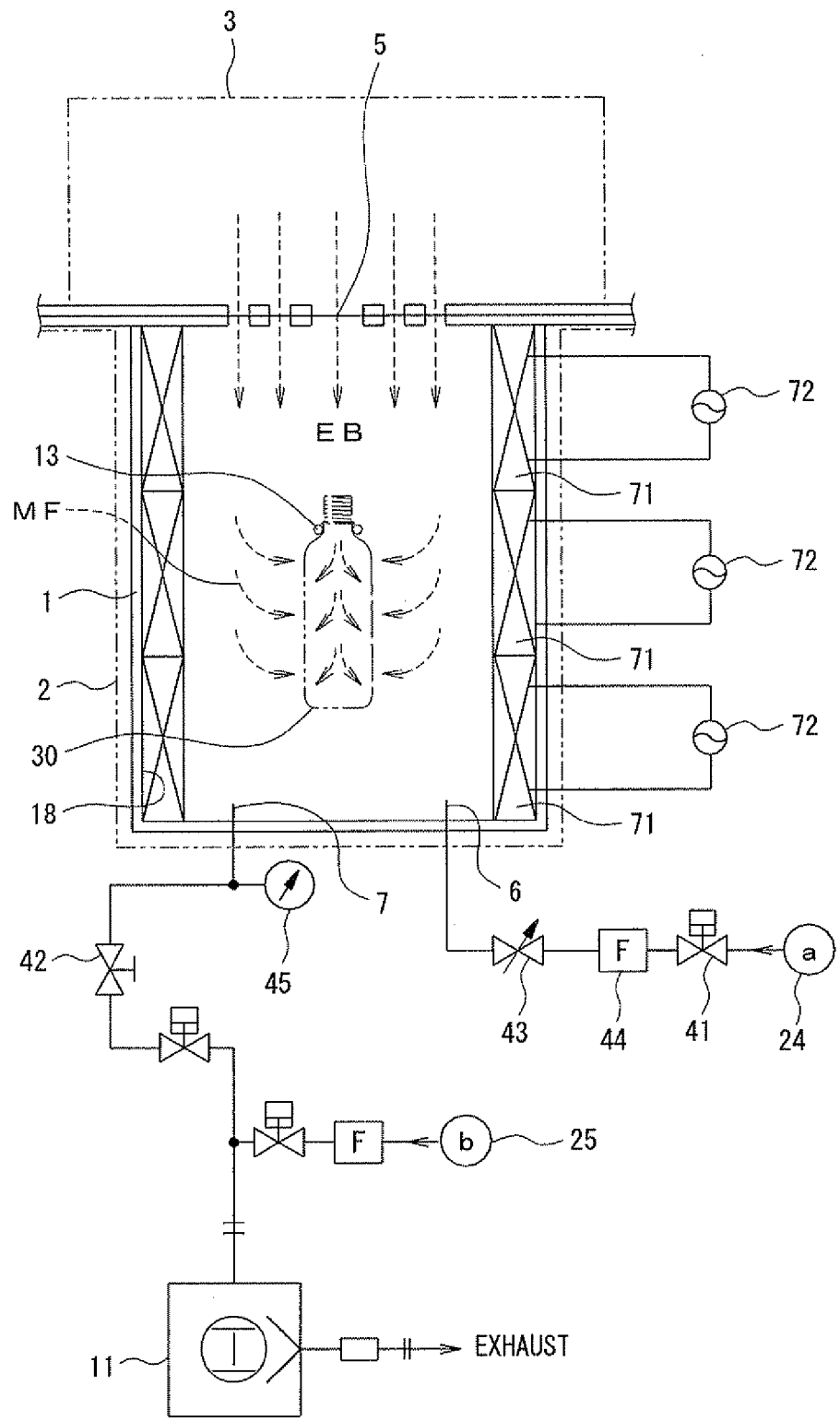
FIG. 5 is a schematic configuration diagram showing the electron beam irradiation apparatus according to a fourth embodiment of the present invention.

FIG. 5 is a schematic configuration diagram showing an electron beam irradiation apparatus according to a fourth embodiment of the present invention. A nearly cylindrical irradiation chamber, which forms the main body of the electron beam irradiation apparatus, is shown in a cross section including the axis line.

As shown in FIG. 5, this electron beam irradiation apparatus includes a chamber 1 in which irradiation with electron beams EB is performed. This chamber 1 is a tight-sealed vessel of a pressure-resistant structure in a sufficient size to accommodate a beverage container, and formed in a nearly cylindrical shape with the axis line extending in the longitudinal direction. The chamber 1 is made of steel or stainless steel, and is covered, on its surfaces, with a X-ray shielding material.

Mounted on the chamber 1 is an electron beam generating room 3, which includes an electron beam irradiation means emitting electron beams EB to the electron beam irradiation area in the chamber. The electron beam generating room 3 has a plurality of electron beam irradiation windows 5 (five in this case) attached to the top of the chamber 1, and can emit electron beams through the electron beam irradiation windows 5 into the chamber 1.

A plurality of magnetic field generating coils 71 in circular rings enclosing the electron beam irradiation area are arranged in predetermined positions on the wall (inner wall in this case) of the chamber 1. The magnetic field generating coils 71, constituting the magnetic field generating means, can generate a rotating magnetic field, which rotates about an object in the electron beam irradiation area when the coils 71 are supplied with electric current from the AC power supply supplies 72, respectively. The magnetic field generating coils 71 are stacked in three stages at the above-mentioned predetermined positions in such a way as to enclose beverage containers 30, and aligned in parallel with the axis line of beverage containers 30 in the chamber, and those magnetic field generating coils 71 each generate a rotating magnetic field. In other words, the plurality of magnetic field generating coils 71 generate the rotating magnetic fields in three stages along the inner wall 18 of the chamber in such a way as to enclose an object, and those coils are combined to form, as it were, a barrier by magnetic field. The magnetic field generating coils 71 correspond to the above-mentioned magnetic field generators. The intensity of the respective rotating magnetic fields can be changed by changing the effective values of AC current from the AC power supplies when power is supplied to the magnetic field generating coils 71. Timing of power supply is controlled so that the three-stage coils are switched over in the alignment sequence of the coils. Thus, by deflecting the electron beams EB to the upper, middle and lower portions of the beverage container 30 sequentially in the axial direction thereof, the beverage container 30 can be irradiated in a disorderly manner and evenly along its entire length.

The electron beam generating room 3 includes the electron beam irradiation means 3a capable of irradiating the inside of the chamber 1 with low-energy electron beams, and output of its main body is set to not less than 200 kV. Circular electron deflectors 10, not shown, for emitting electrons at various angles into the chamber 1 are provided between the electron beam irradiation windows 5 and the chamber 1. In other words, the electron deflectors 10 serve as irradiation angle changing means capable of changing the irradiation angle of electron beams emitted from the electron beam irradiation means 3a.

This electron beam irradiation apparatus is capable of controlling the ambient atmosphere around a beverage container 30 to a predetermined negative pressure necessary for a specified process in the chamber 1. This negative pressure is provided to make the inside of a container at a pressure value that enables electrons to sufficiently reach the bottom of a long and thin container, such as PET bottles, for example. More specifically, the electron beam generating room 3 and the chamber 1 are separated from each other by the electron beam irradiation windows 5 and their pressure can be controlled separately. Supposing the electron beam generating room 3 is decompressed to a high vacuum and this state is denoted as a first negative pressure, the inside of the chamber 1 is decompressed to a low vacuum state whose absolute pressure is higher than the first negative pressure and this state is denoted as a second negative pressure; and those two pressures are controlled individually.

To be more specific, as shown in FIG. 5, the gas filling port 6 and the gas suction port 7 are provided in the wall of the chamber 1. The gas suction port 7 is connected to the vacuum pumping system 11 through a pipe. On the other hand, the pressure of the chamber 1 can be controlled through the gas filling port 6 by supplying clean air or gas to the chamber 1 by control of the cylinder valve 41 through piping via a gas filling port 24 connected to a storage cylinder (not shown) containing a specified gas. A pressure control value can be adjusted, when necessary, according to a decided value based on electron range, irradiation process, and so on. In FIG. 5, numeral 25 denotes a leak port, 41 denotes a cylinder valve, 42 denotes a manual valve, 43 denotes variable flow valve, 44 denotes a filter, and 45 denotes a pressure gauge.

In this electron beam irradiation apparatus, the chamber 1 is controlled by negative pressure control to put its inside in the predetermined state mentioned above, and air or gas is drawn out of the chamber by the vacuum pumping system 11 through the gas suction port 7, the chamber inside is turned to a low vacuum state (0.05 MPa to 0.1 P in this case), and helium with light specific gravity can be filled into the chamber 1 through the gas filling port 6 in place of the air.

The electron beam irradiation apparatus includes an object carry-in entrance, not shown, which is provided through the wall of the chamber 1, and also includes an object transport device (not shown) as an object transport means to carry a beverage container 30 from the object carry-in entrance into the chamber 1. The object transport device includes a fixture 13 made of wire, for example. This fixture 13 is used to hold a beverage container 30 by the neck when it is transported. Therefore, the beverage container 30 is held by the fixture 13 of the object transport device and transported from the object carry-in entrance into the chamber 1, and as shown in FIG. 5, since the container 30 is held by the fixture 13 in the chamber, the container 30 can be set in a predetermined position while it is suspended in the air.

The operation and the effect of the electron beam irradiation apparatus is described as follows.

In the electron beam irradiation apparatus, a beverage container 30 is held by the fixture 13 and carried by the object transport device into the chamber 1, and after the container is set at a predetermined position, the object carry-in entrance is closed. At this time, the beverage container 30 is dangling from the fixture 13, as it were, suspended in the air in the chamber.

The air in the chamber 1 is drawn by the vacuum pumping system 11 through the gas suction port 7, thus setting the inside the chamber 1 in a low vacuum state (0.05 MPa to 0.1 Pa in this case). Helium gas with light specific gravity can be charged through the gas filling port 6 according to an irradiation process. A plurality of magnetic field generating coils 71 mounted along the wall surface of the chamber 1 (the inner wall in this case) generate rotating magnetic fields along the inner wall 18 in such a way as to enclose the beverage container 30.

The electron beam generating room 3 generates and accelerates electrons, which are passed through the electron deflector 10, and low-energy electron beams EB are emitted through the electron beam irradiation windows 5 into the chamber 1.

According to this electron beam irradiation apparatus, since the air in the chamber 1 is drawn out through the gas suction port 7 by the vacuum pumping system 11 and the chamber 1 is set in a low vacuum state (0.05 MPa to 0.1 Pa in this case), to put it differently, since the ambient atmosphere around the beverage container 30 is at a negative pressure, the emitted electron beams are inhibited from colliding with the ambient gas and therefore are in a state of easily moving in the chamber 1 (with reduced energy loss). Therefore, since the energy loss of the electron beams in the gas in the chamber 1 is reduced, the disorderly motion of the electron beams BB is accelerated. As a result, the beverage container 30 can be irradiated with electron beams EB more efficiently.

Since the electron beams reflect in disorderly, random manner within the rotating magnetic field generated by a plurality of magnetic field generating coils 71 in the inner space of the chamber 1, the beverage container 30 can be irradiated with electron beams uniformly. This rotating magnetic field is formed along the inner wall 18 of the chamber 1 to enclose the beverage container 30. Therefore, the electron beams EB hardly collide with the structural part of the chamber 1. Consequently, the energy loss of the electron beams EB at the inner wall 18 of the chamber can be lessened.

In this electron beam irradiation apparatus, by means of the electron deflector 10, the electron beams are made to plunge into the chamber 1 at various angles from the electron beam irradiation windows 5. Therefore, the electron beams emerging from the electron beam irradiation windows 5 plunge into the chamber 1 more disorderly. For this reason, random reflection within the rotating magnetic field in the chamber 1 takes place more effectively, so that the beverage container 30 in the chamber 1 can be irradiated with electron beams more uniformly without irregularity.

In this electron beam irradiation apparatus, either by filling helium whose specific gravity is light into the chamber 1, or by arranging for helium gas at normal pressure to flow into the chamber, it is possible to enable the electron beams EB to move more easily in the chamber 1 (with less energy loss). For objects with which a problem is likely to occur, such as odor or corrosion caused by ozone that is produced by collision of remaining oxygen molecules with electron beams EB, an arrangement that helium is used as the ambient gas.

In this electron beam irradiation apparatus, a plurality of magnetic field generating coils 71 are arranged to generate a plurality of rotating magnetic fields (three stages in the above case) in a range that encloses a beverage container 30. In this arrangement, since the plurality of rotating magnetic fields are joined together to form a barrier enclosing the whole of the beverage container, electrons are confined within the barrier, so that loss of energy can be inhibited desirably, and the beverage container 30 can be uniformly irradiated with electron beams EB.

In this electron beam irradiation apparatus, the plurality of rotating magnetic fields are individually generated by the plurality of magnetic field generating coils 71. Therefore, the disorderliness of the reflection directions of electrons can be obtained more effectively. As a result, the beverage container 30 can be irradiated with electron beams more efficiently. Since the beverage container 30 is irradiated with electron beams by moving the individually generated magnetic fields suitably in stages to the upper part, the middle part and the lower part of the container 30, the beverage container 30 can be irradiated evenly along its entire length.

In this electron beam irradiation apparatus, by changing the rotating directions of the rotating magnetic fields generated individually by the plurality of the magnetic field generating coils 71, the reflection directions of the electron beams in the rotating magnetic field can be changed. Therefore, the disorderliness of electron reflection directions can be obtained more effectively. As a result, more uniform irradiation of a beverage container 30 with electron beams can be obtained.

The electron beam irradiation apparatus according to a fifth embodiment of the present invention will be described in the following.

Figure 6A:
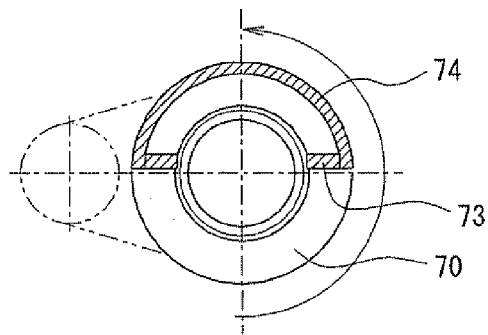
FIGS. 6A and 6B are schematic configuration diagrams showing the electron beam irradiation apparatus according to a fifth embodiment of the present invention.
Figure 6B:
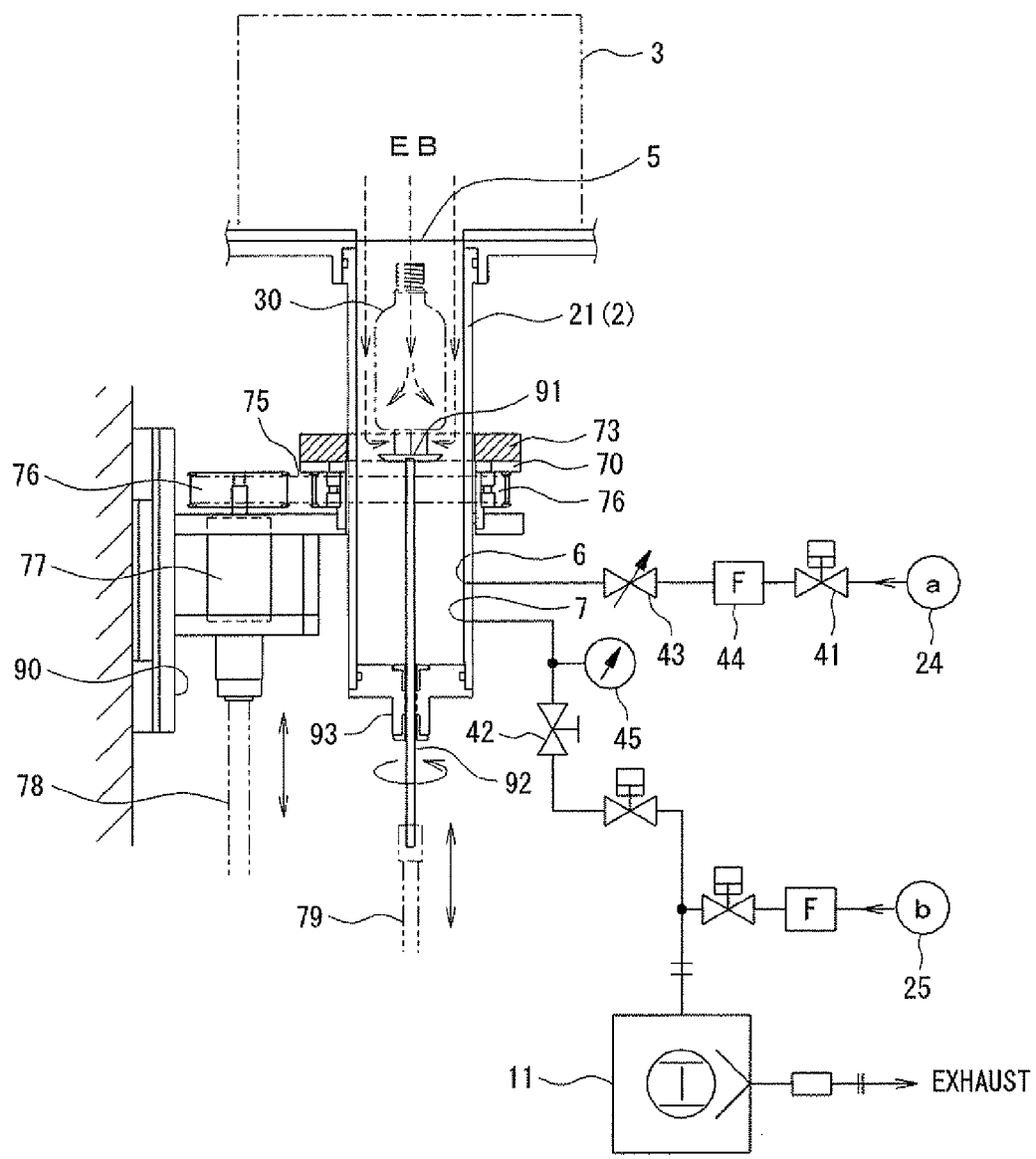

FIGS. 6A and 6B are schematic configuration diagrams showing the electron beam irradiation apparatus according to a fifth embodiment of the present invention. FIG. 6A is a front view and FIG. 6B is a plan view of a part of FIG. 6A, both of which are sectional views of the irradiation chamber. Those configurations which are identical with those in the fourth embodiment are designated by the same numerals and their descriptions are omitted.

In the fifth embodiment, the configuration differs from the fourth embodiment in that the magnetic field generator includes a plurality of permanent magnets arranged in a circular ring and a magnetic field generator rotating means for rotating the plurality of permanent magnets arranged in a ring about the central axis.

More specifically, the fifth embodiment is a case where the magnetic field corresponding to the rotating magnetic field is formed by rotating the generated magnetic field about the object, and its operational difference from the fourth embodiment is that the magnetic field corresponding to the rotating magnetic field is generated by rotating a plurality of permanent magnets arranged in a ring, by the magnetic field generator rotating means. In the fifth embodiment, the magnetic field generating means further includes an axial direction moving means for moving the magnetic field generator in the axial direction of the rotating magnetic field that is generated by the magnetic field generator.

To be more precise, a pair of permanent magnets 73 is arranged at diametrically opposite positions on the outer circumference of the chamber 21. The pair of permanent magnets 73 is connected at diametrically opposite ends through a yoke 74 and is capable of inhibiting magnetic leakage. The permanent magnets 73 and the yoke 74 are mounted and fixed to the top of the rotary table 70 capable of rotating about the central axis of the chamber 21. The rotary table 70 has teeth, such as a sprocket, formed on the outer peripheral surface thereof. The outer peripheral surface is linked to a pulley 76 through a timing belt 75, and the pulley 76 is linked to the output spindle of a motor 77; therefore, when the motor 77 is switched on, the rotary table 70 is driven to rotate about the central axis of the chamber 21. As the permanent magnets 73 and the yoke 74 on the rotary table 70 rotate, a rotating magnetic field can be generated along the inner wall of the chamber 21.

As shown in FIGS. 6A and 6B, the structural block that generates the rotating magnetic field is supported on the wall surface through a slide moving device 90 provided with a linear guide arranged to be able to move in the axial direction of the chamber 21. In FIGS. 6A and 6B, a cylinder 78 having a shank movable in the axial direction of the chamber 21 is attached to the lower end of the motor 77. The lower end of the motor is connected to the shank of the cylinder 78. The structural block that generates the rotating magnetic field can move in the axial direction of the chamber 21 when the cylinder 78 is driven reciprocally.

In this electron beam irradiation apparatus, another difference from the preceding embodiment is that as a means for forming a magnetic field corresponding to the rotating magnetic field, a mechanism for reciprocal drive and rotation drive is provided at the bottom of the chamber 21 as shown in FIGS. 6A and 6B.

In other words, in this embodiment, as described above, an additional arrangement is made to rotate and vertically move a beverage container 30, which means that there is substantially added another arrangement for forming the rotating magnetic field. By this arrangement, since the object is rotated within the rotating magnetic field, it becomes possible to form a magnetic field rotating relative to the "rotating" object.

More specifically, as shown in FIGS. 6A and 6B, a beverage container 30 is placed on a receiving plate 91. This receiving plate 91 is adapted as a turntable. To be more precise, the bottom side of the receiving plate 91 is connected to one end of a connecting rod 92. The portion adjacent to the other end side of the connecting rod 92 is supported in a vertically slidable state by a bearing 93 having an air-tight seal, and the end side extends beyond the chamber 21. The extending end is attached to the shank of the cylinder 79 through a coupling. The connecting rod 92 is provided with a rotating mechanism connected to the output spindle of the motor through a timing belt and other parts 75, 76, and 77, and is rotatable about the axis.

The receiving plate 91 holding a beverage container 30 can slide in the axial direction of the chamber 21 while the cylinder 79 is moved reciprocally and can rotate as the connecting rod 92 is rotated by a rotating mechanism, including a motor, not shown. Therefore, a rotating magnetic field that rotates relative to the object that rotates within the rotating magnetic field can be obtained. In other words, in an electron beam irradiation apparatus configured as described, when a beverage container 30 is inserted in the chamber 21, by adjusting the height in the vertical direction while the receiving plate 91 is rotated, a rotating magnetic field can be formed. Therefore, above all, the electron beams EB emitted into the chamber 21 through the electron beam irradiation window 5 at the center of FIGS. 6A and 6B reflect with random reflection distances and directions as in the first embodiment. Therefore, the beverage container 30 can be irradiated evenly with electron beams EB.

Even when the above-mentioned permanent magnets 73 and the yoke 74 are not moved, when the position of the beverage container 30 in the axial direction is moved vertically and its circumferential direction is changed by rotating it by the mechanism for reciprocal drive and rotation drive attached to the bottom of a beverage container 30, the effect is substantially the same as in the rotating magnetic field in the fourth embodiment. Therefore, the electron beams emitted into the chamber 21 by the rotating magnetic field can be allowed to move disorderly and the beverage container 30 can be irradiated evenly with electron beams EB.

If a rotating magnetic field according to the present invention can be substantially formed, the configurations exemplified above can be combined in a suitable form. For example, without moving the permanent magnets 73 and the yoke 74, a beverage container 30, which is being rotated, may be moved vertically, or without moving the beverage container 30, the permanent magnets 73 and the yoke 74, which are being rotated, may be moved vertically. Or, the permanent magnets 73 and the yoke 74 may be moved vertically and the beverage container 30 may be moved vertically.

When the configuration of the fifth embodiment is applied to a continuous production line, the configuration may be adapted depending on an irradiation process, in such a way that permanent magnets 73 are arranged by the side of the line on which objects, such as beverage containers 30, are transported or that the objects are passed through the electron beam irradiation area while they are rotated on their axes.

The electron beam irradiation apparatus according to a sixth embodiment of the present invention will be described as follows.

Figure 7:
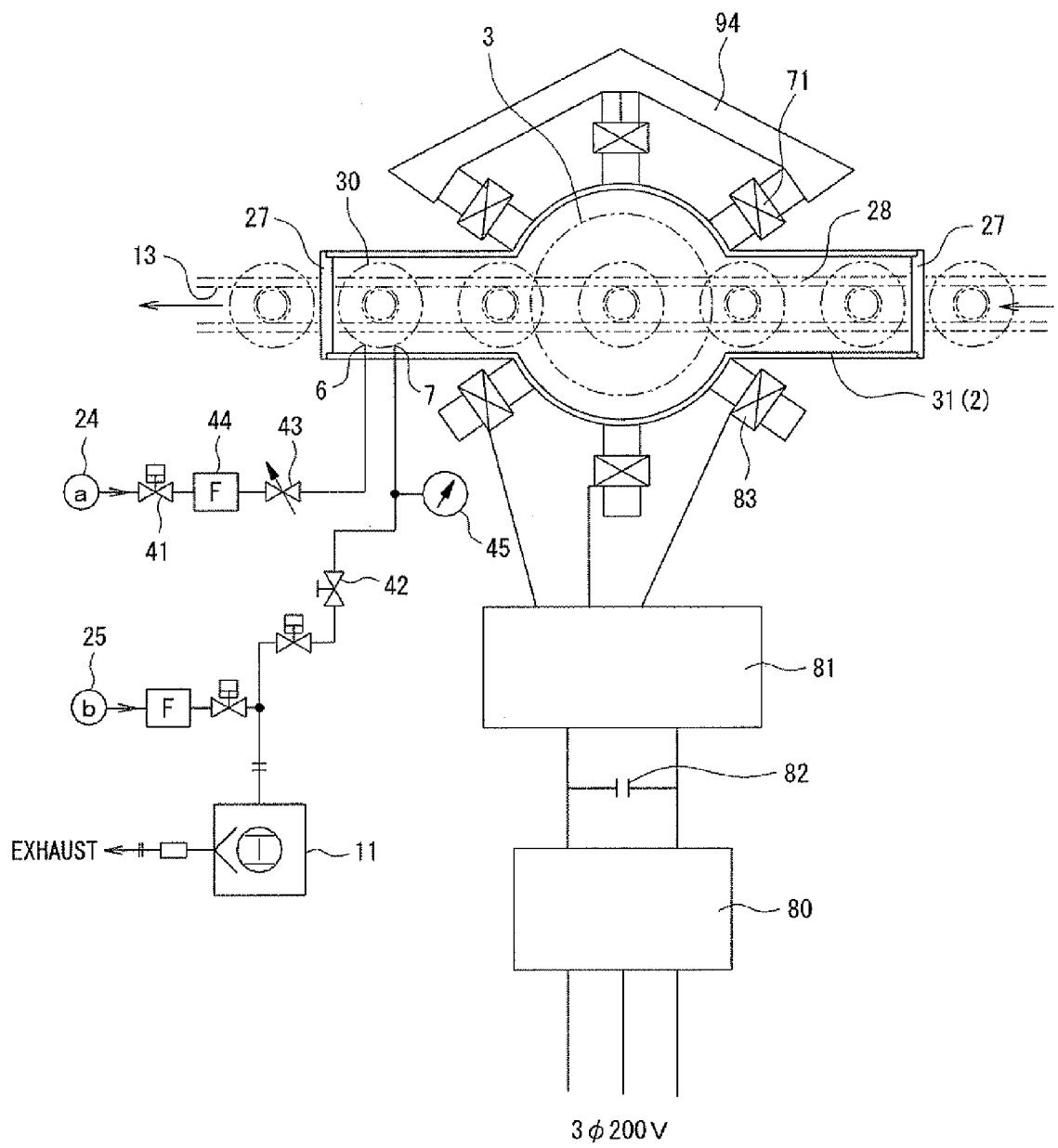
FIG. 7 is a schematic configuration diagram showing the electron beam irradiation apparatus according to a sixth embodiment of the present invention.

FIG. 7 is a schematic configuration diagram showing in plan view the electron beam irradiation apparatus according to a sixth embodiment of the present invention, in which the chamber 31 as an irradiation chamber is illustrated in a cross section. Configurations which are identical with those of the embodiments described above are designated with the same minerals and their descriptions are omitted where considered obvious.

The sixth embodiment includes a magnetic field generating means in the chamber 31 including the electron beam irradiation area, which is a case where the apparatus structure is adapted to be particularly suitable for irradiation of beverage containers 30 with electron beams on a batch-type production line.

As shown in FIG. 7, this electron beam irradiation apparatus includes a chamber 31. This chamber 31 has an electron beam irradiation area in an almost round shape as seen in plan view at the center in the flow direction of the line in FIG. 7. A rectangular box-shaped transport path, the inside of which there is a space communicating to both sides of the round block in the flow direction of the line. Like in the embodiments described previously, this chamber 31 is a tight-sealed vessel of a pressure-resistant structure, and a gas filling port 6 and a gas suction port 7 are provided through the wall of the chamber 31 and necessary piping is installed. To be more precise, the gas suction port 7 is connected to the vacuum pumping system 11 through piping. The pressure of the chamber 1 can be controlled through the gas filling port 6 which supplies clean air or gas to the chamber 1, under operation control by the cylinder valve 41, through piping via a gas filling port 24. This electron beam irradiation apparatus is capable of controlling the ambient atmosphere around the beverage container 30 to a predetermined negative pressure in the chamber 31.

An electron beam generating room 3 capable of emitting electron beams EB to a wide area in the chamber 31 is provided almost at the center of the top of the chamber 31, which is in a round shape as seen in a plan view. A magnetic field generating means is provided at a position, which corresponds to the electron beam irradiation area, below the electron beam irradiation window of the electron beam irradiation means, in the circumferential area almost in the middle of the chamber 31. The chamber 31 is formed in such a way as to enclose only the area as close to a beverage container as possible.

The magnetic field generating means has a plurality of electromagnets 83 arranged as the magnetic field generators. To be more specific, the electromagnets 83 are arranged at six positions equally spaced in the circumferential direction along the periphery of the chamber 31 in a round shape.

The electromagnets 83 arranged at six positions are connected with their adjacent iron cores joined together through a connecting member. The magnetic field generating coils 71 of the electromagnets 83 are connected to a 3-phase inverter 81 so that the electromagnets can be energized. FIG. 7 shows only one group of three magnets 83 on the back side in the picture, connected to a connecting member 94 and only one group of three electromagnets on the front side in the picture, connected to the 3-phase inverter. In FIG. 7, numeral 82 denotes a capacitor, and 80 denotes a converter. By this configuration, in the magnetic field generating means, by energizing the electromagnets 83 at six positions by a 3-phase converter 81, a rotating magnetic field can be generated. Therefore, by forming a magnetic field that encloses a beverage container 30 around the electron beam irradiation area, that is, by forming a barrier made up of, so to speak, a fast-rotating magnetic field, it becomes possible to form a magnetic field corresponding to the rotating magnetic field.

In this example, by changing an effective value of an output current (or an output voltage) by the 3-phase inverter 81, the intensity of the magnetic field can be changed, and by changing an output frequency, the number of revolutions of the magnetic field can be changed. To take an example of a way of connection between the magnetic field generating coils 71 and the 3-phase inverter 81, with regard to the magnetic field generating coils 71 of the electromagnets 83 at the six positions, the three pairs, across the round block of the chamber 31, of the magnetic field generating coils 71 are connected to the three phases of output of the 3-phase inverter 81. In this example, as the configuration of magnetic poles, a six-pole configuration that provides the electromagnets 83 at six positions around the round block of the chamber 31 is shown, but the pole configuration is not limited to this six-pole type. In this example, a configuration that the electromagnets of the magnetic field generator are energized by a 3-phase AC current is shown, but the AC power supply configuration for energizing is not limited to by a 3-phase AC current, and a multiple-phase AC current larger than the 3-phase may be used.

In this electron beam irradiation apparatus, the object transport device 28 as the object transport means is provided to carry a beverage container 30 from the object carry-in entrance 21a (the shield door on the right side of FIG. 7) into the chamber 31 and discharge the beverage container 30 from the object carry-out exit 21b (the shield door on the left side in FIG. 7). This object transport device 28 includes a drive device, not shown and a fixture 13 same as the one described above. The object transport device 28 is configured such that by actuating the drive device, not shown, the beverage container 30 is held at its neck with the fixture 13 and transported and can be carried in and out through the left and the right shield doors 27 as the object enters and exits. At this time, as in the first embodiment, a beverage container 30, while it is held dangling by the fixture 13, as it were, suspended in the air, can be set in a predetermined position in the chamber 31. Incidentally, at the object carry-in entrance 21a and the object carry-out exit 21b, a retreat device, not shown, is provided which serves as a non-interference area to prevent interference with the shield door 27, and the fixture 13 and an beverage container 30 when the door 27 is opened or closed. The retreat device which can move the container to a non-interference area is installed both at the object carry-in entrance 21a and the object carry-out exit 21b.

The object transport device 28 includes an object rotating device 26 that rotates a beverage container 30 in the chamber 21 by means of a part of wire of the fixture, which is a component of the object transport device 28.

According to the electron beam irradiation apparatus configured as described, under the condition that both shield doors 27 are open at the object carry-in entrance and the object carry-out exit of the chamber 31, beverage containers 30 held by the fixtures 13 are moved by the object transport device 28 to a predetermined amount in the flow direction. Then, the shield doors 27 of the object carry-in entrance 21a and the object carry-out exit 21b are closed. In the same manner as in the described embodiments, the inside of the chamber 31 is placed in a low vacuum state. When electron beams are emitted to an object, in which odor or corrosion occurs caused by ozone that is produced when electron beams hit the residual oxygen molecules, the air is replaced by helium whose specific gravity is light when necessary. Then, electron beams EB are emitted through the irradiation window 20 into the electron beam irradiation area in the chamber 31. As a result, beverage containers 30 in the electron beam irradiation area are irradiated with electron beams EB. At this time, the electron beams emitted through the electron beam irradiation window to the electron beam irradiation area randomly reflect off the rotating magnetic field made up of the magnetic fields formed by the electromagnets 83 in the chamber 31, just like in the above-described embodiments, so that the inside of the rotating magnetic field can be turned into an electron shower state. Therefore, beverage containers 30 in the electron beam irradiation area can be irradiated with electron beams EB uniformly. After irradiation is performed with electron beams EB for a predetermined time, the inside of the chamber 31 is returned to an atmospheric pressure, the shield doors 27 of the object carry-in entrance and the object carry-out exit of the chamber 31 are opened.

By repeating the above-described process, the beverage containers 30 on the production line, which are supplied from the object carry-in entrance of the chamber 31, pass through the electron beam irradiation area turned into an electron shower state by the rotating magnetic field and the beverage containers that have been uniformly irradiated with electron beams EB are discharged one after another from the object exit of the chamber 31.

In particular, as shown in FIG. 7, in this electron beam irradiation apparatus, it is possible to, as it were, vertically separate the plurality of electromagnets around the electron beam irradiation area, arrange beverage containers 30 between the separated electromagnets 83 in such a manner that the containers 30 can pass through, and form a magnetic field enclosing a container 30. Therefore, this sixth embodiment is suitable for a case where a rotating magnetic field is formed on a line for a batch or a continuous transport of beverage containers.

More specifically, the magnetic field generating means around the chamber 31 are separated in half in the middle of the chamber and arranged on both sides of the flow direction with their mating faces facing each other. Two-half blocks of the electromagnets 83 have their open ends facing in the flow direction of beverage containers 30, and the open ends are located as the entrance and the exit through which beverage containers 30 can go into and come out of the electron beam irradiation area.

Thus, this electron beam irradiation apparatus can be configured such that the beverage containers 30 can pass through the electron beam irradiation area, whereas the electrons in the electron beam irradiation area can hardly go out of the rotating magnetic field in the electron beam irradiation area.

As shown in FIG. 7, at the chamber 31, the shield doors 27 that can open and close at desired timing are provided at the entrance side and the exit side in the flow direction of the production line of beverage containers 30.

According to the electron beam irradiation apparatus, the chamber 31 is configured in such a way as to enclose only the area of a beverage container 30 and its close vicinity. Therefore, it is possible to minimize the region where X-ray shielding is provided and the ambient atmosphere around beverage containers is controlled to a specified state.

According to this electron beam irradiation apparatus, the shield doors 27 are provided, one to the object carry-in entrance 21a and the other to the object carry-out exit 21b. By this arrangement, it becomes easy to maintain the ambient atmosphere around the object in a predetermined state, such as to keep the chamber 21 in low vacuum or to replace to an atmosphere of a specific gas.

Another example of a case where a line is configured for a batch or a continuous transport of beverage containers 30 will be described with reference to the electron beam irradiation apparatus according to a seventh embodiment of the present invention.

Figure 8A:
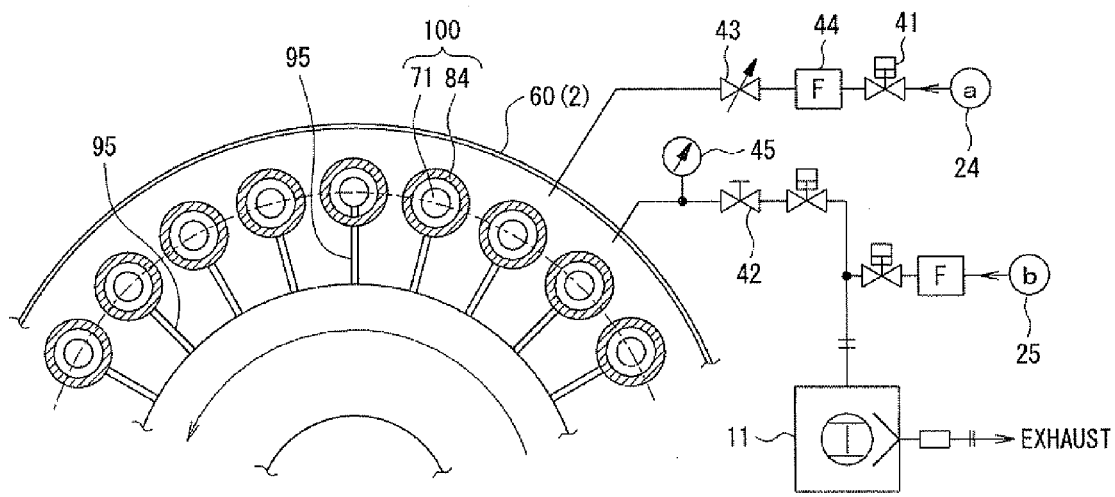
FIGS. 8A to 8C are schematic configuration diagrams showing the electron beam irradiation apparatus according to a seventh embodiment of the present invention.
Figure 8B:
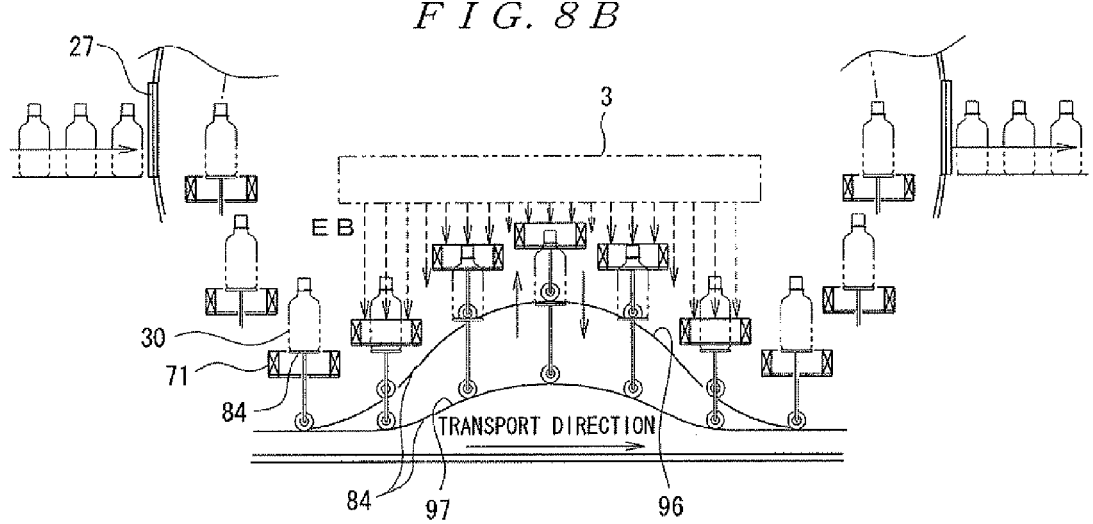
Figure 8C:
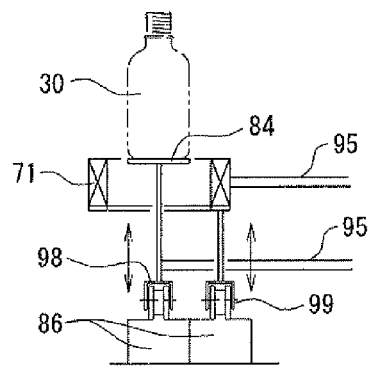

FIGS. 8A to 8C are schematic configuration diagrams showing the electron beam irradiation apparatus according to the seventh embodiment of the present invention, in which FIG. 8A is a half of the upper side of the electron beam irradiation apparatus as seen in a plan view, FIG. 8B is a development view showing beverage containers in the transport direction, and FIG. 8C is a view, on an enlarged scale, of the rotating magnetic field generating block and a cam device that moves an object up and down. Those configurations identical with those in the embodiments described above are designated by the same numerals and their descriptions are omitted where possible.

As illustrated, in this process chamber 60, the internal space used as the electron beam irradiation area is formed in a circular ring, and in this electron beam irradiation area, a plurality of transport devices 100, each transport device having a magnetic field generating coil 71 and an object receiving plate 84 in one body, are mounted along a circular ring form in the electron beam irradiation area.

A rotating device, not shown, is mounted in the center of the circular-ring process chamber 60. This rotating device has a configuration same as the turntable in the embodiments described, and is rotatable at a predetermined angular speed about the central axis of the process chamber 60. The plurality of the transport devices 100 are mounted around the rotating device, and equally spaced in almost circumferential direction. Each rotating device 100 has its magnetic field generating coil 71 and object receiving plate 84 connected through its support arm 95 to the outer circumference of the rotating device. The connection parts are connected through a vertically-slidable slide guide device. The transport devices 100 are restricted in circumferential movement, but are able to move vertically. And, the plurality of the transport devices 100 in their entirety can rotate along the circular-ring process chamber 60.

As shown in a development view in FIG. 8B, the magnetic field generating coil 71 and the object receiving plate 84 are connected to a cam device 86, and they go up and down independently of the other in the electron beam irradiation area to move the whole of a beverage container 30 as an object in the longitudinal direction of the container. To be more specific, provided at the bottom of each transport device 100 is either a cam follower 98 or 99, which follows a cam face 96 or 97, is connected through a connecting rod to the magnetic field generating coil 71 or the object receiving plate 84. As the cam followers 98 and 99 of the transport device 100 follow the cam faces 96 and 97 of the cam device 86, which is provided under the cam followers, the cam followers 98 and 99 respectively can move for specified lifting heights in the vertical direction. Incidentally, the cam face 96 is the cam face for the magnetic field generating coils, while the cam face 97 is the cam face for the object receiving plates 84.

According to the seventh embodiment, the configuration described above is suitable for a case where a rotating magnetic field is formed on a line for a batch or a continuous transport of beverage containers 30. In FIGS. 8A to 8C, an example of configuration is shown, in which a magnetic field generating coil and a beverage container 30 are moved together in vertical direction, but it may be arranged that only one of them is moved vertically. Though description has been made of a case where magnetic field generating coils 71 are adopted, but the magnetic field generation block may be configured by permanent magnets. Which to choose may be decided suitably according to an irradiation process with electron beams. In addition, a suction pad or an air clamp for holding a beverage container 30 may be provided on the top surface of the object receiving plate 84.

As has been described, uniform electron beam irradiation of a beverage container 30 as an object can be achieved also by the electron beam irradiation method and the electron beam irradiation apparatus according to the fourth to seventh embodiments or by using low-energy electron beams EB.

The electron beam irradiation method and the electron beam irradiation apparatus are not limited to the fourth to seventh embodiments, and can be embodied in various modifications and alterations without departing from the scope and the spirit of the present invention.

For example, in the fourth to seventh embodiments, description has been made using beverage containers 30 for objects. This invention can be applied to other objects, such as food and drink, water, pharmaceutical products, Chinese medicines, cosmetics, feeding stuffs, fertilizer, fertilizer or packaging material for those products. In other words, the present invention can be applied to objects ranging from complicated-shape three-dimensional objects to a flat film according to the kind and the shape of the object. For example, the present invention can be applied to uses in which unfolded paper sheet for milk-drink containers is sterilized by electron irradiation. According to the present invention, when sheet-form material is irradiated with electron beams, by passing the sheet-form material through a rotating magnetic field, the sheet material can be irradiated on both sides and at the end portions with electron beams uniformly and efficiently by an electron shower generated within the rotating magnetic field.

In the fourth to seventh embodiments, uses in which an object is sterilized have been described, but the present invention is not limited to those uses and may be applied to uses other than sterilization.

In the fourth to seventh embodiments, as to the irradiation chamber, description has been made of an example that the chamber is a tight-sealed vessel of a pressure-resistant structure in which the ambient atmosphere around the object can be controlled to a specified state, but the chamber is not limited to this type and may be an open type. However, from a viewpoint of reduction of energy loss of the electron beams, as in the above-described embodiment, it is desirable to use an irradiation chamber capable of controlling so that the ambient atmosphere around the object to a specified state, set the process chamber to a negative state, form a rotating magnetic field made by magnetic fields generated to enclose the object, and cause the electron beams emitted to the object to reflect within the rotating magnetic field.

In the fourth to seventh embodiments, description has been made of cases where the magnetic field generator is formed by a permanent magnet, electromagnets and circular coils, but the present invention is not limited to this configuration, and the magnetic generator may be formed by electromagnets, circular coils or a permanent magnet or a combination of them, for example.

In the embodiments described above, description has been made of a case where the external shape of the chamber is previously decided according to the type of an object, but the chamber shape is not limited to this shape, and the chamber may be in a structure with a variable interior shape, which is changeable according to the shape of an object. To cite an example of such a chamber structure with variable interior shape, the chamber may be in a structure having sliding partition walls, which constitute the external shape of the chamber. Under this configuration, the chamber interior shape can be changed properly to suit the shape of an object. For this reason, an object can be irradiated with electron beams more efficiently and uniformly.

In the fourth to seventh embodiments, to show an example of control of the atmosphere of the chamber, the air is drawn out of the chamber 1 through the gas suction port 7 to keep the chamber internal atmosphere in a negative state (low vacuum state of 0.05 MPa to 0.1 P), and to address the problem of odor and corrosion caused by ozone that occurs when electron beams strike the remaining oxygen molecules, a helium gas 12 of light specific gravity is charged to replace air as necessity requires. However, the configuration for controlling the atmosphere in the chamber according to the present invention is not limited to what was mentioned above. In other words, to set the inside of the chamber 1 in a negative pressure, it is not limited to maintaining to, for example, a low vacuum state of about 0.05 MPa to 0.1 Pa, and it is possible to set the inside pressure at a high level of vacuum, and the higher the degree of vacuum, the lower is it possible to reduce the energy loss of electrons. And, the ambient gas in the irradiation chamber is preferably one or a plurality of gasses selected from air, oxygen, nitrogen, hydrogen, carbon dioxide, argon and helium. By selecting an ambient gas properly for the chamber according to the type of an object and the purpose of irradiation, the ambient atmosphere around the object can be controlled to a predetermined state. To reduce energy loss due to the atmosphere at normal pressure, the use of helium of light specific gravity is more suitable than a gas of large specific gravity, such as air. Even in an ambient gas at normal pressure, if a gas of light specific gravity, such as helium is used as the ambient gas, the energy loss of electrons can be made smaller than in an ambient gas of high specific gravity, such as air. Even in an ambient gas at positive pressure, though this depends on the level of pressure, if a gas of light specific gravity such as helium is used as the ambient gas, the energy loss of electrons can be reduced to a sufficiently low level.

In the embodiments described above, description has been made of cases of the apparatus structure suitable for irradiation of beverage containers 30 with electron beams on a batch production line, but the present invention is not limited to this apparatus structure and can be applied to cases where objects are irradiated with electron beams on a continuous production line, for example.

Needless to say, the embodiments described above may be applied by selecting or combining their configuration as one thinks right.

An eighth embodiment of the present invention will be described with reference to the drawings where necessary.

Figure 9:
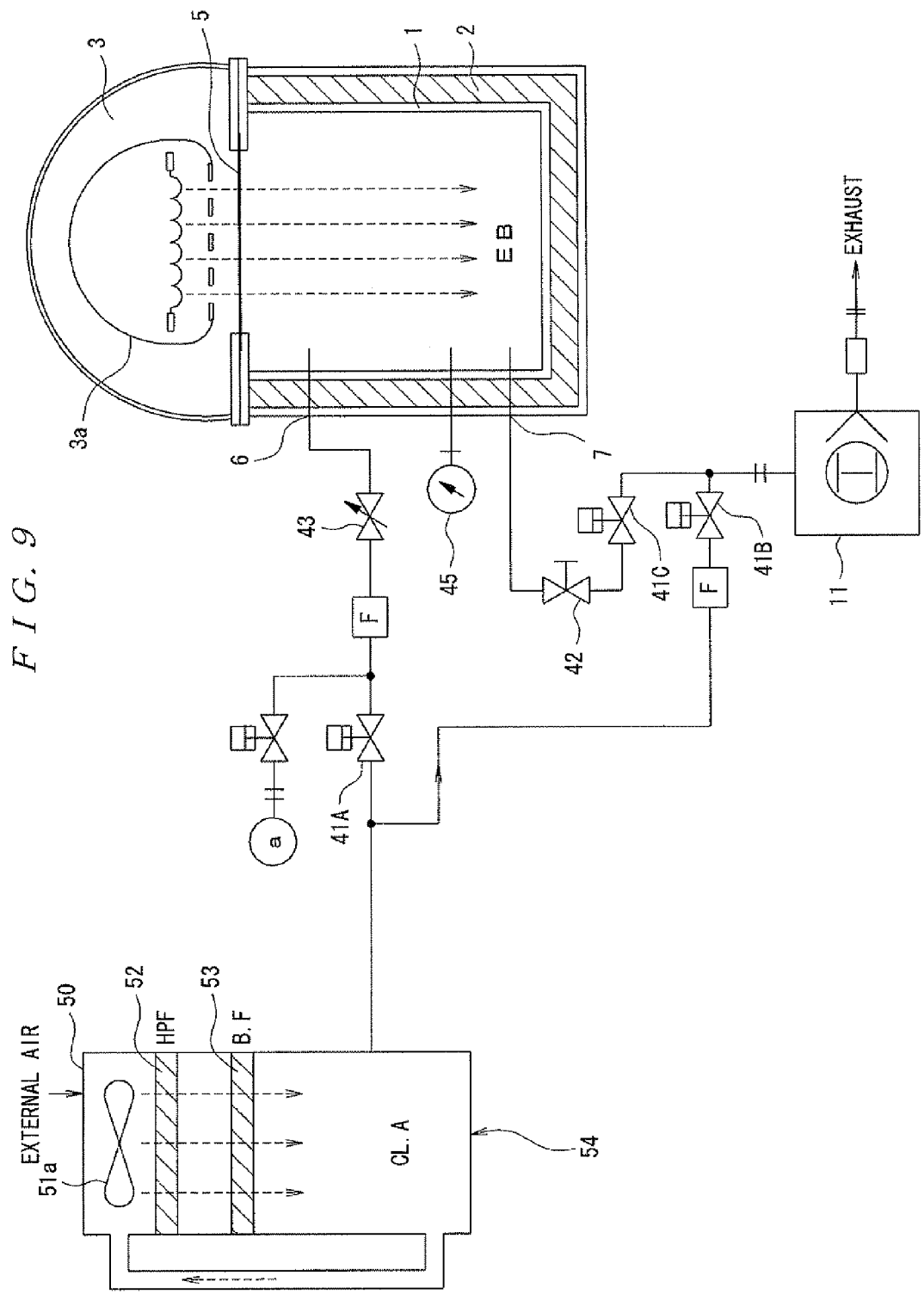
FIG. 9 is a schematic configuration diagram showing the electron beam irradiation apparatus according to an eighth embodiment of the present invention.

FIG. 9 is a schematic configuration diagram showing the electron beam irradiation apparatus according to the eighth embodiment of the present invention. FIG. 9 shows an irradiation chamber in a substantially cylindrical form seen in a cross section that includes the axial line, and this irradiation chamber 1 forms the main body of the electron beam irradiation apparatus.

As shown in FIG. 9, this electron beam irradiation apparatus includes a chamber 1, in other words, an electron beam irradiation chamber. This chamber 1 is a tight-sealed vessel of a pressure-resistant structure large enough to accommodate an object (for example, a beverage container 30 in a case to be described later), not shown, which is to be irradiated with electron beams EB. The chamber 1 is structured in a rectangular cylinder with its axial line extending vertically and is capable of maintaining an inside pressure. The chamber 1 is made of steel or stainless steel, and covered on its surfaces with an X-ray shielding material 2. An object entrance hole, not shown, which is openable and closable, is provided through the wall of the chamber 1, and an object can be carried into and out of the chamber 1 through this object entrance.

An electron beam generating room 3, which is a tight-sealed vessel in a hollow, hemispherical pressure-resistant structure is provided on the top of the chamber 1. This electron-beam generating room 3 has the underside of its hollow, hemispherical structure closely attached to the top of the chamber through the intermediary of the electron beam irradiation window 5, and can maintain its inside pressure separately from the pressure of the chamber 1. This electron beam generating room 3 includes an electron beam unit 3a serving as an electron beam irradiation means for emitting the electron beams into the electron beam irradiation area in the chamber. This electron beam unit 3a can emit low-energy electron beams EB, and output of its main body is set to not more than 200 kV. Therefore, the electron beam unit 3a is structured to be able to emit low-energy electron beams EB into the chamber 1 through the electron beam irradiation window 5.

In the electron beam irradiation apparatus, each of the chamber 1 and the electron beam generating room 3 is provided with piping and pressure control devices to control their inside pressure.

More specifically, the gas filling port 6 and the gas suction port 7 are provided through the wall of the chamber 1. The gas suction port 7 is connected to a vacuum pumping system 11 through a manual valve 42 and a cylinder valve 41C and piping. The vacuum pumping system 11 uses a dry pump. On the other hand, the gas filling port 6 is connected to a clean air generating device 54 through a variable flow valve 43, and a cylinder valve 41A. This clean air generating device 54 incorporates an HEPA filter 52, and a bio filter 53. A fan 51a is provided upstream of the HEPA filter 52 and the bio filter 53. The fan 51a is structured, after taking in the external air from the upper side in FIG. 9 and the internal air of the clean air generating device 54, to send air downwardly. Since the air passes through the HEPA filter 52 and the bio filter 53, clean air can be supplied into the chamber 1. Therefore, clean air as a leak gas, which is free of dust and bacteria, can be supplied into the chamber 1. The piping on the side of the clean air generating device 54 and the piping on the side of the vacuum pumping system 11 are mutually connected through the cylinder valve 41B.

The electron beam generating room 3 is provided with pressure-control piping and a pressure-control device. In other words, another gas suction port, not shown, which is configured in the same way as in the piping at the chamber 1 described above, is provided and connected through piping to the vacuum pumping system for the electron beam generating room 3. More specifically, the vacuum pumping system 11 for the electron beam generating room 3 draws air or gas out of the electron beam generating room 3 through the gas suction port 7, thereby setting the electron beam generating room 3 in a high vacuum state of not more than $10^{-3}$ Pa, which is a first negative pressure.

When electron beams EB are emitted into the chamber 1, oxygen or the like in the chamber 1 is consumed by radical reaction or oxygen transformation into plasma, so that under a negative pressure environment, oxygen is likely to run out, which is considered to have effects on the irradiation process. To mitigate the effects, in this electron beam irradiation apparatus, a control panel (not shown) is provided, which includes a pressure control means for controlling the variable flow valve 43 and the cylinder valve 41A, respectively. By operating the pressure control process on the control panel, oxygen is supplied to replenish oxygen consumed and the pressure in the chamber as a second negative pressure is controlled to be within a certain range. In this pressure control process, by changing the height of the second negative pressure, the degree of scattering of electrons is changed. Thus, the disorderliness of direction of electron range in the chamber 1 can be obtained. The pressure control operation by the control panel also controls the first negative pressure in the electron beam generating room 3.

A pressure control process, which controls the pressure of the electron beam generating room 3 to a predetermined negative pressure and also controls the pressure of the chamber 1 to a second negative pressure whose absolute pressure is higher than the first negative pressure, corresponds to the above-described pressure control means.

More specifically, the control panel, by specified control signals, performs control functions to turn on and off power supply to various parts, open and close the cylinder valves, regulates flow rate of the variable flow valve, turn on and off power supply to the vacuum pumping system to enable the pressure control process to be executed. The control panel is formed by including a CPU that performs arithmetic operations and controls the whole system of the electron beam irradiation apparatus based on specified control programs, all not shown, a ROM having the CPA's control programs previously stored in specified memory area, a RAM that stores data read from the ROM and arithmetic operation results necessary for operations in the CPU, and an interface to pass input and output of data to and from the external devices, including the operation panel of the electron beam irradiation apparatus. Those devices are mutually connected through buses as signal lines to transmit data. From the operation panel, it is possible to issue a command to execute the pressure control process and input a necessary set value according to the ambient atmosphere at a predetermined negative pressure. To show a concrete example, it is desirable to use a programmable controller for the control panel.

Thus, the electron beam irradiation apparatus, by the pressure control process in the control panel, is capable of controlling the ambient atmosphere around an object (a beverage container, for example) to a predetermined state. In this electron beam irradiation apparatus, to control the ambient atmosphere to a predetermined state is to control to ensure that the chamber inside is maintained at a second negative pressure whose absolute pressure is higher than a high vacuum state of not more than $10^{-3}$ Pa as the first negative pressure, more specifically, to control the chamber inside to a low vacuum state in a range of over $10^{-3}$ Pa and not more than 0.1 MPa. As for the pressure control value under control, it is possible to comply with the value decided based on a required electron range and an irradiation process, for example.

The operation and the effect of this electron beam irradiation apparatus will next be described.

In this electron beam irradiation apparatus, an object (a beverage container, for example) is carried from the object entrance into the chamber 1, set in a specified position in the chamber 1, and then the entrance is closed.

Subsequently, a process control process is executed by the control panel, the air of the chamber inside is drawn from the gas suction port 7 by the vacuum pumping system 11, and the inside pressure is controlled to a second negative pressure, namely, in a low vacuum state in a range over $10^3$ Pa and not more than 0.1 MPa.

Then, electrons are generated and accelerated by the electron beam irradiation means, and low energy electrons EB are emitted through the electron beam irradiation window 5 into the chamber 1. At this time, the electron beam generating room 3 is set in a high vacuum state of not more than $10^{-3}$ Pa as the first negative pressure by the pressure control process by the control panel. Therefore, energy loss of the electron beams EB hardly occurs in the electron beam generating room 3.

In the electron beam irradiation apparatus, since the air in the chamber 1 is drawn from the gas suction port 7 by the vacuum pumping system 11 and the chamber 1 is set at a low vacuum state of over $10^{-3}$ Pa and not more than 0.1 MPa, the chamber pressure is controlled to be constantly at the second negative pressure whose absolute pressure is higher than the first negative pressure. And, because the abundance of gas is low, the electron beams EB can be put in a condition that they can move easily even in the chamber 1 (in the condition that energy loss is small). Therefore, the energy loss of the electron beams EB in the gas in the chamber 1 is reduced. As a result, even low-energy electron beams are used, energy loss of the electron beams can be inhibited, and irradiation with electron beams can be performed efficiently. Also in this case, though this is not shown, by installing an electron deflecting beams in the inside or at the outside of the chamber 1, it becomes possible to perform more efficient electron irradiation.

In this electron beam irradiation apparatus, by a pressure control process on the control panel, by changing the height of the second negative pressure, the air density is changed so that the degree of scattering of electrons can be changed, and as a result, the disorderliness in direction of electron range can be obtained. For this reason, an object can be irradiated with electron beams uniformly, and more efficient irradiation with electron beams can be achieved.

The configuration of the above-mentioned pressure control process is not limited to a configuration such that the ambient atmosphere pressure is kept at a fixed level during irradiation by changing the ambient atmosphere pressure in the chamber 1 to a set pressure value according to different irradiation conditions depending on the shape of an object, for example, but the configuration may be in a form such that the ambient atmosphere pressure is changed intentionally during irradiation.

A specific example of the pressure control process, which changes the ambient atmospheric pressure in the chamber, in other words, changes the height of the second negative pressure, is shown below. For example, in a process of irradiating an object with electron beams, the air in the chamber 1 is drawn out from the gas suction port 7 by the vacuum pumping system 11, and under a condition that the chamber is maintained at a certain low vacuum state as the second negative pressure in a range of over $10^3$ Pa and not more than 1 MPa, irradiating an object with electron beams EB is started, and immediately after this, by performing this order of an operation of closing, opening and closing the cylinder valve 41A connected through the variable flow valve 43 to the gas filling port 6, clean air is supplied from the clean air generating device 54 into the chamber 1 and instantly, in a very short time of not longer than 1 second, for example, ambient atmosphere change-over control is performed so that clean air is charged into the chamber 1 and that the ambient atmospheric pressure in the chamber 1 is changed to a negative pressure whose absolute pressure is higher than the second negative pressure that existed just before this changeover. After the atmosphere change-over occurs, it follows that the electron beams EB, which, just before this atmosphere changeover, has reached the chamber's low area remote from the electron beam irradiation window 5, is instantaneously covered by the clean air atmosphere in a negative pressure state whose absolute pressure is higher than the second negative pressure that existed just before the atmosphere changeover. As a result, the electron beams EB suddenly collide with large amounts of atmospheric gas molecules even in the low area in the chamber 1. Though this takes place in a short length of time, a sufficient amount of electron shower is formed even in the low area in the chamber 1, making it possible to perform uniform irradiation to the object.

On the other hand, in a case where electron beam irradiation is performed while a clean air atmosphere in a negative pressure state close to a normal pressure is maintained in the chamber 1 throughout the whole of the irradiation process to one object, energy of electrons is consumed as the electron beams EB emitted into the chamber 1 collide with the atmospheric gas molecules existing in large amounts in the upper area close to the electron beam irradiation window 5 in the chamber, so that the amount of electron beams reaching the lower area remote from the electron beam irradiation window 5 decreases and a sufficient amount of electron beam shower cannot be formed in the low area. According to the rate of that decrease, the uniformity of irradiation of an object with electron beams is reduced. Therefore, the configuration of the pressure control process to perform atmosphere changeover control that instantaneously changes from the height of the second negative pressure or, from the atmospheric pressure in the chamber 1, to a negative pressure state whose absolute pressure is higher than the second negative pressure, during an irradiation process, is desirable because uniform irradiation to the object can be obtained, though this is in a short period of time. Another advantage is that by properly setting doses of irradiation of electron beams, the object can be sufficiently sterilized during a period of uniform irradiation in the above-mentioned short time.

Though this is not illustrated in FIG. 9, a configuration for control so that two pieces of cylinder valve 41A are connected in series to the gas filling port 6 through the variable flow valve 43 and they are opened and closed in series or a configuration that uses a fast-operating butterfly valve in place of the above-mentioned cylinder valve 41A will be suitable for atmosphere changeover control at higher speed.

In a configuration that a plurality of cylinder valve 41A are connected to the gas filling port 6 through the variable flow valve 43, in which if those cylinders 41A are positioned certain distances mutually separated from each other and if the pipes between the plurality of cylinder valve 41A are filled with clean air and afterwards, if the cylinder valve 41A close to the chamber 1 is opened, it will be easy to supply a limited amount of clean air to the chamber 1.

Further, in the above configuration, if the number of cylinder valves 41A provided in series is not less than three, by selecting a combination of two cylinder valves 41A which are closed before the atmosphere changeover control is performed, the amount of clean air stored in the piping between the two closed cylinder valves 41A can be changed and the amount of clean air supplied to the chamber 1 can be selectively adjusted.

The configurations of pressure control process for the atmosphere changeover control described above were conceived by the present inventors based on considerations about the relation between electron beam range and the degree of scattering and the atmosphere conditions. The fact that the electron beam range and the degree of scattering depend on the ambient atmosphere pressure in the electron beam irradiation area and the kind of ambient gas has been disclosed, for example, in research paper by Yoshiaki Arata et. al. "Some Fundamental Properties of Nonvacuum Electron Beam" Transactions of J.W.S. September 1970 p. 40-p. 59. This research paper shows experiment results of electron scattering (plasma formation) conducted by changing the atmospheric pressure in a range of 13.33 Pa (10-11 mHg)~101325 Pa (760 mmHg) about two kinds of ambient atmospheric gas of air or helium by using electron beams accelerated at 60 kV with regard to the dependency In the electron beam irradiation apparatus, as clean gas used in controlling the second negative pressure in the chamber 1, dust-free, germ-free clean air is supplied. Therefore, this apparatus is suitable for cases where objects are food and drink, water, pharmaceutical products, Chinese medicines, cosmetics and so on or packaging material for those products.

In the embodiment described above, description has been made of a case where the clean air generating device 54 is installed in consideration of the use of the sterilization and material reformulation processes, but various gas generating devices or a gas cylinder may be connected according the irradiation process instead of the clean air generating device 54. For example, a gas cylinder of helium gas may be connected through piping instead of the clean air generating device 54. Also by charging a helium gas with light specific gravity from the gas filling port into the chamber 1 instead of air, the electron beams EB can be put in a state that they can move easily (in a state with less energy loss).

The electron beam irradiation apparatus according to a ninth embodiment of the present invention will next be described with reference to FIGS. 10A and 10B where necessary.

FIGS. 10A and 10B are schematic configuration diagrams showing the electron beam irradiation apparatus according to a ninth embodiment of the present invention, in a case where the electron beam irradiation apparatus according to the eighth embodiment is used on a continuous process line. In this embodiment, the electron beam irradiation apparatus of the present invention is applied to a hollow beverage container 30 in a complicated shape as an object, such as a PET bottle for cold beverage, which is irradiated with electron beams. FIG. 10A is a view as seen from the top of the electron beam irradiation apparatus and shows the process chamber in sectional view in the transport direction. FIG. 103 is a view as seen from the front and shows the process chamber in cross section in the transport direction. Those configurations identical with those in the eighth embodiment are designated by the same numerals and their descriptions are omitted where necessary.

The ninth embodiment includes a plurality of sub rooms provided adjacent to the irradiation chamber 31, and an object transport device 28 as the object transport means for transporting beverage containers 30 between the plurality of sub rooms and the irradiation chamber 31. The irradiation chamber 31 is formed in the same tight-sealed vessel in a pressure-resistant structure as the one described above, excepting that the irradiation chamber 31 is in a box shape in the transport direction. Therefore, the ambient atmosphere around the beverage container 30 can be controlled in a specified state in the irradiation chamber 31. Further, like in the eighth embodiment, the electron beam generating room 3, in which electron beams can be radiated in a wide area in the irradiation chamber 31, is provided almost in the center at the top of the irradiation chamber 31. Though this is not shown, an electron deflecting means is installed in the inside and the outside of the irradiation chamber 31 as necessity requires.

As for the plurality of sub rooms, a plurality of front sub room 34 and a plurality of rear sub room 35 are provided respectively at the front and the rear of the irradiation chamber 31. FIGS. 10A and 10B show an example in which three front sub rooms in parallel and three rear sub rooms in parallel are arranged in the transport direction. It is arranged that the inside pressure of the different rooms can be maintained individually. Like in the irradiation chamber 1, the pressure can be controlled individually by the control panel from the atmospheric air pressure to a desired negative pressure.

The object transport device 28 is configured such that beverage containers 30 can be transported in the transport direction by a conveyor mechanism, not shown. The transport mechanism is not limited to a conveyor mechanism, but, for example, a feed-screw type transport mechanism may be adopted.

A front gate valve 32 is provided on the transport-direction-downstream side of each of the front sub room 34 and the rear sub room 34. A rear gate valve 33 is provided on the transport-direction-upstream side of each of the front sub room 34 and the rear sub room 35. The gate valves 32, 33, which serve as the dividers of the rooms, have their parts for delivery to the object transport device 28 thinned in shape, thus obviating the need to provide additional delivery devices at the dividers of the rooms.

The irradiation chamber 31, and the front and rear sub rooms 34, 35 adjacent to the irradiation room 31 are equipped with the above-mentioned pressure-control piping and pressure control device in the same way as has been described above. More specifically, as shown in FIGS. 10A and 10B, in anticipation of the use of the sterilization and material reformulation processes, it has been arranged that clean air can be supplied from the clean air generating device, which includes the HEPA filter 52 and the bio filter 53. Like in the eighth embodiment, the vacuum pumping system 11 having a structure that uses a dry pump is also mounted to the front sub room 34 and the rear sub room 35. Needless to say, various gas generating devices or a gas cylinder may be connected according the irradiation process instead of the clean air generating device 54.

A proximity sensor, not shown, intended to check for presence or absence of a beverage container is provided at the irradiation chamber 31, and the front and rear sub rooms 34,35 adjacent to the irradiation chamber 31. Those proximity sensors are connected to the signal lines in such a way as to output a specific signal showing absence or presence of a beverage container to the control panel. The gate valves 32, 33 are controlled so that the respective valves can be opened and closed by a specified pressure control process, which is executed by the control panel, and which will be described later.

Figure 12:
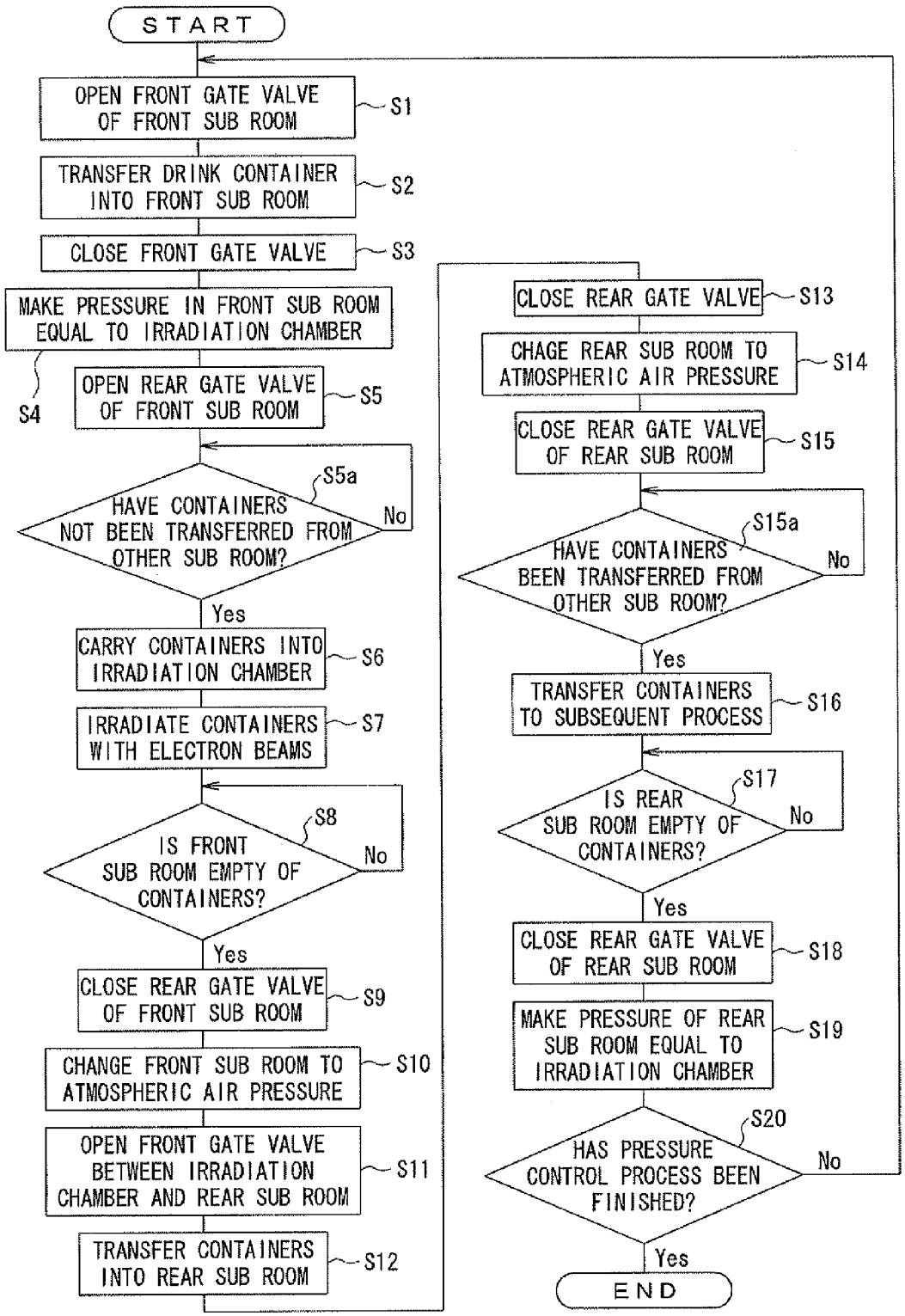
FIG. 12 is a flowchart of a pressure control process by a control panel in the electron beam irradiation apparatus according to the ninth embodiment of the present invention.

FIG. 12 is a flowchart of the pressure control process executed by the control panel. As shown in FIG. 12, when the pressure control process is executed by the control panel, the process proceeds to step S1, where the front gate valve 32 at the front sub room 34 is opened, and moves on to step S2. In step S2, the object transport device 28 carries beverage containers 30 into the front sub room, and the process proceeds to step S3. In step S3, the front gate valve 32 is closed, the process goes on to step S4. In the next step S4, the pressures in the front sub room 34 and the chamber 31 are made equal, and the process goes on to step S5. In step S5, the rear gate valve 33 of the front sub room 34 is opened, the process proceeds to step S5a. In step S5a, it is confirmed that transfer of beverage containers 30 to the irradiation chamber 31 has been completed from the other sub rooms, and if the completion is conformed, the process promptly moves to step S6. In other words, in this process, the pressures of the front sub room 34 and the irradiation chamber 31 are respectively set to a second negative pressure described in the eighth embodiment and controlled to within a predetermined range.

In the pressure control process by the control panel, it is arranged such that when the gate valves 32, 33 serving as the dividers of the rooms are opened, the pressure in their preceding process never fails to be set at a level on the lower side. Therefore, though the irradiation chamber 31 and the front sub room 34 are made equal to the second negative pressure in the process of step S6, until the gate valve 32 is opened, the pressure in the front sub room 34 is controlled to a lower than that of the irradiation chamber 31. In this manner, the flow current in the apparatus is intentionally controlled so that the current flows from the subsequent process side to the preceding process side, by which to prevent bacteria or dust from the preceding process from entering the subsequent process (this applies to when other gate valves are opened and closed).

In the next step S6, the object transport device 28 continuously carries the beverage containers sent from other sub rooms into the irradiation chamber 31, and the process moves on to step S7. In step S7, the irradiation process is performed, and the process goes on to step S8. In step S8, it is confirmed by a signal from the proximity sensor whether there is no longer any more beverage container left in the front sub room 34. More specifically, the front sub room 34 is empty of beverage containers 30 (YES), the process moves on to step S9. If the room 34 is not empty (NO), waiting takes place in step S8. In step S9, the rear gate valve 33 of the front sub room 34 is closed, and the process goes to step S10. In step S10, change the front sub room 34 to the atmospheric air pressure is performed, and the process goes to step S11.

In step S11, the front gate valve 32 between the irradiation chamber 31 is opened, and the process moves on to step S12. In step S12, the object transport device 28 performs a process to continuously carry the irradiated beverage containers 30 from the irradiation chamber 31 into the rear sub room 35, and the process goes to step S13.

In step S13, a control signal is issued at specified timing so that after the beverage containers 30 are transferred, the rear gate valve 33 is closed, and then the process goes to step S14. In step S15, a process to change the rear sub room 35 to the atmospheric air pressure and the process moves to step S15a. In step S15a, it is confirmed that transfer of beverage containers 30 to the subsequent process has been completed at the other sub rooms, and if the completion is confirmed, the process promptly moves to step S16. In step S16, the object transport device 28 continuously carries the beverage containers 30 sent from the other sub rooms to the subsequent process, and the process goes to step S17.

In step S17, it is confirmed by a signal from the proximity sensor whether there is no longer any more beverage container left in the rear sub room 35. More specifically, the rear sub room 35 is empty of beverage containers 30 (YES), the process moves on to step S18. If the rear sub room 35 is not empty (NO), waiting takes place in step S17. In step S18, the rear gate valve 33 of the rear sub room 35 is closed, and the process goes to step S19. In step S19, a series of processes to change the rear sub room 35 to a pressure same as in the irradiation chamber 31 is performed, and the process goes to step S20. In step S20, it is confirmed, for example, based on a signal from the proximity sensor of the front sub room 34 whether the pressure control process has been finished. More specifically, if beverage containers 30 have stopped being supplied to the front sub room 34 (YES), the pressure control process is finished, or if not so (NO), the process returns to step S1. In the electron beam irradiation apparatus according to the ninth embodiment, this pressure control means corresponds to the pressure control means.

As has been described, the electron beam irradiation apparatus of the ninth embodiment includes a plurality of front sub room 34 and a plurality of the rear sub rooms, and by executing the above-described series of pressure control processes on the control panel, beverage containers 30 can be transported over the whole length of the apparatus.

According to the electron beam irradiation apparatus, since the gate valves 32, 33 as the shield doors are provided respectively at the object entrance and exit, it is easy to apply a low vacuum or a specific gas atmosphere in the chamber or maintain the ambient atmosphere around the object in a specified state.

According to this electron beam irradiation apparatus, the front sub room 34, the irradiation chamber 31, and the rear sub room 35 can be respectively controlled in multiple stages of pressure, and since the gas current is arranged to flow from the subsequent process towards the preceding process, it is possible to suitably prevent airborne bacteria and dust from the pre-processing process from entering and also prevent gases containing sterilized dead bacteria or the like from scattering disorderly.

The electron beam irradiation apparatus according to the tenth embodiment of the present invention will be described with reference to FIGS. 11A and 11B where necessary. The configurations identical with those in the eighth and ninth embodiments are designated by the same numerals and their descriptions are omitted where considered obvious.

FIGS. 11A to 11C are schematic configuration diagrams showing the electron beam irradiation apparatus according to the tenth embodiment of the present invention, and this is an example where the electron beam irradiation apparatus according to the eighth embodiment is applied to a continuous process line. In this embodiment, an example of usage is shown in which the electron beam irradiation apparatus according to the present invention is applied to sterilize hollow beverage containers 30 as objects by using electron irradiation as in the ninth embodiment. FIG. 11A is a diagram as seen from the top, with the process chamber shown in a cross section taken in the transport direction. FIG. 11B is a diagram of the front sub room seen from the preceding process side and in a transverse cross section. FIG. 11C is a diagram showing the transport block in FIG. 11B on an enlarged scale.

As illustrated in those figures, like in the ninth embodiment, this tenth embodiment also includes a plurality of sub rooms provided adjacent to the irradiation chamber 60, and the object transport means for transporting beverage containers 30 between the plurality of sub rooms and the irradiation chamber 60. This irradiation chamber 60 is in a tight-sealed vessel of a pressure-resistant structure formed in the same manner as the one described above, excepting that the irradiation chamber 60 is formed in a circular ring along the transport direction, and the ambient atmosphere around the beverage containers 30 can be controlled to be a specified state in the irradiation chamber 60. Like in the eighth embodiment, the electron beam generating room 3 that can emits electron beams EB in a wide area in the irradiation chamber 60 is provided at an upper portion of the irradiation chamber 60 in such a way as to extend along the transport region in a circular ring. Though this is not shown, an electron beam deflecting means is installed at a lower portion of the electron beam generating room 3 of the irradiation chamber 60 as necessity requires.

As illustrated, the plurality of sub rooms according to the tenth embodiment are respectively formed almost in the same circular form as in the irradiation chamber 60, and arranged adjacent to the irradiation chamber 60. In the example illustrated in the figures, the respective sub rooms are divided by partition walls 66 into many small compartments equally spaced in the circumferential direction of the circular ring (into 36 small compartments in the depicted example). In this embodiment, those compartments are respectively used as the front sub rooms 61 and the rear sub rooms 62

To be more specific, as shown in the figures, the front sub room 61 and the rear sub room 62 are each divided into small rooms by mounting the partition walls 66 radially on one inner frame 64, and fractionated by the adjacent partition walls 66 and an outer frame 63. Small gaps G exist between the partition walls 66 and the outer frame 63 as shown in FIG. 11C, but sealing material is not used. The pressure in each sub room can be controlled in process zone units, and like in the irradiation chamber 1, the pressure of each process zone can be controlled from the atmospheric air pressure to a desired negative pressure.

Furthermore, in this embodiment, the pressure of the front sub room 61 and the rear sub room 62 is designed to change to coincide with the height of the second negative pressure in the irradiation chamber 60 in collaboration with the transport device.

More specifically, the irradiation chamber 60 is a tightly sealed space enclosed by the inner frame 64 and the outer frame 63, and the outer frame 63 is formed to be unitary with the front process zone and the rear process zone, each forming an sub room. The irradiation chamber 60, the front process zone and the rear process zone respectively have a large number of hand devices 65 mounted on their inner frames 64 in such a manner as to correspond to the sub rooms 61, 62. Those hand devices 65, which hold beverage containers 30, can convey between the irradiation chamber 60 and the front sub room 61 of the front process zone and between the irradiation chamber 60 and the rear sub room 62.

The front process zone is configured so that its inner frame 64 rotate clockwise as illustrated. Each front sub room 61 is configured so that when the inner frame 64 rotates, the front sub room 61 turns away from the preceding process and comes closer to the irradiation chamber 60, and as the front sub room 61 is gradually pulled by the negative pressure of the irradiation chamber 60 and has reached the irradiation chamber 60 side, the pressure of the front sub room 61 has come to be at the same level as the irradiation chamber 60. Conversely, when each front sub room 61 turns and comes closer to the preceding process side from the irradiation chamber 60 side, the front sub room is pulled by the atmospheric air pressure of the preceding process side, and when the front sub room 61 has reached the preceding process side, the front sub room 61 has come to be at the atmospheric air pressure. The above description applies to the rear sub room 62 of the rear process zone which has the same structure as described above, and its description is omitted.

With regard to the outer frame 63 that forms the front sub room 61 of the front process zone, a single-purpose vacuum pumping system 69 and several-stage piping 68 are provided through the outside wall of the portion moving from the preceding process towards the irradiation chamber 60. This makes it possible to reduce the capacity of the vacuum pumping system 11 of the irradiation chamber 60 and improve the precision of pressure control. The several-stage pipes 68 have a larger diameter as they approach the irradiation chamber 60, which is intended to reduce the capacity of the vacuum pumping system 69 and makes smooth the pressure change of the front sub room 61. The above description applies to the rear sub room 62 of the rear process zone which has the same structure as described above and its description is omitted. The above-described object transport means corresponds to a rotating device, not shown, provided to be capable of rotating the inner frames of the irradiation chamber 60, and the front and rear process zones, and also to a number of hand devices 65 for objects for each of the inner frames 64.

The irradiation chamber 60 basically has a tight-sealed space, whereas the front and rear sub rooms 61, 62, owing to their structure, have tiny gaps G at their circumference as shown in FIG. 11C. Therefore, there is a possibility of leak from the tiny gap G when the irradiation chamber 60 is at a negative pressure. However, since the partition walls 66 are provided in multiple layers, they provide a large flow resistance and serve to minimize an amount of leak. By determining the capacity of the vacuum pumping system making allowance for possible leak, the irradiation chamber 60 can be maintained at a certain pressure.

As illustrated, also in the present embodiment, like in the eighth embodiment, in consideration of use of sterilization and material reformulation processes, it is arranged that clean air can be provided from the clean air generating device 54 that contains the HEPA filter 52 and the bio filter 53. In each vacuum pumping system 69, like in the eighth embodiment, a structure using a dry pump is adopted in the front and rear sub rooms 61, 62. Also in this embodiment, needless to say, as shown in examples described, various gas generators and gas storage cylinder can be connected according to an irradiation process, instead of the clean air generating device 54.

In the tenth embodiment, it is configured that a predetermined pressure control process can be executed by the control panel, and this will be described as follows.

Figure 13:
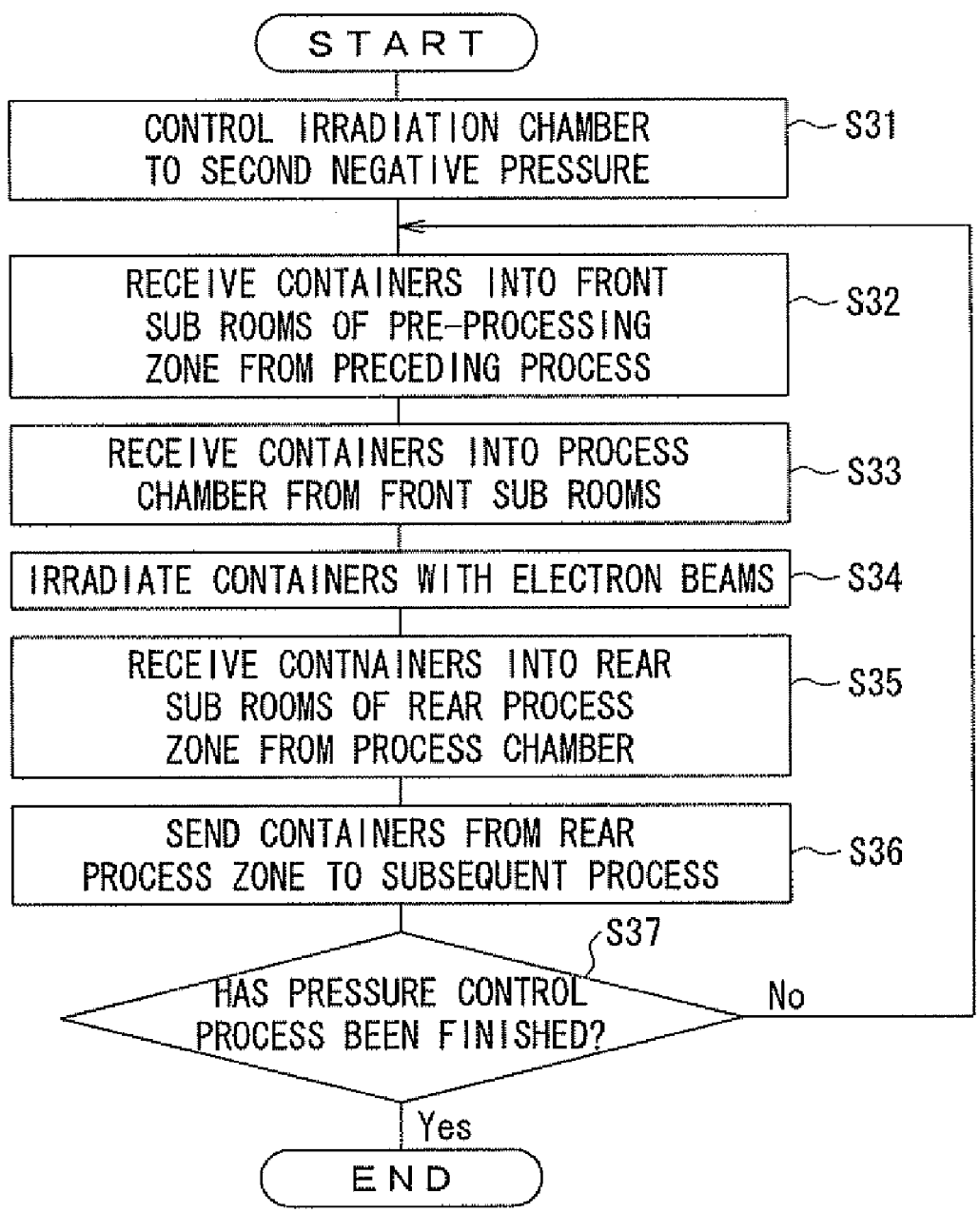
FIG. 13 is a flowchart of the pressure control process executed by the control panel in the electron beam irradiation apparatus according to the tenth embodiment of the present invention.

FIG. 13 is a flowchart of a pressure control process executed by the control panel. As shown in FIG. 13, when a pressure control process is executed by this control panel, the process is started with step S31 where the electron beam generating room is controlled to a predetermined first negative pressure and the irradiation chamber 60 is controlled to a predetermined second negative pressure, and the process moves to step S32. Here, like in the eighth embodiment, the first and second negative pressures have been set, and those pressures are controlled to be within predetermined ranges.

In step S32, a series of processes are performed: as the inner frame 64 is rotated clockwise, the inner frame of the pre-processing zone receives beverage containers through the hand devices 65 installed in the front sub rooms 61 from the rotating transport mechanism of the preceding process, and when the inner frame 64 of the pre-processing zone is further turned clockwise, the front sub rooms 61 holding the beverage containers 30 are turned closer towards the irradiation chamber 60 side. And, the process moves to step S33. At this time, because of the structure described above, the pressure in the front sub rooms 61 comes close to the second negative pressure in the irradiation chamber 60. Here, by installing a proximity sensor like in the ninth embodiment, it can be decided whether or not the beverage containers 30 are being transported by the front sub rooms 61 correctly.

In step S33, a series of processes take place: as the inner frame 64 of the irradiation chamber 60 is rotated counterclockwise, the beverage containers 30 sent sequentially from the front sub rooms 61 of the pre-processing zone are transferred via the hand device of the inner frame 64 into the irradiation chamber 60. Then, the process goes on to step S34. In step S34, in the irradiation chamber 60 which is controlled fixedly at a second negative pressure, as the inner frame 64 in the irradiation chamber 60 is further rotated counterclockwise, in this process the electron beams EB are emitted into the beverage containers 30 from the electron beam generating room controlled to a first negative pressure according to a prescribed process (the beverage containers 30 are irradiated on the upper half side of the ring-shaped irradiation chamber 60 in FIG. 11A in this example), and the beverage containers 30 are transported to the post-processing zone side. Then, the process proceeds to step S35.

In step S35, as the inner frame 64 is rotated clockwise, the electron-beam-irradiated beverage containers 30 sequentially sent from the irradiation chamber 60 are received via the hand devices 65 mounted in the respective rear sub rooms 62 in the inner frame 64 for the post-processing zone. And the process moves on to step S36.

In step S36, the inner frame 64 for the post-processing zone is further rotated clockwise, the rear sub rooms 62 holding the beverage containers 30 are turned towards the subsequent process side, and a process to sequentially deliver the beverage containers 30 to the rotating transport mechanism of the subsequent process. And the process goes on to step S37. At this time, because of the structure described above, the pressure in the rear sub rooms 62 gradually comes closer to the atmospheric air pressure.

In step S37, it is confirmed by a signal from the proximity sensors of the front sub rooms 61 whether or not the pressure control process has been finished. In other words, when beverage containers have stopped being supplied (YES), the pressure control process is finished, or if not so (NO), the process returns to step S32. Here, in the electron beam irradiation apparatus according to the tenth embodiment, the pressure control beams corresponds to the pressure control process.

As has been described, the electron beam irradiation apparatus according to the tenth embodiment includes the irradiation chamber 60, and a plurality of the front sub rooms 61 and a plurality of the rear sub rooms 62 arranged in a circular ring, and in the irradiation chamber 60 and the plurality of the front sub rooms 61 and the plurality of the rear sub rooms 62, by executing a series of pressure control processes continuously, the beverage containers on the line, transferred sequentially from the front sub rooms 61 pass through the electron beam irradiation area in an electron shower state in the irradiation chamber 60, and after being irradiated with electron beams EB, the beverage containers 30 are discharged sequentially from the rear sub rooms 62. Thus, the beverage containers 30 can flow continuously.

According to this electron beam irradiation apparatus, the pressure control process by the control panel is configured to control the pressure of the plurality of sub rooms individually in the pre-processing zone and in the post-processing zone. Therefore, it is possible to suitably apply a configuration shown in the eighth embodiment in the middle of a batch type production line or in a continuous production line on which beverage containers flow. In configuring a line such that objects such as beverage containers 30 are transferred in a continuous flow, the sub rooms whose inside pressure can be controlled individually are provided before and after the irradiation chamber 60, and this makes it possible to suitably maintain the height of the second negative pressure.

In this electron beam irradiation apparatus, in the configuration described above, because the pressure in the front sub rooms 61 and the rear sub rooms 62 is controlled to coincide with the height of the second negative pressure in the irradiation chamber 60, it is possible to securely maintain the second negative pressure in the irradiation chamber 60.

According to this electron beam irradiation apparatus, the plurality of the sub rooms 61, 62 are provided with a large number of partition walls 66, and those partition walls serve as, as it were, a pivoted door, and being provided in great numbers, those partition walls 66 form the labyrinth seal, thus suitably inhibiting a leak of pressure, and enabling a continuous transport of objects.

According to this electron beam irradiation apparatus, the plurality of the sub rooms 61, 62 are defined to enclose only its area and the vicinity of each of the beverage containers 30.

This is suitable for minimizing the area where the ambient atmosphere around each beverage container 30 is controlled to a predetermined state.

The electron beam irradiation apparatus according to an eleventh embodiment will be described with reference to FIGS. 14A and 14B where necessary. Those configurations identical with those in the eighth to tenth embodiments are designated with the same numerals and their descriptions are omitted.

Figure 14A:
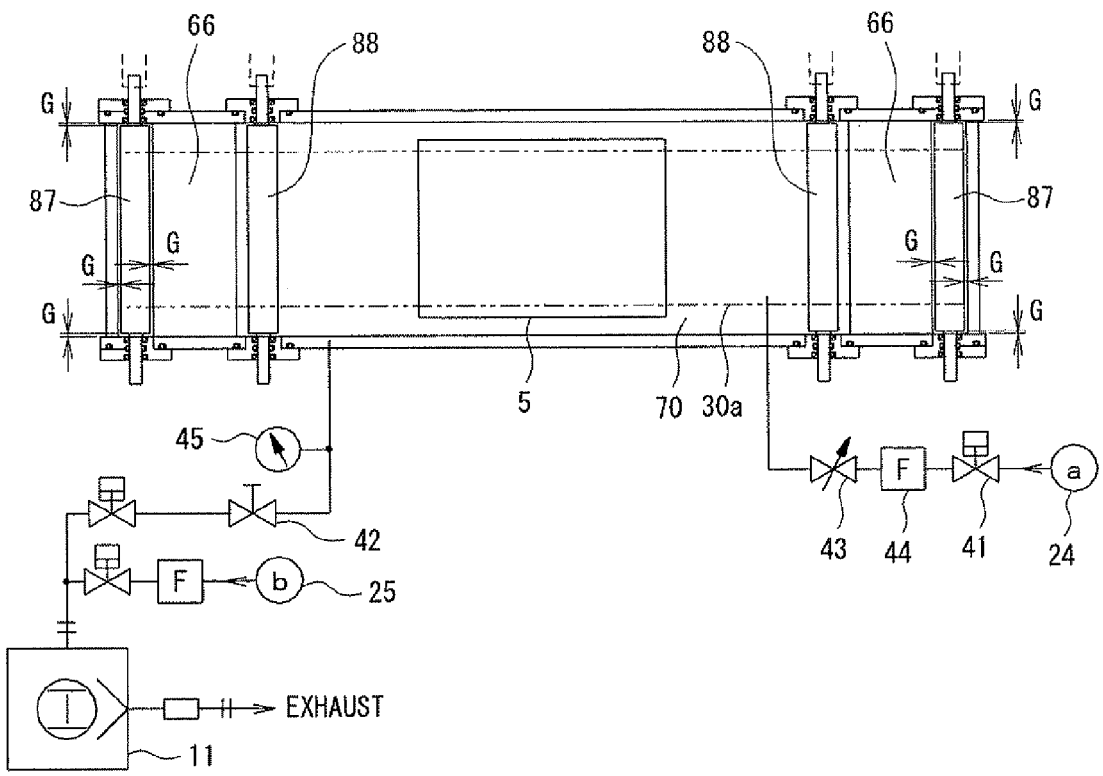
FIGS. 14A and 14B are schematic configuration diagrams showing the electron beam irradiation apparatus according to an eleventh embodiment of the present invention.
Figure 14B:
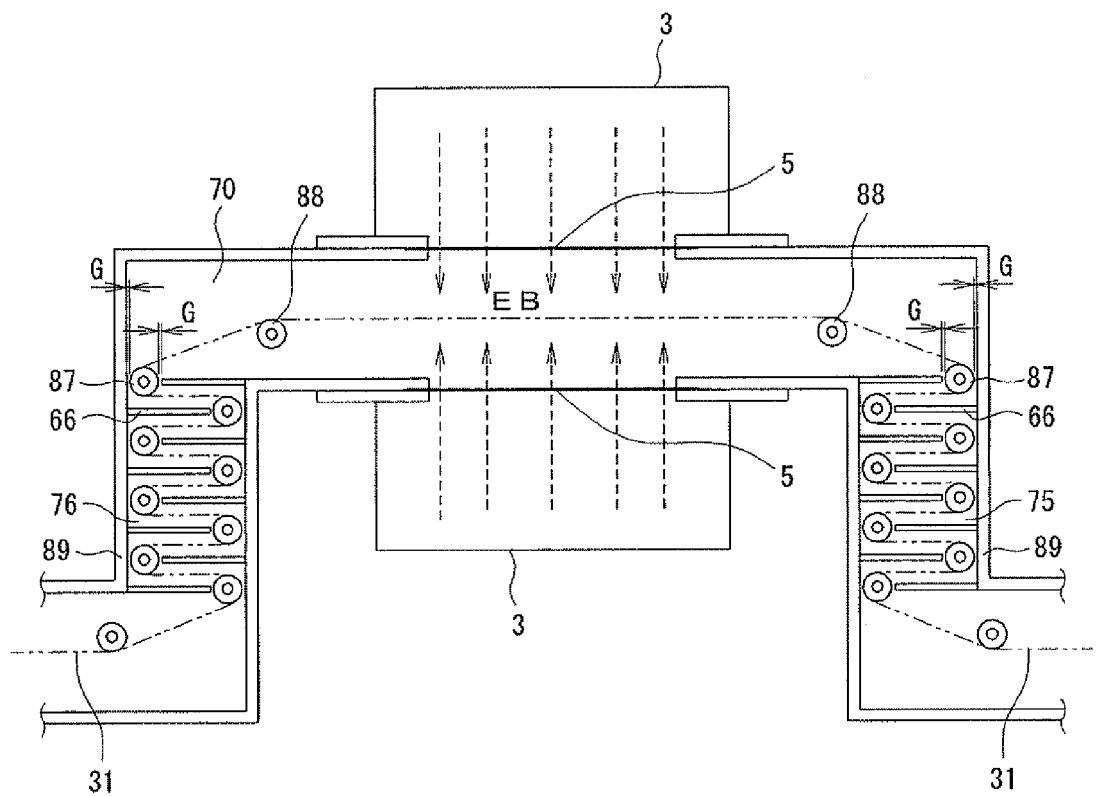

FIGS. 14A and 14B are schematic configuration diagrams showing the electron beam irradiation apparatus according to the eleventh embodiment, and depicts an example where the electron beam irradiation apparatus according to the tenth embodiment is applied to irradiation of sheet material with electron beams.

As shown in FIGS. 14A and 14B, the basic structure of the electron beam apparatus according to the eleventh embodiment is that the irradiation chamber 70 is provided having itself sandwiched on its top and bottom sides with the electron beam generating room 3 and having a plurality of the front sub rooms 75 and a plurality of the rear sub rooms 76 attached respectively to the front side and the rear side of it. With regard to the configuration of the front and rear sub rooms 75, 76, as shown in FIG. 14C, the partition walls 66 and gap rollers 87 are installed in a rectangular frame, and the sub rooms having small gaps G to a degree that unfolded paper sheet material 31 for a paper package for milk-drink can pass through, so that a labyrinth seal structure is formed. Under this configuration, though there are tiny gaps in the sub rooms, a plurality of the sub rooms are arranged in series, which structure makes the flow resistance small, so that like in the tenth embodiment, the negative pressure in the irradiation chamber 70 can be controlled easily by setting the capacity of the vacuum pumping system 11 with an amount of leak taken into account.

For sheet material 31, though this is not shown, because a mechanism configured to pull the sheet material 31 is provided in the subsequent process, the sheet material 31 passes a plurality of the front sub rooms 75 through the gap rollers 87 and the roller 88 since the preceding process, is irradiated on both sides with electron beams in the irradiation chamber 70 controlled to the second negative pressure, passes a plurality of the rear sub rooms 76, and is sent to the subsequent process. By the electron beam irradiation apparatus according to the eleventh embodiment, irradiation with high energy efficiency can be performed on sheet material, too.

As has been described, also by the electron beam irradiation method and the electron beam irradiation apparatus according to the eighth to eleventh embodiments, even if low-energy electron beams EB are used, beverage containers 30 as objects can be irradiated with electron beams EB uniformly.

Note that the electron beam irradiation method and the electron beam irradiation apparatus in the present invention are not limited to the eighth to eleventh embodiments, but may be embodied in various modifications without departing the spirit and the scope of the present invention.

For example, in the ninth to tenth embodiments described above, description has been made of a beverage container as an object, but the present invention is not limited to this object, and can be applied to, for example, food and drink, water pharmaceutical products, Chinese medicines, cosmetics, feeding stuffs, fertilizer, and so on or packaging material for those products. In other words, the present invention can be applied to from three-dimensional objects of complicated shapes to flat film to comply with kinds and shapes of object as occasion demands.

In the eighth to eleventh embodiments, description has been made referring to uses for sterilizing objects, but the present invention is not limited to such uses, and can be applied to other uses other than sterilization.

In the eighth to eleventh embodiments, description has been made of cases where the external shape of the chamber is previously decided according to the type of an object, but the chamber shape is not limited to this shape, and the chamber may be in a structure with a variable interior shape, which is changeable according to the shape of an object. To cite an example of such a chamber structure with variable interior shape, the chamber may be in a structure having sliding partition walls, which constitute the external shape of the chamber. Under this configuration, the chamber interior shape can be changed properly to suit the shape of an object. For this reason, an object can be irradiated with electron beams more efficiently and uniformly.

In the eight to eleventh embodiments described above, description has been made of cases where the chamber internal atmosphere is set in a low vacuum, or, a negative pressure state, and clean air or a helium gas with light specific gravity instead of air can be charged into the chamber, but the present invention is not limited to those conditions, and the ambient gas in the chamber may be one or a plurality of gasses selected from air, oxygen, nitrogen, hydrogen, carbon dioxide, argon and helium according to necessity in an irradiation process. By selecting an ambient gas properly for the chamber according to the type of an object and the purpose of irradiation, the ambient atmosphere around the object can be controlled to a predetermined state. When energy loss due to the ambient atmosphere is to be reduced, for example, helium with light specific gravity may be suitably used as described showing an example.

Needless to say, the embodiments described above may be applied by selecting or combining their configuration as one thinks right.

The electron beam irradiation apparatus for open-mouthed containers according to a twelfth embodiment of the present invention will be described as follows.

This electron beam irradiation apparatus for open-mouthed containers (beverage containers), wherein a front pressure adjusting chamber (front sub rooms) and a rear pressure adjusting chamber (rear sub rooms) are connected integrally to the side faces of the irradiation process chamber (irradiation chamber) for maintaining a negative pressure state with its own pressure reducing means, and a rotating transport device is disposed rotatably in each pressure adjusting chamber, a plurality of holding devices (hand devices) for holding open-mouthed containers are provided at roughly equal intervals on the outer surfaces of the rotating transport devices, and wherein the pressure reducing means is provided in such a way that open-mouthed containers can be transferred one after another from one rotating transport device to the other rotating transport device to the other rotating transport device from the front pressure adjusting chamber to the rear pressure adjusting chamber, that partition walls are provided at the rotating transport devices in the front and rear pressure adjusting chambers to divide the holding devices to form a plurality of small compartments by using the partition walls and chamber wall surfaces when the rotating transport devices are moving, and that it is arranged that the pressure is reduced in the small compartments in a range from an open-mouthed container entrance side of the front pressure adjusting chamber to the irradiation process chamber side and in the other range from the irradiation process chamber to the open-mouthed container exit side of the rear pressure adjusting chamber, and wherein at least one electron beam irradiation means is arranged in the irradiation process chamber.

Figure 15A:
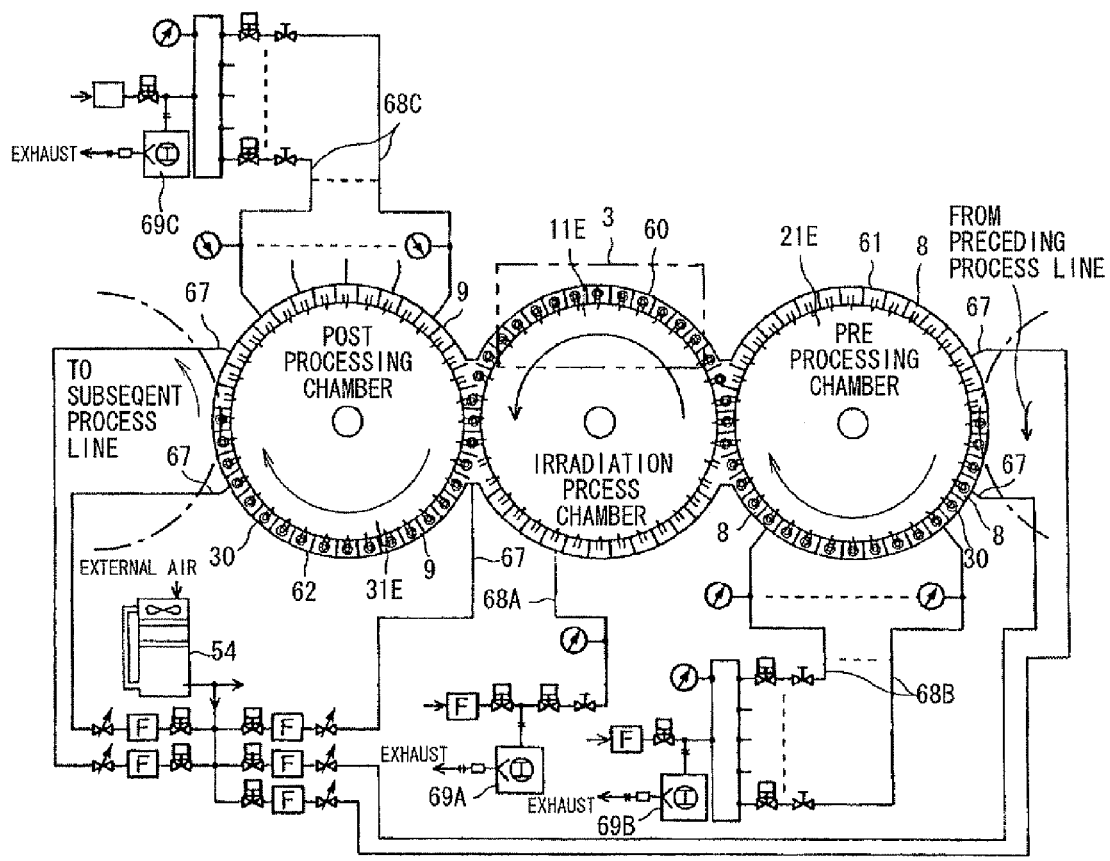
FIGS. 15A and 15B are schematic diagrams showing a principle of the electron beam irradiation apparatus for open-mouthed containers according to a twelfth embodiment of the present invention.

FIG. 15A shows the principle of the electron beam irradiation apparatus for open-mouthed containers according to the present invention, in which plastic bottles (beverage containers), which correspond to open-mouthed containers as objects, are used. A front pressure adjusting chamber (front sub rooms) 61 and a rear pressure adjusting camber (rear sub rooms) 62 are connected integrally to the side faces of the irradiation process chamber (irradiation chamber) located at the center. Rotating transport blocks 11E, 21E, and 31E, which are rotated as indicated with arrows and synchronized by a drive mechanism, are disposed rotatably in the respective chambers 60, 61, and 62, by which a circular transport path is formed to sequentially transport open-mouthed containers 30 through the outer walls of the chambers. Therefore, the front pressure adjusting chamber 61 linked to the pre-processing line, the irradiation process chamber 60, and the rear pressure adjusting chamber 62 are aligned in this order on a production line of open-mouthed containers 30.

A large number of holding devices (hand devices) 65 for holding open-mouthed containers during transportation are provided equally spaced on the outer surface of each of the rotating transport blocks 11E, 21E and 31E. By these holding devices 65, the open-mouthed containers 30 held in upright position can be smoothly delivered between the rotating transport blocks 11E, 21E and 31E in the respective chambers 60, 61, and 62 from the pre-processing line to the post-processing line of the open mouthed containers 30.

The inside of the irradiation process chamber 60 is configured in a pressure-resistant tight-sealed structure to reduce the pressure, piping 68A leading to a gas exhaust means including the vacuum pumping system 69A is connected to the irradiation process chamber, and the ambient atmosphere around an open-mouthed container 30, which is transported, is maintained at a predetermined negative pressure. At least one electron beam generating room 3 connected to a power supply is provided at a portion corresponding to the transport path as the electron beam irradiation room in the irradiation process chamber 60. By using this electron generating room 3, in which the electron beams are emitted to the transport path as the electron beam irradiation room in the irradiation process chamber 60 maintained at a negative pressure, and open-mouthed containers 30, which arrive here successively, are sterilized.

Because open-mouthed containers 30 are sterilized by being irradiated both at the outside and the inside with electron beams in a negative pressure atmosphere, electrons of low energy and at acceleration voltage of not more than 150 kV can be generated in the electron beam generating room 3. When the irradiation process chamber 60 is in a decompressed state, the attenuation of electron beams is reduced notably, even if the electron beams are of low energy, the electron range (flying distance) becomes longer and the amount of scattering of the electron beams is low, so that narrow-mouthed containers 30 can be irradiated into their inside with the electron beams effectively.

To effectively maintain the negative pressure state in the irradiation process chamber 60 to perform better irradiation with electron beams, a special idea based on this invention has been applied to the front pressure adjusting chamber 61 leading to the preprocessing line side as the container entrance side and the rear pressure adjusting chamber 62 leading to the container exit side.

More specifically, the partition walls 66 that separate the holding devices 65 are provided on the rotating transport blocks 21E, 31E in the front pressure adjusting chamber 61 and the rear pressure adjusting chamber 62, respectively. And multiple small compartments 8, 9 are as small rooms are formed by adjacent partition walls 66 on both sides of each holding device 65 and the chamber wall surface when the rotating transport blocks 21E, 31E are rotating.

In addition, to reduce the pressure in the plurality of small compartments 8 existing in the range from where open-mouthed containers 30 are delivered from the preceding process line till they go into the irradiation process chamber 60, a plurality of pipes 68B leading to the gas exhaust means including the vacuum pumping system 69B are connected to the wall in the above-mentioned range. Therefore, the small compartments B in the range from where open-mouthed containers 30 are delivered to the front pressure adjusting chamber 61 from the preceding process line until the irradiation process chamber 60 can be controlled effectively as the pressure adjusting range from the room pressure to a desired negative pressure.

On the rear pressure adjusting chamber 62 side, to reduce the pressure of the small compartments 9 formed in a range where open-mouthed containers 30 are moved from the irradiation process chamber 60 to the position of the subsequent process line, in the same manner as described above, a plurality of pipes 68C leading to the gas exhaust means including the vacuum pumping system 69C are connected to the wall in the above-mentioned range. Therefore, the small compartments in a range from the irradiation process chamber 60 until the open-mouthed containers 30 are delivered to the subsequent process line of the rear pressure adjusting chamber 62 can be controlled effectively as the pressure adjusting range from a desired negative pressure until the room pressure, opposite to what was mentioned above.

By configuring the plurality of pipes 68B, 68C to have a larger diameter as they approach the irradiation process chamber 60 or effectively reduce the pressure by increasing the number of pipes, the capacity of the vacuum pumping system 69A can be reduced or the pressure change in the front pressure adjusting chamber 61 and the rear pressure adjusting chamber 62 can be modulated. The range where the pressure of the small compartments in the front pressure adjusting chamber 61 and the rear pressure adjusting chamber 62 is reduced can be switched to the opposite side as occasion demands, in other words, the pressure can be reduced by providing a gas exhaust means for the small compartments 9 in the range where the containers are moved from the irradiation process chamber 60 to the preceding process in the front pressure adjusting chamber 61 or for the small compartments 9 in the range where the containers are moved from the irradiation process chamber 60 to the subsequent process line in the rear pressure adjusting chamber 62.

Figure 15B:
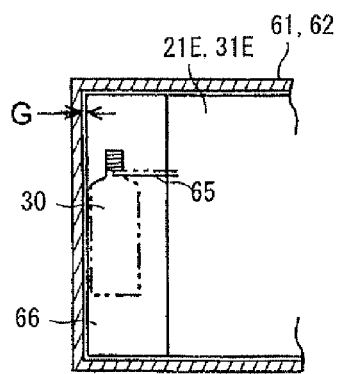

The partition walls 66, used to form the small compartments 8, 9, are installed to obtain tiny gaps G in cooperation with the outer wall of the chambers 61, 62 as shown in FIG. 15B. Thus, there are a plurality of the partition walls 66 in the range on the side which is open to the room pressure in each of the front pressure adjusting chamber 61 and the rear pressure adjusting chamber 62. Therefore, the partition walls 66 perform the work of a labyrinth structure, and the resistance to the flow from the irradiation process chamber 60 up to the outside at atmospheric air pressure becomes large, making it possible to maintain the negative pressure in the irradiation process chamber 60 without applying sealing, for example. As is obvious, by determining the vacuum pumping system 69A of the gas exhaust means in the irradiation process chamber making allowance for leak, the inside of the irradiation process chamber 60 can be maintained in a range of predetermined negative pressure state.

To be supplied with clean air, the irradiation process chamber 60, and the front and rear pressure adjusting chambers 61, 62 are each provided with a dry pump, for example, and connected with pipes 67 leading from a clean air generating device 54, which include suitable filters. To obtain a gas atmosphere suitable for irradiation with electron beams, instead of the clean air generating device 54, various gas supply devices for supply of a nitrogen gas, a helium gas or the like can be connected.

In the electron beam irradiation apparatus for open-mouthed containers configured as described, open-mouthed containers 30, held in upright position and transferred into the front pressure adjusting chamber 61 from the preceding process, pass through the front pressure adjusting chamber 61 and the irradiation process chamber 60, and are delivered from the rear pressure adjusting chamber 62 to the subsequent process. Those containers are sterilized by irradiation with electron beams from the electron beam generating room 3 in the negative pressure atmosphere in the irradiation process chamber 60 on the way. At this time, when the rotating transport block 21E in the front pressure adjusting chamber 61 is rotated clockwise, the small compartments 8 are formed in a range from the position for container delivery from the preceding process into the front pressure adjusting chamber 61 and to the area where the containers approach the irradiation process chamber 60, and those small compartments 8 holding the open-mouthed containers 30 are in a state gradually reduced in pressure from the atmospheric air pressure by the gas exhaust means, and when the compartments reach the rotating transport block 11E in the irradiation process chamber 60, the compartments come to almost the same negative pressure as the irradiation process chamber 60.

Conversely, after the rotating transport block 31E in the rear pressure adjusting chamber 62 rotate clockwise, the small compartments 9 are formed in a range from the irradiation process chamber 60 to the area where the containers approach the position of container discharge to the subsequent process line, and the small compartments holding open-mouthed containers 30 are gradually turned away from the negative pressure state in the irradiation process chamber 60 and come into the atmospheric air pressure by the vacuum pumping means, and when the containers 30 are ejected to the subsequent process line side, the compartments are at the atmospheric air pressure.

In the electron beam irradiation apparatus for open-mouthed containers is configured as described, because the irradiation process chamber 60, and the front and rear pressure adjusting chambers 61, 62 can be pressure-controlled individually and appropriately, by using the electron beam generating room 3 for low-energy electrons in the irradiation process chamber 60 maintained at a negative pressure, open-mouthed containers 30 can be sterilized with electron beams effectively.

Moreover, in the electron beam irradiation apparatus for open-mouthed containers, the irradiation process chamber 60, and the front and rear pressure adjusting chambers 61, 62 connected integrally to each other, and because open-mouthed containers held in upright position and transported sequentially by the rotating transport block in each chamber, and open-mouthed containers can be continuously irradiated with electron beams in a specified area in the irradiation process chamber 60 when those chambers are built into a production line for beverage or the like. Because this apparatus is configured such that the rotating transport blocks 21E, 21E, and 31E are rotated and the containers 30 are held in upright position and transported, unreasonable forces are hardly applied, and the transport devices are less likely to suffer wear and can be used for a long period of time on the production line.

Figure 16:
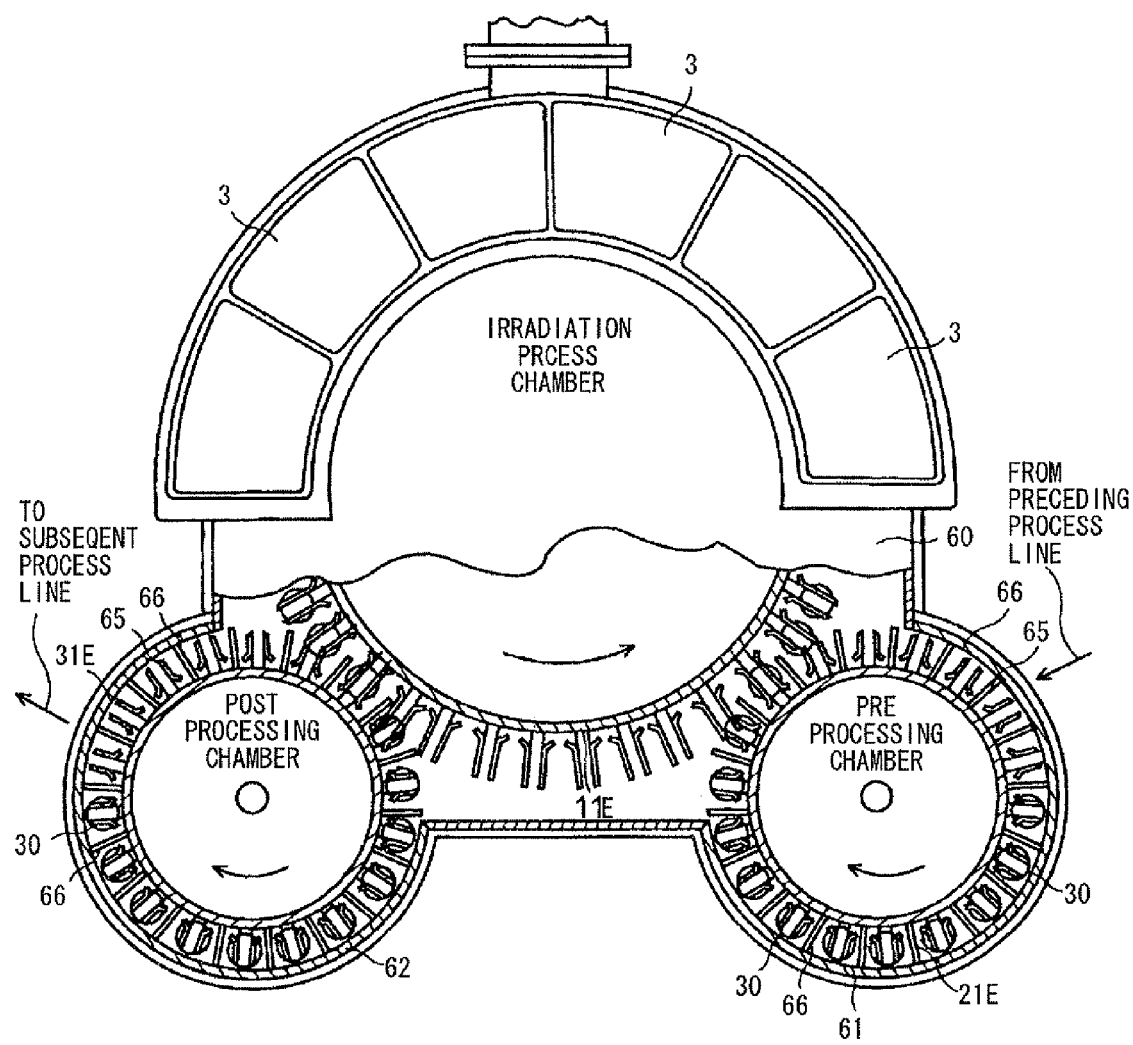
FIG. 16 is a schematic plan view partly in cross section of the electron beam irradiation apparatus for open-mouthed containers according to the twelfth embodiment of the present invention.
Figure 17:
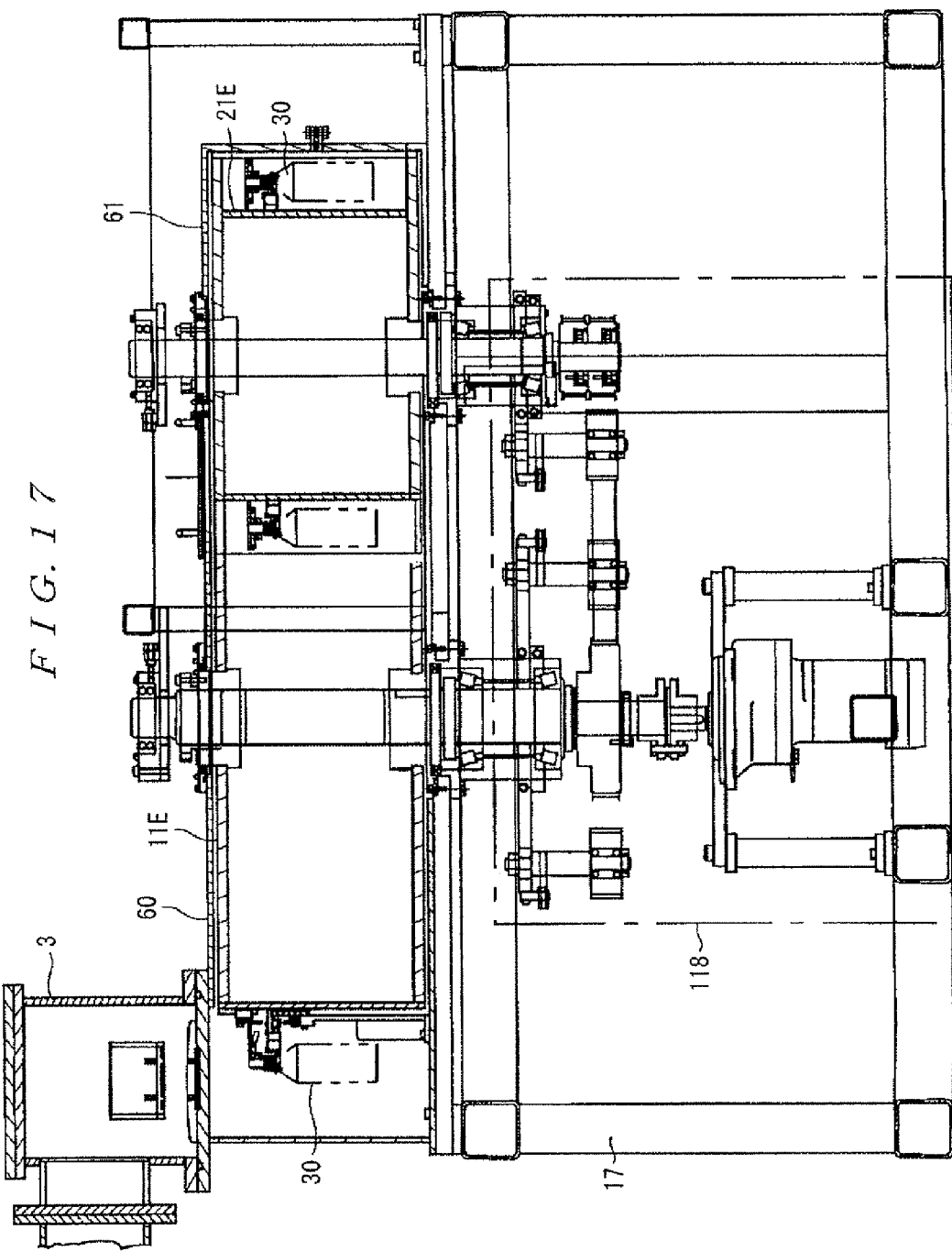
FIG. 17 is a schematic side view partly in cross section of FIG. 16.

FIGS. 16 and 17 show a concrete example of configuration of the electron beam irradiation apparatus for open-mouthed containers. In this example, the diameter of the irradiation process chamber 60 is made larger than that of the front pressure adjusting chamber 61 and the rear pressure adjusting chamber 62 which are connected integrally with the irradiation chamber. In this large irradiation process chamber 60, a plurality of electron beam generating rooms 3 are arranged in a circular-arc range in the upper surface portion corresponding to the position that serves as the transport path for open-mouthed containers and those electron generating rooms are respectively connected to power supplies (not shown). Therefore, while being transported in the irradiation process chamber 60, the open-mouthed containers can be treated by a sterilization process by irradiation with electron beams in a wide range where the electron beam generating rooms 3 are installed.

The irradiation process chamber 60, and the front and rear pressure adjusting chambers 61, 62 are connected integrally with each other and arranged on a support base 17, and the drive mechanism 118, such as a motor and wheels for synchronized driving of the rotating transport blocks 11E, 21E and 31E of the chambers 60, 61 and 62, are arranged in the support base 17. The rotating transport blocks 11E, 21E and 31E are formed in a planer hollow drum or by mounting circular frames to support arms.

Figure 18A:
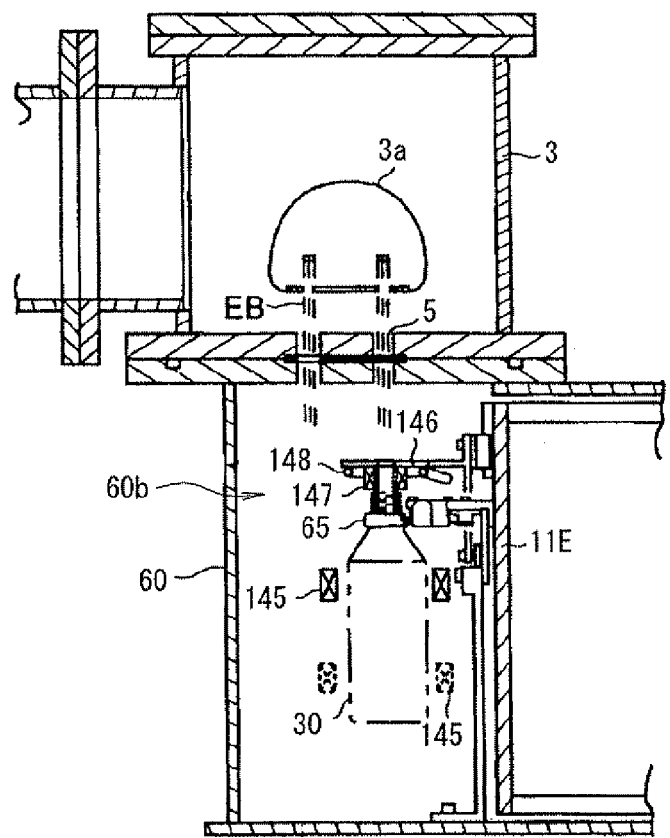
FIGS. 18A and 18B are longitudinal section showing an example of the electron beam irradiation means block used in the electron beam irradiation apparatus for open-mouthed containers according to the present invention.
Figure 18B:
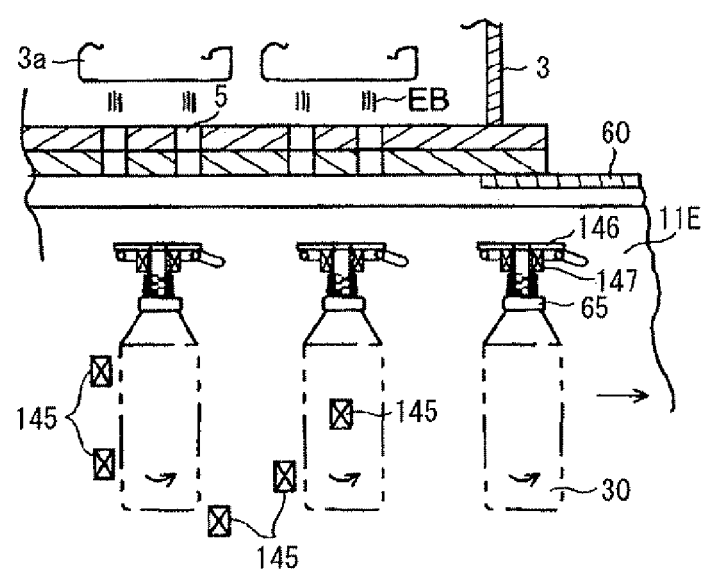

As shown in a longitudinal section view in FIG. 18A and a front view of in FIG. 18B, for example, with regard to each electron beam generating room 3 mounted on top of the irradiation process chamber 60, a plurality of electron beam units 3a are arranged in the electron beam generating room 3 that creates a high vacuum, such as $10^{-5}$ Pa. Electron beams EB generated by the electron beam unit 3a are emitted, through the electron beam irradiation window 5 formed as in a round or slit form, towards the transport path as the electron beam irradiation area 60b located at a lower position controlled to a negative pressure state, and the outside and the inside of each open-mouthed container 30 arriving while it is held by the holding device 65 of the rotating transport block 11E are sterilized by electron irradiation.

The electron beam generating rooms, each having at least an electron beam unit 3a, are mounted sequentially on the top of the irradiation process chamber 60. Electron beam deflectors 145 as electron beam deflecting means for deflecting electron beams EB from the electron beam generating room 3 are located on the transport path as an electron beam irradiation area 60b in the irradiation process chamber 60, which corresponds to an electron beam generating room 3. Those electron beam deflectors 145 are located at a position corresponding to the electron beam units 3a of each electron beam generating room 3 and at different positions in the height direction of an open-mouthed container 30. If the electron beam deflectors 145 are located in such a way as described above, even when irradiated from above by electron beams EB, the entire height-direction surface on an open-mouthed container 30 can be irradiated adequately. The electron beam deflector uses permanent magnets, and care should be taken in setting the position of the electron beam deflector to suitably deflect electron beams EB to achieve effective irradiation of the whole surface of an open-mouthed container 30.

Protective plates 146 are mounted above the holding devices 65 and supported by the rotating transport block 11E. The holding plate 146 has an electron-passing hole formed in it and an electron beam focusing device 147 made of permanent magnet in a ring form is attached to the holding plate 146. In the presence of the protective plate 146 and the electron beam focusing device 147, the electron beams can be emitted into the inside of the open-mouthed container 30 appropriately even if its neck is thin, thus enabling a sufficient sterilization of the container. The protective plate 146 is provided to a specific portion near the neck of the mouthed container to prevent excessive irradiation with electron beams. Therefore, being subjected to irradiation with electron beams, the surface of the protective plate 146 radiates heat, and therefore the protective plate 146 is made of material with good thermal conductivity, such as copper or aluminum, and when measures for heat dissipation are required, a cooling means, such as cooling pipe, is installed.

Figure 19A:
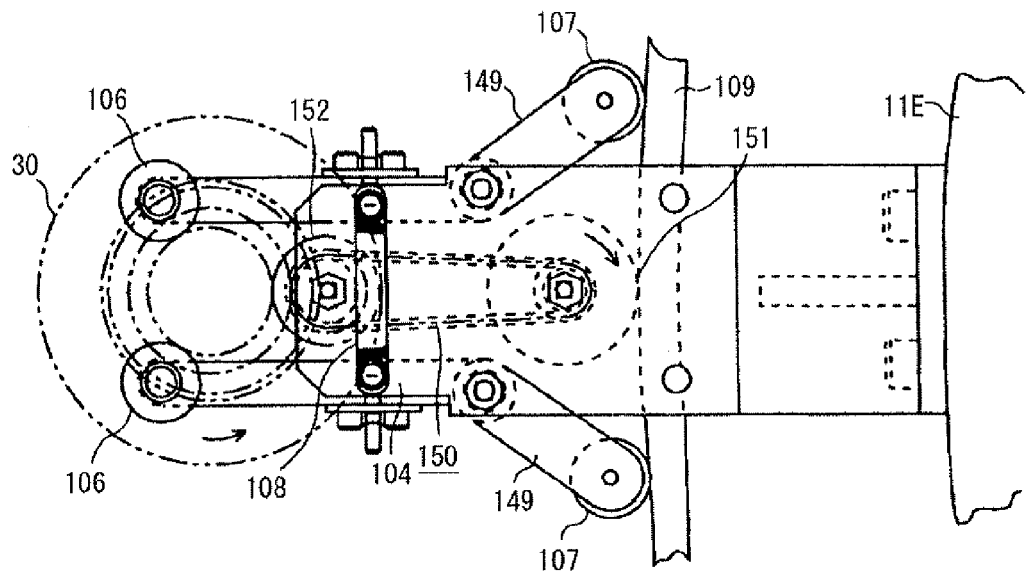
FIGS. 19A and 19B are schematic configuration diagrams showing the open-mouthed-container holding device block used in the electron beam irradiation apparatus for open-mouthed containers according to the present invention.
Figure 19B:
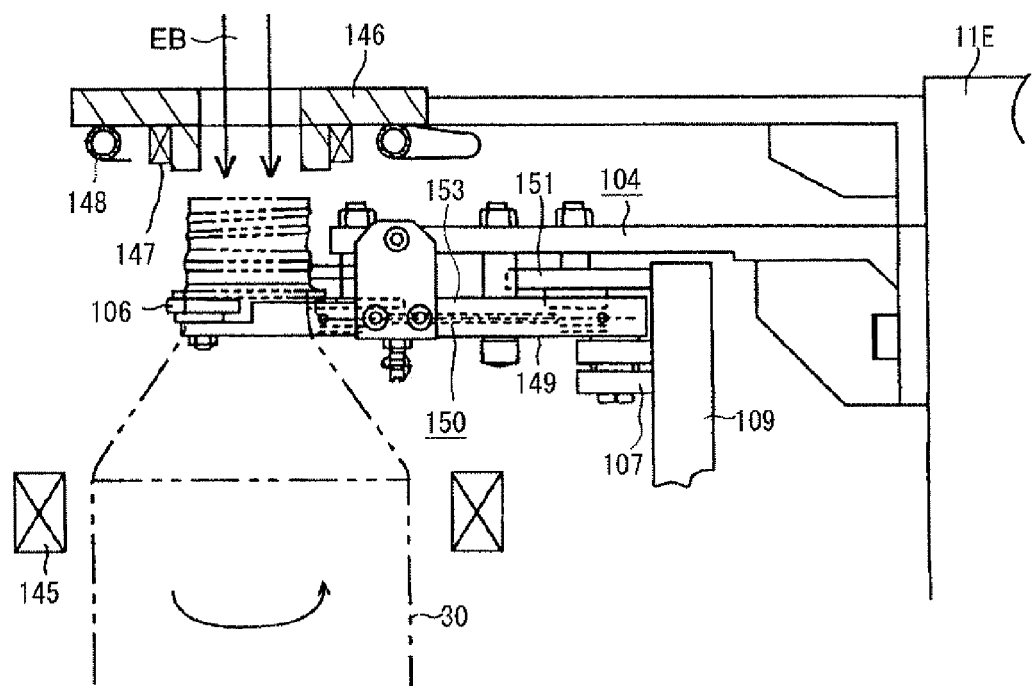

As shown in FIGS. 19A and 19B, in the present invention, as a result of contemplating the structure of the holding devices 65 on the rotating transport block 11E, a rotating device 150 to rotate an open-mouthed container 30 about its center is mounted to the holding device 65. This rotting device 150 can rotate an open-mouthed container when it is irradiated, and without adding any special means, the interior and exterior surfaces of a container can be irradiated uniformly.

To explain the holding device in detail, the holding device 65 is rotatably held by a link device using a pair of clamp levers 149 located on both sides of a support frame fixed to the surface of the rotating transport block 11E. Rollers 106 for holding an open-mouthed container 30 are provided at the outer ends of the clamp levers 149 as the link device and the inner ends are also fitted with rollers 107. Both clamp levers 149 are connected with a compression spring, and the inner rollers 107 are in contact with a clamp rail 109 provided over the whole range for holding an open-mouthed container. When this contact separates where there is no clamp rail 109 for delivery of an open-mouthed container, the outer ends of the clamp levers 149 are further separated by the force of the compression spring 108, and the holding of the open-mouthed container is released.

The rotating device 150 for rotating an open-mouthed container 30 about its center includes a drive disc 151, which is located below the support frame and rotates by engagement with the clamp rail 109, an open-mouthed container drive roller 152 for holding an open-mouthed container in cooperation with the rollers 106, 107, and a link drive means 153, such as a drive belt, stretched between the drive disc 151 and the open-mouthed container drive roller 152. Thus, the rotating force of the drive disk 151 is transmitted through the drive belt 53 to the drive roller 152, rotating the container about its center while it is transported, and the container's surfaces are uniformly irradiated with electron beams EB emitted through the electron beam irradiation window 5 and the electron beam focusing device 147 and also through the protective plate 146, which includes water-cooling pipe 148 as the cooling means, and as a result, an appropriate sterilization process can be performed.

Figure 20A:
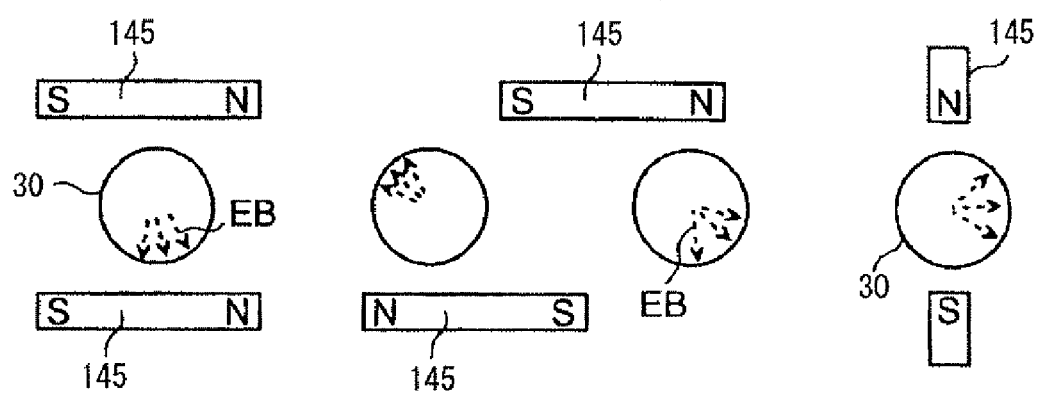
FIGS. 20A and 20B are schematic diagrams showing an arrangement example of the electron beam deflecting means used in the electron beam irradiation apparatus for open-mouthed containers according to the present invention.
Figure 20B:
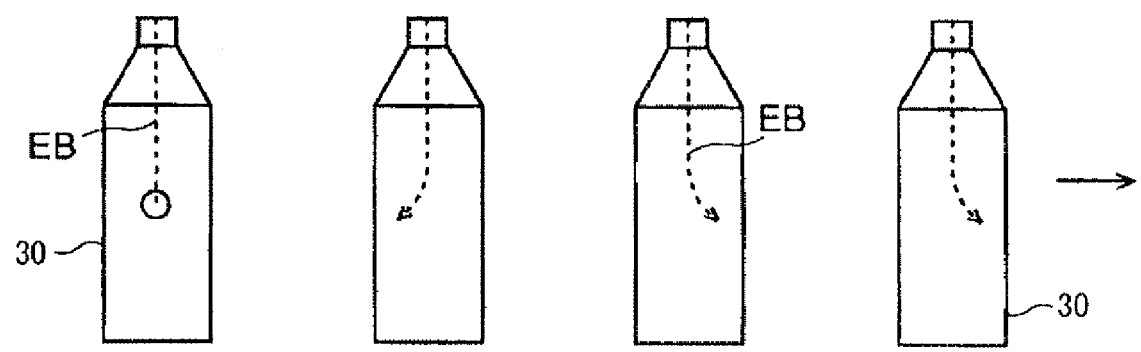

FIGS. 20A and 20B show examples of layout of the electron beam deflector 145 as the electron beam deflecting means, in which permanent magnets are used in the electron beam deflector 145. As shown in FIG. 20A, in each electron beam deflector 145, the N pole and the S pole of permanent magnets are arranged so that they face the inner side and the outer side of an open-mouthed container, or the N pole and the S pole of bar-shaped permanent magnets are displaced relative to each other in the circumferential direction, or the N pole and the S pole of bar-shaped permanent magnets face opposite to each other on both sides. Different layouts were worked out.

In those layouts, as shown in FIGS. 20A and 20B, because the deflection direction of the electron beams EB emitted from the upper side of the drawing are bent at different angles in the circumferential direction in relation to the center axis of an open-mouthed container 30, the sterilization process on the outside and the inside of the open-mouthed container 30 can be performed appropriately.

INDUSTRIAL APPLICABILITY

As has been described, according to the present invention, even for a case where low-energy electron beams are used, it is possible to provide an electron beam irradiation method and an electron beam irradiation apparatus capable of efficient and uniform irradiation of an object with electron beams.

According to the present invention, even for a case where low-energy electron beams are used, it is possible to provide an electron beam irradiation method and an electron beam irradiation apparatus capable of reducing consumption of energy of electron beams and also provide an electron beam irradiation apparatus capable of continuous irradiation with electron beams while reducing consumption of energy of electron beams.

Further, according to the present invention, it is possible to provide an electron beam irradiation apparatus for open-mouthed containers, which is capable of being built in a production line that transports open-mouthed containers at high speed and also capable of effectively sterilizing open-mouthed containers with electron beams in an irradiation process unit maintained at a negative pressure by using generating electron beams of low energy.

Further, according to the present invention, it is possible to provide an electron beam irradiation apparatus for open-mouthed containers, which has a plurality of electron beam generating means suitably arranged and which is capable of appropriately sterilizing the interior and exterior surfaces of open-mouthed containers being transported at high speed substantially same as the production line.

What is claimed is:

1. An irradiation chamber for open-mouthed containers, wherein a front pressure adjusting chamber and a rear pressure adjusting chamber are connected integrally to side faces of an irradiation process chamber for maintaining a negative pressure state with its own pressure reducing means, and a rotating transport device is disposed rotatably in each pressure adjusting chamber, a plurality of holding devices for holding open-mouthed containers are provided at roughly equal intervals on outer surfaces of said rotating transport devices, and wherein said pressure reducing means is provided in such a way that the open-mouthed containers can be transferred one after another from one rotating transport device to the other rotating transport device from said front pressure adjusting chamber to the rear. pressure adjusting chamber, that partition walls are provided at the rotating transport devices in said front and rear pressure adjusting chambers to divide said holding devices to form a plurality of small compartments by using the partition walls and chamber wall surfaces when said rotating transport devices are moving, and that it is arranged that the pressure is reduced in the small compartments in a range from an open-mouthed container entrance side of said front pressure adjusting chamber to the irradiation process chamber side and in the other range from said irradiation process chamber to the open-mouthed container exit side of said rear pressure adjusting chamber, and wherein at least one electron beam irradiation means is arranged in said irradiation process chamber.

2. The electron beam irradiation apparatus for open-mouthed containers according to claim 1, wherein a plurality of electron beam irradiation means are arranged in positions along an open-mouthed-container transporting circular arc of the irradiation process chamber.

3. The electron beam irradiation apparatus for open-mouthed containers according to claim 1, wherein said irradiation process chamber preferably has a diameter larger than that of said front pressure adjusting chamber or said rear pressure adjusting chamber, and a plurality of electron beam irradiation means are arranged above said irradiation process chamber.

4. The electron beam irradiation apparatus according to 1, wherein in said irradiation process chamber as the room for irradiation with electron beams, the electron beam deflecting means are preferably arranged in positions opposed to said electron beam irradiation means and at different heights of open-mouthed containers irradiated with electron beams.

5. The irradiation chamber for open-mouthed containers according to claim 4, wherein a plurality of said electron beam deflecting means are arranged such that deflection directions of electron beams are bent in circumferential direction at different angles with respect to a central axis of open-mouthed containers.

6. The electron beam irradiation apparatus according to claim 1, wherein an axial rotation device for rotating an open-mouthed container on its axis by a rotating drive force caused by the movement of said rotating transport device is arranged to each of a plurality of holding devices mounted on said rotating transport devices in said irradiation process chamber.

7. The electron beam irradiation apparatus for open-mouthed containers according to claim 1, further comprising an electron beam irradiation means for emitting electron beams into an electron beam irradiation area where an object is placed, and a magnetic field barrier forming means for forming a magnetic field barrier in such a way as to enclose the object by joining together a plurality of magnetic fields generated within the electron beam irradiation area, wherein said magnetic field barrier forming means includes a plurality of magnetic field generators arranged to respectively generate magnetic fields to thereby enclose the object in the electron beam irradiation area.

8. The electron beam irradiation apparatus according to claim 7, wherein said magnetic field barrier forming means preferably forms said magnetic field barrier by cusp fields or mirror fields.

9. The electron beam irradiation apparatus according to 7, wherein said magnetic field barrier forming means is configured to be able to change at least one of the reflecting distance and the reflecting direction of electrons within said magnetic field barrier by adjusting the intensity of magnetic fields generated.

10. The electron beam irradiation apparatus for open-mouthed containers according to claim 1, wherein said electron beam irradiation means is installed in an electron beam generating room capable of maintaining an inside pressure, and wherein said irradiation chamber is configured to be adjacent to said electron beam generating room so as to be able to maintain the inside pressure separately from said electron beam generating room, and wherein a pressure control means is provided to perform control so that the electron beam generating room is at a first negative pressure and the irradiation chamber is at a second negative pressure whose absolute pressure is higher than that of the first negative pressure.

11. The electron beam irradiation apparatus for open-mouthed containers according to claim 10, wherein said pressure control means is configured to change the second negative pressure thereby changing the degree of scattering of electrons.

12. The electron beam irradiation apparatus for open-mouthed containers according to claim 10, wherein said front pressure adjusting chamber and said rear pressure adjusting chamber, mounted to side faces of said irradiation process chamber, are configured to be able to maintain their inside pressure separately, and wherein said pressure control means are configured to control the inside pressure of said front pressure adjusting chamber and said rear pressure adjusting chamber separately from the pressure said irradiation process chamber.

13. The electron beam irradiation apparatus for open-mouthed containers according to claim 12, wherein it is configured that the pressure of said front pressure adjusting chamber and said rear pressure adjusting chamber is changed to coincide with the height of the second negative pressure.

14. The electron beam irradiation apparatus for open-mouthed containers according to claim 10, wherein the atmosphere in said irradiation process chamber is one or a plurality of gases selected from air, oxygen, nitrogen, hydrogen, carbon dioxide, argon, and helium.

15. The electron beam irradiation apparatus according to claim 12, wherein a plurality of said pressure adjusting chambers are provided continuously in the transport direction, and wherein adjacent pressure adjusting chambers are mutually separated by partition walls having at least one of a pivoted door or a labyrinth seal structure.

16. The electron beam irradiation apparatus according to claim 10, wherein clean air meeting at least one of conditions of no bacteria and no dust is supplied to said front pressure adjusting chambers, said irradiation chamber, and said rear pressure adjusting chambers when said second negative pressure is controlled.

17. The electron beam irradiation apparatus according to claim 10, wherein said front pressure adjusting chambers, said electron irradiation chamber, and said rear pressure adjusting chambers can be respectively pressure-controlled in multiple stages, and a gas current can be sent in desired directions.

* * * * *